United States Patent
Brugge et al.

(10) Patent No.: US 11,241,442 B2
(45) Date of Patent: Feb. 8, 2022

(54) METHODS OF USE FOR TRP CHANNEL ANTAGONIST-BASED COMBINATION CANCER THERAPIES

(71) Applicant: President and Fellows of Harvard College, Cambridge, MA (US)

(72) Inventors: Joan Siefert Brugge, Boston, MA (US); Nobuaki Takahashi, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 181 days.

(21) Appl. No.: 16/491,752

(22) PCT Filed: Mar. 5, 2018

(86) PCT No.: PCT/US2018/020937
§ 371 (c)(1),
(2) Date: Sep. 6, 2019

(87) PCT Pub. No.: WO2018/165034
PCT Pub. Date: Sep. 13, 2018

(65) Prior Publication Data
US 2021/0128581 A1    May 6, 2021

Related U.S. Application Data

(60) Provisional application No. 62/467,604, filed on Mar. 6, 2017.

(51) Int. Cl.
*A61K 31/555* (2006.01)
*A61P 35/00* (2006.01)
*A61K 45/06* (2006.01)
*C12N 15/113* (2010.01)

(52) U.S. Cl.
CPC ............ *A61K 31/555* (2013.01); *A61K 45/06* (2013.01); *A61P 35/00* (2018.01); *C12N 15/1138* (2013.01)

(58) Field of Classification Search
None
See application file for complete search history.

(56) References Cited

PUBLICATIONS

Gautier et al., British Journal of Pharmacology (2014), 171(10), pp. 2582-2592.*
Bernardini et al., International Journal of Developmental Biology (2015), 59(7/8/9), pp. 399-406.*
Park et al., Cancer Genomics & Proteomics (2016), 13(1), pp. 83-90.*
Ouadid-Ahidouch et al., Trends in Molecular Medicine (2013), 19(2), pp. 117-124.*
Schaefer et al., Biochemical Pharmacology (2013), 85(3), pp. 426-438.*
International Search Report and Written Opinion for International Application No. PCT/US18/20937, dated Aug. 9, 2018 (14 pages).
Ma et al., "Essential role for TrpC5-containing extracellular vesicles in breast cancer with chemotherapeutic resistance," Proc Natl Acad Sci U.S.A. 111(17):6389-94 (2014) (14 pages).
Wang et al., "Inhibition of transient receptor potential channel 5 reverses 5-Fluorouracil resistance in human colorectal cancer cells," J Biol Chem. 290(1):448-56 (2015).
Wen et al., "Regulation of Multi-drug Resistance in hepatocellular carcinoma cells is TRPC6/Calcium Dependent," Sci Rep. 6:23269 (2016) (14 pages).

* cited by examiner

Primary Examiner — Brian J Davis
(74) Attorney, Agent, or Firm — Clark & Elbing LLP

(57) ABSTRACT

The present invention relates to methods for treating cancer through combination therapy with a TRP channel antagonist and standard-of-care cancer agents.

18 Claims, 57 Drawing Sheets

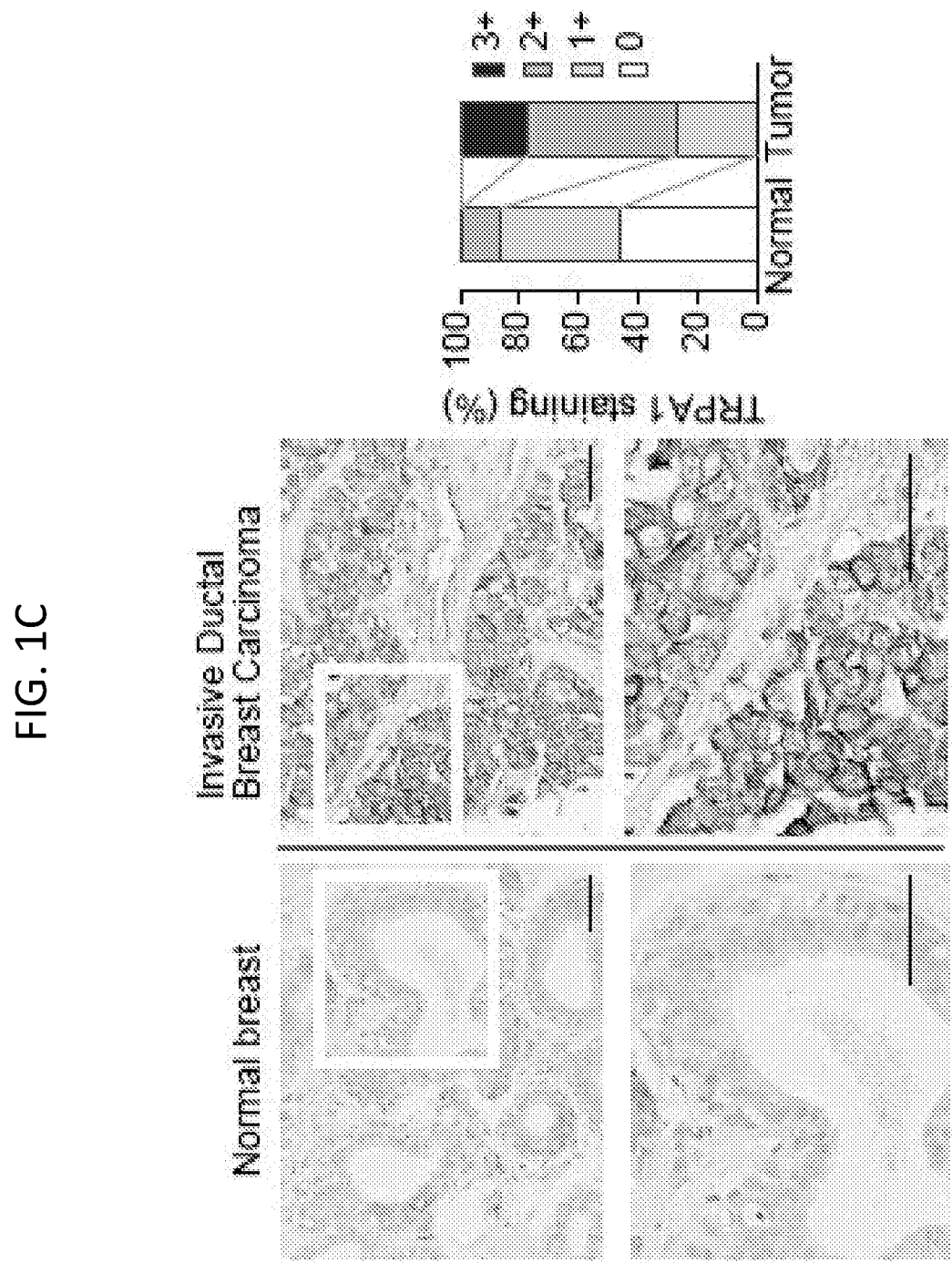

METHODS OF USE FOR TRP CHANNEL ANTAGONIST-BASED COMBINATION CANCER THERAPIES

FIELD OF THE INVENTION

The invention generally relates to the treatment or prevention of cancer.

BACKGROUND OF THE INVENTION

Tumor progression exposes cancer cells to numerous cellular insults, leading to the generation of reactive oxygen species (ROS). Despite upregulation of canonical antioxidant programs, cancer cells exhibit elevated ROS levels in response to these insults. In particular, during tumor progression, cancer cells generate high levels of ROS due to their exposure to numerous cellular insults, including detachment from extracellular matrix (ECM), low levels of $O_2$ (hypoxia), and nutrient deprivation. Many standard-of-care therapies induce high levels of ROS, and elevated cellular antioxidants, and anti-apoptotic programs are correlated with reduced sensitivity to these therapies and poor clinical prognosis.

Thus, there is an unmet need in the field for the development of therapies that can target chemoresistant, ROS-insensitive cancers in order to promote robust cancer treatment outcomes.

SUMMARY OF THE INVENTION

The invention generally provides methods for the treatment of cancer. The inventors find that transient receptor potential (TRP) channels promote tumor growth by allowing cells to tolerate reactive oxygen species which are generated by tumor cells. In addition TRP channels protect cells from the cytotoxicity of several chemotherapy drugs. The inventors find that the mechanism responsible for TRP channel protection from reactive oxygen and chemotherapy involves calcium influx by the TRP channel. The influx of calcium activates several intracellular prosurvival and anti-apoptotic signaling pathways, including Src, Pyk2, Ras and MCL1 proteins, which protect the tumor cells from ROS and effects of chemotherapy. In addition, the inventors show that inhibition of TRP channels enhance the effects of chemotherapeutic agents and suppress the growth of tumors transplanted in mice. The inventors also find that NRF2, an oxidant-defense transcription factor, directly controls TRP channel expression in tumors. Thus, TRP channel antagonists may significantly improve the effectiveness of current cancer therapies in TRP-enriched tumors.

The methods include (a) determining the expression level of a gene in a cancer sample from a subject diagnosed with cancer, where the gene encodes a TRP channel, and (b) administering an anti-cancer agent and an antagonist of the TRP channel to the subject if the expression level of the gene encoding the TRP channel is higher relative to a control biological sample, wherein the anti-cancer agent and the antagonist of the TRP channel are administered in amounts and for durations sufficient to treat cancer in the subject.

Additionally, the invention provides a method for the treatment of cancer in a subject whose cancer has higher expression levels of a gene encoding a TRP channel relative to a control biological sample. This method includes the step of administering an anti-cancer agent and an antagonist of the TRP channel to the subject, wherein the anti-cancer agent and the antagonist of the TRP channel are administered in amounts and for durations sufficient to treat cancer in the subject.

The methods of the invention can also include (a) administering an anti-cancer agent to a subject diagnosed with cancer, and (b) determining whether the anti-cancer agent increases the expression level of a gene in a cancer sample from a subject, wherein the gene encodes a transient receptor potential (TRP) channel, and (c) administering the anti-cancer agent and an antagonist of the TRP channel to the subject if the expression level of the gene encoding the TRP channel is higher relative to a control biological sample, wherein the anti-cancer agent and the antagonist of the TRP channel are administered in amounts and for durations sufficient to treat cancer in the subject.

In some embodiments, the TRP channel antagonist is not an endogenous antagonist of the TRP channel.

In some embodiments, the TRP channel is transient receptor potential cation channel, subfamily A, member 1 (TRPA1); transient receptor potential cation channel, subfamily C, member 7 (TRPC7); transient receptor potential cation channel, subfamily C, member 2 (TRPC2); transient receptor potential cation channel, subfamily C, member 3 (TRPC3); transient receptor potential cation channel, subfamily C, member 5 (TRPC5); transient receptor potential cation channel, subfamily C, member 6 (TRPC6); transient receptor potential cation channel, subfamily C, member 4 (TRPC4); transient receptor potential cation channel, subfamily M, member 7 (TRPM7); transient receptor potential cation channel, subfamily M, member 1 (TRPM1); transient receptor potential cation channel, subfamily M, member 2 (TRPM2); transient receptor potential cation channel, subfamily M, member 6 (TRPM6); transient receptor potential cation channel, subfamily M, member 8 (TRPM8); transient receptor potential cation channel, subfamily M, member 4 (TRPM4); transient receptor potential cation channel, subfamily M, member 5 (TRPM5); transient receptor potential cation channel, subfamily M, member 2 (TRPM2); transient receptor potential cation channel, subfamily M, member 3 (TRPM3); polycystin-2 (PKD2); polycystic kidney disease 2-like 1 (PKD2L1); polycystic kidney disease 2-like 2 (PKD2L2); transient receptor potential cation channel, mucolipin subfamily, member 2 (TRPML2); transient receptor potential cation channel, mucolipin subfamily, member 1 (TRPML1); transient receptor potential cation channel, mucolipin subfamily, member 3 (TRPML3); transient receptor potential cation channel, subfamily V, member 1 (TRPV1); transient receptor potential cation channel, subfamily V, member 4 (TRPV4); transient receptor potential cation channel, subfamily V, member 6 (TRPV6); transient receptor potential cation channel, subfamily V, member 5 (TRPV5); transient receptor potential cation channel, subfamily V, member 3 (TRPV3); or transient receptor potential cation channel, subfamily V, member 2 (TRPV2).

In some embodiments, the cancer is any one of the group of sarcomas, adenocarcinomas, and carcinomas, of the various organ systems, including colon cancers, rectal cancer, renal-cell carcinoma, liver cancer, non-small cell carcinoma of the lung, cancer of the small intestine and cancer of the esophagus, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of the cancers.

In certain embodiments, the antagonist of the TRP channel targets the gene, gene product, or regulatory RNAs of the TRP channel.

In some embodiments, the chemotherapeutic is doxorubicin, gemcitabine, carboplatin, or an aromatase antagonist. In some embodiments, the chemotherapeutic agent is an electrophilic compound that activates a TRP channel (e.g., a TRPA1 channel).

In some embodiments, the expression level of a gene is determined by determining mRNA expression level, cDNA expression level, or protein expression level.

In other embodiments, the biological sample comprises mRNA, cDNA, and/or protein from the subject.

Definitions

As used herein, the term "about" refers to a value that is within 10% above or below the value being described.

As used herein, an "anchorage-independent colony" refer to a group of cells generated from a single cell by mitotic cell proliferation. The assay for this property is carried out under conditions in which cells are not anchored to any substrate (typically in a solution of soft agar). This property has been shown to be most predictive of tumor formation after xenograft transplantation of tumor cell.

As used herein, "acini" refer to the polarized, growth-arrested spheroids comprising mammary epithelial cells three-dimensionally cultured on a reconstituted basement membrane.

As used herein, "adjuvant" refers to a pharmacological agent that modifies the effect of other agents (e.g., a chemotherapeutic agent) while having few if any direct effects when given by itself.

As used herein, "administering" is meant a method of giving a dosage of a pharmaceutical composition to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. The preferred method of administration can vary depending on various factors (e.g., the components of the composition being administered and the severity of the condition being treated).

As used herein, "antagonists" refer to compounds which inhibit or reduce the biological activity of the molecule to which they bind.

As used herein, "treating cancer," "preventing cancer," or "inhibiting cancer" is meant causing a reduction in the size of a tumor or the number of cancer cells, slowing, preventing, or inhibiting an increase in the size of a tumor or cancer cell proliferation, increasing the disease-free survival time between the disappearance of a tumor or other cancer and its reappearance, preventing or reducing the likelihood of an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay, such as those described herein. Desirably, the decrease in the number of tumor or cancerous cells induced by administration of a compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or number of cancerous cells as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after no less than 5, 10, 15, or 20 years.

As used herein, "control sample" is meant a biological sample which is from the subject and does not contain cancerous cells or other abnormalities.

As used herein, the word "comprise," or variations such as "comprises" or "comprising," will be understood to imply the inclusion of a stated integer or group of integers but not the exclusion of any other integer or group of integers.

As used herein, "isolated" is meant separated, recovered, or purified from a component of its natural environment. For example, a nucleic acid molecule or polypeptide of the invention may be isolated from a component of its natural environment by 1% (2%, 3%, 4%, 5%, 6%, 7%, 8% 9% 10%, 20%, 30%, 40%, 50%, 60% 70%, 80%, or 90%) or more by weight.

As used herein, "gene product" is meant to include mRNAs transcribed from a gene (and any corresponding complementary DNAs (cDNAs)), as well as polypeptides translated from those mRNAs.

As used herein, "host cell" refers to cells into which a heterologous nucleic acid molecule has been introduced, including the progeny of such cells. Host cells include "transformants" and "transformed cells," which include the primary transformed cell and progeny derived therefrom without regard to the number of passages. Host cells include cells within the body of a subject (e.g., a mammalian subject (e.g., a human)) into which the heterologous nucleic acid molecule has been introduced.

As used herein, "pharmaceutical composition" is meant any composition that contains a therapeutically or biologically active agent, that is suitable for administration to a subject and that treats or prevents a disease (e.g., cancer) or reduces or ameliorates one or more symptoms of the disease. For the purposes of this invention, pharmaceutical compositions include, but are not limited to, small-molecule compounds, and pharmaceutical compositions suitable for delivering a therapeutic or biologically active agent can be, for example, tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, solutions, injectables, implants, sprays, or aerosols.

As used herein, "pharmaceutical formulation" refers to a sterile preparation that is in such form as to permit the biological activity of the medicament to be effective, and which contains no additional components that are unacceptably toxic to a subject to which the formulation would be administered.

As used herein, "pharmaceutically acceptable diluent, excipient, carrier, or adjuvant" is meant a diluent, excipient, carrier, or adjuvant, respectively, which is physiologically acceptable to the subject while retaining the therapeutic properties of the pharmaceutical composition with which it is administered. One pharmaceutically acceptable carrier is physiological saline. Other physiologically acceptable diluents, excipients, carriers, or adjuvants and their formulations are known to one skilled in the art (see, e.g., U.S. Patent Pub. No. 2012/0076812).

As used herein, "therapeutically effective amount" is meant an amount of a therapeutic agent that alone, or together with one or more additional (optional) therapeutic agents, produces beneficial or desired results upon administration to a mammal, such as a human. The therapeutically effective amount depends upon the context in which the therapeutic agent is applied. In general, a therapeutically effective amount of a composition administered to a subject (e.g., a human) will vary depending upon a number of factors associated with that subject, for example the overall health of the subject, the condition to be treated, or the severity of the condition. A therapeutically effective amount of a composition can be determined by varying the dosage of the product and measuring the resulting therapeutic response.

As used herein, and as well understood in the art, "treatment" or "therapy" is an approach for obtaining beneficial or desired results, such as clinical results. Beneficial or desired results can include, but are not limited to, alleviation or amelioration of one or more symptoms or conditions associated with a cancer, including, without limitation, fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, "subject" is meant any animal. In one embodiment, the subject is a human. Other animals that can be treated using the methods, compositions, and kits of the invention include but are not limited to non-human primates (e.g., monkeys, gorillas, chimpanzees), domesticated animals (e.g., horses, pigs, goats, rabbits, sheep, cattle, llamas), and companion animals (e.g., guinea pigs, rats, mice, lizards, snakes, dogs, cats, fish, hamsters, and birds).

As used herein, "anti-neoplastic composition," "anti-cancer composition," and "anti-cancer agent" refer to a composition useful in treating cancer comprising at least one active therapeutic agent, e.g., "anti-cancer agent."

As used herein, a "chemotherapeutic agent" is a chemical compound useful in the treatment of cancer.

As used herein, "cytotoxic agent" refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re_{188}$, $Sm^{153}$, $Bi^{212}$, $P^{32}$ and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof. A tumoricidal agent causes destruction of tumor cells and is considered both a chemotherapeutic agent and a cytotoxic agent.

As used herein, a "growth inhibitory agent" refers to a compound or composition which inhibits growth and/or proliferation of a cell either in vitro or in vivo. Desirably, a slowing of the growth rate is by at least 20%, 30%, 50%, 60%, 70%, 80%, or 90%, as determined using a suitable assay for determination of cell growth rates. Typically, a reversal of growth rate is accomplished by initiating or accelerating necrotic or apoptotic mechanisms of cell death in the neoplastic cells. Thus, the growth inhibitory agent may be one which significantly reduces the percentage of cells in S phase. A growth inhibitory agent that inhibits the growth and/or proliferation of cancer cells can be useful as a chemotherapeutic agent.

As used herein, a "reactive oxygen species (ROS)-inducing agent" refers to a compound or composition which stimulates endogenous ROS production. ROS can be categorized into two groups: free oxygen radicals and non-radical ROS. Free oxygen radicals include superoxide ($O_2^{*-}$), hydroxyl radical (*OH), nitric oxide (NO*), organic radicals (R*), peroxyl radicals (ROO*), alkoxyl radicals (RO*), thiyl radicals (RS*), sulfonyl radicals (ROS*), thiyl peroxyl radicals (RSOO*), and disulfides (RSSR). Non-radical ROS include hydrogen peroxide ($H_2O_2$), singlet oxygen ($^1O_2$), ozone/trioxygen ($O_3$), organic hydroperoxides (ROOH), hypochloride (HOCl), peroxynitrite ($ONO^-$), nitrosoperoxycarbonate anion ($O=NOOCO_2^-$), nitrocarbonate anion ($O_2NOCO_2^-$), dinitrogen dioxide ($N_2O_2$), nitronium ($NO_2^+$), and highly reactive lipid- or carbohydrate-derived carbonyl compounds (see, e.g., Liou and Storz, Free Radic Res. 44:479-496, 2010).

As used herein, "biomarker" and "marker" interchangeably refer to a DNA, RNA, protein, carbohydrate, or glycolipid-based molecular marker, the expression or presence of which in a subject's sample can be detected by standard methods (or methods disclosed herein) and is useful for monitoring the responsiveness or sensitivity of a mammalian subject to an antagonist.

As used herein, "level of expression" and "expression level" interchangeably refer to the amount of a polynucleotide or an amino acid product or protein in a biological sample. "Expression" generally refers to the process by which gene-encoded information is converted into the structures present and operating in the cell. Therefore, according to the invention "expression" of a gene product may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. "Expressed genes" include those that are transcribed into a polynucleotide as mRNA and then translated into a protein, and also those that are transcribed into RNA but not translated into a protein (for example, transfer and ribosomal RNAs).

As used herein, "sample" and "biological sample" interchangeably refer to any biological sample obtained from an individual including body fluids, body tissue (e.g., tumor tissue), cells, or other sources. Body fluids are, e.g., lymph, sera, whole fresh blood, peripheral blood mononuclear cells, frozen whole blood, plasma (including fresh or frozen), urine, saliva, semen, synovial fluid and spinal fluid. Samples also include breast tissue, renal tissue, colonic tissue, brain tissue, muscle tissue, synovial tissue, skin, hair follicle, bone marrow, and tumor tissue. Methods for obtaining tissue biopsies and body fluids from mammals are well known in the art.

The phrase "identifying a subject" or "identifies a subject" as used herein, refers to using the information or data generated relating to the level or presence of the gene in a sample of a subject to identify or select the subject as more likely to benefit or less likely to benefit from a therapy. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of at least one gene products to a reference level. In some embodiments, the information or data includes an indication that at least one gene product is present or absent in the sample. In some embodiments, the information or data includes an indication that the subject is more likely or less likely to respond to a therapy.

As used herein, "effective amount" refers to an amount of a drug effective to treat a disease or disorder, such as cancer, in a subject, such as a mammal, e.g., a human. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, duration of progression free survival (PFS), overall survival (OS), the response rates (RR), duration of response, and/or quality of life.

As used herein, an "effective response" of a subject or a subject's "responsiveness" or "sensitivity" to treatment refers to the clinical or therapeutic benefit imparted to a subject at risk for or having a cancer from or as a result of the treatment. Such benefit includes cellular or biological responses, a complete response, a partial response, a stable disease (without progression or relapse), or a response with a later relapse of the subject from or as a result of the treatment. For example, an effective response can be reduced tumor size, increased progression-free survival (PFS), and/or increased overall survival (OS) in a subject diagnosed as expressing a higher or lower level of one or more biomarkers compared to a reference level (including, e.g., the median expression level of the biomarker in a sample from a group/population of subjects being tested for responsiveness to a treatment; the median expression level of the biomarker in a sample from a group/population of subjects having cancer and identified as not responding to treatment; the level in a sample previously obtained from the individual at a prior time; or the level in a sample from a subject who received prior treatment in a primary tumor setting, and who now may be experiencing metastasis). The expression of genetic biomarker(s) effectively predicts, or predicts with high sensitivity, such effective response.

As used herein, "survival" refers to the subject remaining alive, and includes progression-free survival (PFS) and overall survival (OS). Survival can be estimated by the Kaplan-Meier method, and any differences in survival are computed using the stratified log-rank test.

As used herein, "overall survival" or "OS" refers to the subject remaining alive for a defined period of time, such as about 1 year, about 2 years, about 3 years, about 4 years, about 5 years, about 10 years, etc., from initiation of treatment or from initial diagnosis. In the studies underlying the present invention the event used for survival analysis was death from any cause.

As used herein, "progression-free survival" or "PFS" refers to the time from treatment (or randomization) to first disease progression or death. For example it is the time that the subject remains alive, without return of the cancer, e.g., for a defined period of time such as about 1 month, about 2 months, about 3 months, about 4, months, about 5 months, about 6 months, about 7 months, about 8 months, about 9 months, about 1 year, about 2 years, about 3 years, etc., from initiation of treatment or from initial diagnosis. In one aspect of the invention, PFS can be assessed by the MacDonald Response Criteria as described in MacDonald et al. (J. Clin. Oncol. 8:1277-1280, 1990). As used herein, "overall response rate" or "objective response rate" (ORR) refers to the percentage of people who experience a decrease in the size or amount of the cancer for a minimum amount of time, and ORR can be represented by the sum of the complete and partial response rates.

As used herein, "cancer" and "cancerous" refer to or describe the physiological condition in mammals that is typically characterized by unregulated cell growth. Included in this definition are benign and malignant cancers as well as dormant tumors or micrometastases.

As used herein, "tumor" refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

As used herein, the phrase "specifically binds" refers to a binding reaction which is determinative of the presence of a receptor in a heterogeneous population of proteins and other biological molecules that is recognized, e.g., by a ligand with particularity. A ligand that specifically binds to a receptor will bind to the receptor with a $K_D$ of less than 100 nM. For example, a ligand that specifically binds to a receptor will bind to the receptor with a $K_D$ of up to 100 nM (e.g., between 1 pM and 100 nM). A ligand that does not exhibit specific binding to a receptor or a domain thereof will exhibit a $K_D$ of greater than 100 nM (e.g., greater than 500 nm, 1 μM, 100 μM, 500 μM, or 1 mM) for that particular receptor or domain thereof. A variety of assay formats may be used to select ligands that specifically bind to a particular receptor. For example, solid-phase ELISA assays are routinely used to select ligands that specifically bind a receptor.

Other features and advantages of the invention will be apparent from the following detailed description, and from the claims.

BRIEF DESCRIPTION OF THE DRAWINGS

FIG. 1C is a series of representative images of TRPA1 IHC in normal breast tissue and breast tumor sections, and the score of staining level (n=15 for normal breast tissues, n=70 for breast tumors). Enlarged views of the boxed regions shown in lower panel. Scale bar 50 μm.

FIG. 5O is a graph of averaged time courses of $\Delta[Ca^{2+}]_i$ evoked by 30 μM AITC in the indicated MPNST cells treated with or without 10 μM AP-18. Data shown as mean±SEM (n=12-100). ***P<0.001 (Student's t test).

DETAILED DESCRIPTION OF THE INVENTION

Figure 1A:
FIG. 1A is a series of box plots displaying TRP channel mRNA levels in TOGA breast tumors (n=389) relative to normal breast tissues (n=61).

The mammalian family of transient receptor potential (TRP) proteins comprises 28 subtypes of $Ca^{2+}$-permeable channels. Among TRP family members, the irritant receptor TRPA1 exhibits the highest sensitivity to ROS due to the presence of hyper-reactive cysteine (Cys) thiols and has a critical role in sensing oxidative stress in sensory neurons. TRPA1 is also activated by cancer therapies in sensory neurons, including platinum-based drugs and aromatase antagonists, and this activation is associated with therapy-induced pain. The invention discloses that TRPA1 is also activated by ROS-associated chemotherapies, including carboplatin, and mediates chemoresistance in breast, lung, and malignant peripheral nerve sheath tumor cells in which TRPA1 is expressed. TRPA1 inhibition suppresses tumor growth and enhances carboplatin sensitivity in breast tumor xenografts.

As TRPA1 antagonists are currently under clinical evaluation as novel pain and respiratory therapies and have not shown any evidence of significant central nervous system or other drug-related side effects, the invention identifies TRP channels, namely TRPA1, as a cancer therapeutic targets in combination with standard-of-care chemotherapies.

TRP Channels

The mammalian family of transient receptor potential (TRP) proteins comprises 28 subtypes of $Ca^{2+}$-permeable channels that exhibit an extraordinary diversity of activation triggers, modes of activation, signal transduction, and tissue distributions, and play critical roles in a wide variety of physiological and pathological responses (Table 1). A group of TRP channels has emerged as acute sensors of redox status, mediating $Ca^{2+}$ influx in response to changes in the cellular redox environment. In particular, among TRP family members, the irritant receptor TRPA1 exhibits the highest sensitivity to ROS due to the presence of hyper-reactive cysteine (Cys) thiols and plays a critical role in sensing oxidative stress in sensory neurons. Interestingly, TRPA1 is also activated by cancer therapies in sensory neurons, including platinum-based drugs and aromatase antagonists, and this activation is associated with therapy-induced pain. However, despite the known importance of $Ca^{2+}$ signaling in a wide range of cellular functions, including cell proliferation and survival, the role of redox-sensitive TRP channels in oxidative stress adaptation and chemoresistance of cancer cells has not been previously examined.

TABLE 1

| TRP Channels | | | | |
|---|---|---|---|---|
| TRPC7 | TRPC4 | TRPM4 | TRPM5 | TRPM2 |
| PKD2L1 | TRPML2 | TRPA1 | TRPML1 | TRPV1 |
| TRPV2 | TRPC2 | PKD2L2 | TRPC5 | TRPML3 |
| TRPC3 | TRPV3 | TRPM3 | TRPC6 | TRPC1 |
| PKD2 | TRPM1 | TRPM6 | TRPM8 | TRPV5 |
| TRPV6 | TRPV4 | TRPM7 | | |

In certain aspects, the present invention provides methods for treating or ameliorating the effects of diseases and conditions using small molecules that inhibit a TRPA1-mediated current and/or a TRPA1-mediated ion flux with an $IC_{50}$ of less than 10 μM. Suitable compounds for use in any of the methods of the invention (e.g., to treat any of the diseases or conditions disclosed herein) include compounds having one or more of the structural or functional characteristics disclosed herein (e.g., structure, specificity, potency, solubility, etc.). The present invention contemplates the use of any TRPA1 antagonist possessing one or more of the functional or structural attributes described herein.

TRP Antagonists

In certain embodiments, a suitable compound inhibits an inward and/or outward TRP mediated current with an $IC_{50}$ of less than 10 μM. In certain embodiments, a suitable compound additionally or alternatively inhibits TRP mediated ion flux with an $IC_{50}$ of less than 10 μM. $IC_{50}$ can be calculated, for example, in an in vitro assay. For example, $IC_{50}$ can be calculated using electrophysiological determinations of current, such as standard patch clamp analysis. $IC_{50}$ can also be evaluated using changes in concentration or flux of ion indicators, such as the calcium flux methods described herein. In particular embodiments, a small molecule TRP antagonist is chosen for use because it is more selective for one TRP isoform than others, e.g., 10-fold, and more preferably at least 20, 40, 50, 60, 70, 80, or at least 100- or even 1000-fold more selective for TRPA1 over one or more of TRPC6, TRPV5, TRPV6, TRPM8, TRPV1, TRPV2, TRPV 4, and/or TRPV3. In other embodiments, the differential is smaller, e.g., it more strongly inhibits TRPA1 than TRPM8, TRPV1, TRPV2, TRPV3, and/or TRPV4, preferably at least twice, three times, five times, or even ten times more strongly. Such comparisons may be made, for example, by comparing $IC_{50}$ values. In particular embodiments, a small molecule TRPA1 antagonist is chosen for use because it is more selective for one TRPA1 than for other non-TRP ion channels, e.g., 10-fold, and more preferably at least 20, 40, 50, 60, 70, 80, or at least 100- or even 1000-fold more selective for TRPA1 over one or more of NaV1.2, Cav1.2, Cav3.1, HERG, and/or mitochondrial uniporter. In other embodiments, the differential is smaller, e.g., it more strongly inhibits TRPA1 than NaV1.2, Cav1.2, Cav3.1, HERG, and/or mitochondrial uniporter, preferably at least twice, three times, five times, or even ten times more strongly. Such comparisons may be made, for example, by comparing $IC_{50}$ values. Similarly, in particular embodiments, a small molecule is chosen for use because it lacks significant activity against one or more targets other than TRPA1. For example, the compound may have an $IC_{50}$ above 500 nM, above 1 µM, or even above 10 µM or 100 µM for inhibiting one or more of TRPC6, TRPV5, TRPV6, Cav1.2, Cav3.1, NaV1.2, HERG, and the mitochondrial uniporter.

In certain embodiments of any of the foregoing, the small molecule may be chosen because it inhibits a TRP function with an $IC_{50}$ less than or equal to 1 µM, or even less than or equal to 700, 600, 500, 400, 300, 250, 200, or 100 nM. In other embodiments, the small molecule is chosen because it inhibits a TRPA1 function with an $IC_{50}$ less than or equal to 75 nM, less than or equal to 50 nM, or even less than or equal to 25, 10, 5, or 1 nM. In certain other embodiments of any of the foregoing, the small molecule inhibits TRP function with an IC50 less than or equal to 10 µM or less than or equal to 5 µM or less than or equal to 2.5 µM or less than or equal to 1.5 µM. In certain embodiments of any of the foregoing, the compound may be chosen based on the rate of inhibition of a TRP function. In one embodiment, the compound inhibits a TRP function in less than 5 minutes, preferably less than 4, 3, or 2 minutes. In another embodiment, the compound inhibits a TRP function in less than about 1 minute. In yet another embodiment, the compound inhibits a TRP function in less than about 30 seconds.

In certain embodiments of any of the foregoing, inhibition of a TRP function means that a function, for example a TRP mediated current, is decreased by greater than 50% in the presence of an effective amount of a compound in comparison to in the absence of the compound or in comparison to an ineffective amount of a compound. In certain other embodiments, the inhibition of a TRP function means that a function, for example a TRP mediated current or TRP mediated ion flux, is decreased by at least 50%, 60%, 70%, 75%, 80%, 85%, or 90% in the presence of an effective amount of a compound in comparison to in the absence of the compound. In still other embodiments, the inhibition of a TRP function means that a function, for example a TRP mediated current, is decreased by at least 92%, 95%, 97%, 98%, 99%, or 100% in the presence of an effective amount of a compound in comparison to in the absence of the compound.

Without being bound by theory, a compound may inhibit a function of a TRP channel by binding covalently or non-covalently to a portion of a TRP channel. Alternatively, a compound may inhibit a function of a TRP channel indirectly, for example, by associating with a protein or non-protein cofactor necessary for a function of a TRP channel. One of skill in the art will readily appreciate that an inhibitory compound may associate reversibly or irreversibly with a TRP channel or a cofactor thereof. Compounds that reversibly associate with a TRP channel or a cofactor thereof may continue to inhibit a function of a TRP channel even after dissociation. In certain embodiments of any of the foregoing, the compound that inhibits a function of a TRP channel is a small organic molecule or a small inorganic molecule. Small molecules include, but are not limited to, small molecules that bind to a TRP channel and inhibit one or more functions of a TRP channel. The subject TRP antagonists can be used alone or in combination with other pharmaceutically active agents.

A. TRP Antagonists

TRPA1 antagonists include HC-030031 as described in McNamara et al., Proc. Natl. Acad. Sci. USA, 104: 13525-13530, 2007, AP18 as described in Petrus et al., Mol. Pain, 3:40, A-967079, 2007, as described in Chen et al., Pain, 152:1165-1172, 2011, compound 10 as described in Copeland et al., Bioorg. Med. Chem. Lett., 24:3464-3468, 2014, AM-0902 as described in Schenkel et al., J. Med. Chem., 59:2794-2809, 2016, compounds 1-48 as described in Preti et al., Pharm. Pat. Anal. 4:75-94, 2015, and the TRPA1 antagonists described in WO 2007073505, WO 2010138879, WO 2009140519, WO 2009002933, WO 2010075353, WO 2010132838, WO 2009158719, WO 2014113671, WO 2009118596, US 20090325987, WO 2010109287, WO 2010109328, WO 2010109334, WO 2010125469, WO 2011132017, WO 2011114184, WO 2009144548, WO 2009147079, WO 2010141805, WO 2014049047, WO 2014076038, WO 2014056958, WO 2014072325, WO 2014076021, WO 2007098252, WO 2009089082, WO 2009089083, WO 2011043954, WO 2012050512, WO 2012152983, WO 2014053694, WO 2016128529, and WO 2014135617, each of which is herein incorporated by reference.

TRPM2 antagonists include flufenamic acid and 2-aminoethoxydiphenyl borate (2-APB).

TRPM3 antagonists include fenamates (e.g., mefenamic acid), ononetin (1-(2,4-Dihydroxyphenyl)-2-(4-methoxyphenyl)ethanone), isosakuranetin, liquiritigenin, naringenin, eriodictyol, troglitazone, pioglitazone, and hesperetin.

TRPM4 antagonists include flufenamic acid, 9-phenanthrol, and spermine.

TRPM5 antagonists include flufenamic acid and spermine.

TRPM7 antagonists include spermine, sphingosine, fingolimod, NS8593, waixenicin A, 2-APB, carvacrol, and nafamostat (see, e.g., Chubanov et al., Br. J. Pharmacol., 166:1357-1376, 2012).

TRPM8 antagonists include capsazepine, 5-benzyloxytryptamine, linoleic acid, anandamide, $\Delta^9$-tetrahydrocannabinol, and cannabidiol.

TRPC1 antagonists include GsMTx4 (GCLEFWWKCNPNDDKCCRPKLKCSKLFKLCNFSF) (SEQ ID NO: 81), SKF96365 (1-[2-(4-Methoxyphenyl)-2-[3-(4-methoxyphenyl) propoxy]ethyl]imidazole, 1-[β-(3-(4-Methoxyphenyl)propoxy)-4-methoxyphenethyl]-1H-imidazole hydrochloride), and 2-APB.

TRPC2 antagonists include 2-APB and U73122 (1-[6-[((17β)-3-Methoxyestra-1,3,5[10]-trien-17-yl)amino] hexyl]-1H-pyrrole-2,5-dione).

TRPC3 antagonists include Pyr3 (1-[4-[(2,3,3-Trichloro-1-oxo-2-propen-1-yl)amino]phenyl]-5-(trifluoromethyl)-1H-pyrazole-4-carboxylic acid) and KB-R7943 (2-[4-[(4-nitrophenyl)methoxy]phenyl]ethyl ester, methanesulfonate (1:1), Carbamimidothioic acid).

TRPC4 antagonists include ML204 (4-Methyl-2-(1-piperidinyl)-quinoline), niflumic acid, and 2-APB.

TRPC5 antagonists include clemizole hydrochloride (1-[(4-Chlorophenyl)methyl]-2-(1-pyrrolidinylmethyl)-1H-benzimidazole hydrochloride), M 084 hydrochloride (N-Butyl-1H-benzimidazol-2-amine hydrochloride), bromoenol lactone, flufenamic acid, and chlorpromazine.

TRPC6 antagonists include SKF96365, amiloride, 2-APB, GsMTx-4, and KB-R7943.

TRPC7 antagonists include SKF96365, amiloride, and 2-APB.

TRPV1 antagonists include capsazepine (N-[2-(4-Chlorophenyl)ethyl]-1,3,4,5-tetrahydro-7,8-dihydroxy-2H-2-benzazepine-2-carbothioamide), 1,3-di(arylalkyl)thioureas (e.g., JYL1421), capsaicin analogs of the urea type (e.g., phenylacetylrinvanil, BCTC, neurogen, A-425619 (1-isoquinolin-5-yl-3-(4-trifluoromethyl-benzyl)-urea), SB-705498 ((R)-1-(2-bromophenyl)-3-(1-(5-(trifluoromethyl)pyridin-2-yl)pyrrolidin-3-yl)urea), SB-452533 (N-(2-Bromophenyl)-N'-[2-[ethyl(3-methylphenyl)amino]ethyl] urea), and ABT-102 ((R)-1-(5-tert-Butyl-2,3-dihydro-1H-inden-1-yl)-3-(1H-indazol-4-yl)urea)), cinnamides (e.g., SB-366791 (N-(3-Methoxyphenyl)-4-chlorocinnamide), AMG9810 (2E-N-(2,3-Dihydro-1,4-benzodioxin-6-yl)-3-[4-(1,1-dimethylethyl)phenyl]-2-Propenamide), and AMG0347 (N-(7-hydroxy-5,6,7,8-tetrahydronaphthalen-1-yl)-3-(2-(piperidin-1-yl)-6-(trifluoromethyl)pyridin-3-yl) acrylamide)), carboxamides (e.g., SB-782443 (6-(4-fluorophenyl)-2-methyl-N-(2-methylbenzothiazol-5-yl) nicotinamide)), JNJ 17203212 (4-[3-(Trifluoromethyl)-2-pyridinyl]-N-[5-(trifluoromethyl)-2-pyridinyl]-1-piperazinecarboxamide), arachidonyl serotonin, AZD1386 (see, e.g., US 2009176851), and AMG517 (N-(4-(6-(4-trifluoromethylphenyl)pyrimidin-4-yloxy)benzothiazol-2-yl)acetamide).

TRPV2 antagonists include tetraethylammonium, fampridine, ruthenium red, amiloride, and SKF96365.

TRPV3 antagonists include compound 74a ((1R,3r)-3-(4-tert-butylpyridin-2-yl)-3-[(S)-hydroxy(pyridin-2-yl) methyl]-1-methylcyclobutan-1-ol) (see, e.g., U.S. Pat. No. 8,940,771), ruthenium red, and diphenyltetrahydrofuran.

TRPV4 antagonists include RN 9893 hydrochloride (N-[4-[[4-(1-Methylethyl)-1-piperazinyl]sulfonyl]phenyl]-2-nitro-4-(trifluoromethyl)benzamide hydrochloride), GSK 2193874 (3-([1,4'-Bipiperidin]-1'-ylmethyl)-7-bromo-N-(1-phenylcyclopropyl)-2-[3-(trifluoromethyl)phenyl]-4-quinolinecarboxamide), HC 067047 (2-Methyl-1-[3-(4-morpholinyl)propyl]-5-phenyl-N-[3-(trifluoromethyl)phenyl]-1H-pyrrole-3-carboxamide), and ruthenium red.

TRPV5 antagonists include ruthenium red.

PKD2L1 antagonists include flufenamic acid, phenamil, benzamil, ethylisopropylamiloride, amiloride, and flufenamate.

PKD2 antagonists include SKF96365.

Methods to Identify Subjects Responsive to TRP Antagonists

The present invention provides methods for identifying and/or monitoring subjects likely to be responsive to TRP antagonist (e.g., a TRPA1 antagonist) therapy. The methods are useful, inter alia, for increasing the likelihood that administration of a TRP antagonist (e.g., a TRPA1 antagonist) to a subject will be efficacious. The methods include detecting expression of one or more genetic biomarkers in a biological sample from a subject, wherein the expression of one or more such biomarkers is indicative of whether the subject is sensitive or responsive to TRP antagonists.

More particularly, determining the expression level of at least one of the genes set forth in Table 1 below (e.g., 1, 2, 3, 4, 5, 6, 7, 8, 9, 10, 11, 12, 13, 14, 15, 16, 17, 18, 19, 20, 21, 22, 23, 24, 25, 26, 27, or 28 of the genes listed in Table 1) in a sample from a subject is useful for monitoring whether the subject is responsive or sensitive to a TRP antagonist. For any of the methods described herein, one could, for example, determine the expression levels of any combination of 2, 3, 4, 5, 6, 7, 8, 9, 10, 11, 12, 13, 14, 15, 16, 17, 18, 19, 20, 21, 22, 23, 24, 25, 26, 27, or 28 genes selected from the genes listed in Table 1. Alternatively, for any of the methods described herein, the expression level of all 28 genes (TRPC7, TRPC4, TRPM7, TRPM4, TRPM5, TRPM2, PKD2L1, TRPML2, TRPA1, TRPML1, TRPV1, TRPV2, TRPC2, PKD2L2, TRPC5, TRPML3, TRPC3, TRPV3, TRPM3, TRPC6, TRPC1, PKD2, TRPM1, TRPM6, TRPM8, TRPV5, TRPV6, and TRPV4) listed in Table 1 can be determined.

In one example, determining the expression level of at least 1, 2, 3, 4, 5, 6, 7, 8, 9, 10, 11, 12, 13, 14, 15, 16, 17, 18, 19, 20, 21, 22, 23, 24, 25, 26, 27, or 28 of the genes listed in Table 1 in a sample from a subject is useful for monitoring whether the subject is responsive or sensitive to a TRP antagonist, such as a TRPA1 antagonist. In one example, determining the expression level of all 28 genes listed in Table 1 in a sample from a subject is useful for monitoring whether the subject is responsive or sensitive to a TRP antagonist, such as a TRPA1 antagonist. In some instances, for any of the methods described herein, the expression level of at least 2 genes (e.g., 2, 3, 4, 5, 6, 7, 8, 9, 10, 11, 12, 13, 14, 15, 16, 17, 18, 19, 20, 21, 22, 23, 24, 25, 26, 27, 28 or more genes) in total can be determined.

The disclosed methods and assays provide for convenient, efficient, and potentially cost-effective means to obtain data and information useful in assessing appropriate or effective therapies for treating subjects. For example, a subject can provide a tissue sample (e.g., a tumor biopsy or a blood sample) before and/or after treatment with a TRP antagonist and the sample can be examined by way of various in vitro assays to determine whether the subject's cells are sensitive to a TRP antagonist, such as a TRPA1 antagonist.

The invention also provides methods for monitoring the sensitivity or responsiveness of a subject to a TRP antagonist (e.g., a TRPA1 antagonist). The methods may be conducted in a variety of assay formats, including assays detecting genetic or protein expression (such as PCR and enzyme immunoassays) and biochemical assays detecting appropriate activity. Determination of expression or the presence of such biomarkers in subject samples is predictive of whether a subject is sensitive to the biological effects of a TRP antagonist, such as a TRPA1 antagonist. Applicants' invention herein is that a difference or change (i.e., an increase or decrease) in the expression of the 1, 2, 3, 4, 5, 6, 7, 8, 9, 10, 11, 12, 13, 14, 15, 16, 17, 18, 19, 20, 21, 22, 23, 24, 25, 26, 27, or 28 of the genes listed in Table 1 in a sample from a subject having a cancer relative to a reference level (including, e.g., the median expression level of the biomarker in a sample from a group/population of subjects being tested for responsiveness to a TRP antagonist or the median expression level of the biomarker in a sample from a group/population of subjects having cancers and identified as not responding to TRP antagonist treatment) correlates with treatment of such a subject with a TRP antagonist, such as a TRPA1 antagonist.

In some embodiments, the reference expression level is the median level of expression of the at least one gene in subjects having glioblastomas and identified as not responding to TRP antagonist (e.g., a TRPA1 antagonist) treatment. In some embodiments, the reference expression level is the expression level of the at least one gene in a sample previously obtained from the individual at a prior time. In other embodiments, the individuals are subjects who received prior treatment with a TRP antagonist in a primary tumor setting. In some embodiments, the individuals are subjects who are experiencing metastasis. Individuals who have an expression level that is greater than or less than the reference expression level of at least one biomarker gene as described herein are identified as subjects likely to respond to treatment with a TRP antagonist. Subjects who exhibit gene expression levels at, for example, 50%, 45%, 40%, 35%, 30%, 25%, 20%, 15%, 10%, or 5% relative to (i.e., higher or lower than) the median are identified as subjects likely to respond to treatment with a TRP antagonist (e.g., a TRPA1 antagonist). The subjects may be informed that they have an increased likelihood of being responsive to treatment with a TRP antagonist and/or provided a recommendation that anti-cancer therapy include a TRP antagonist. The gene expression level can be determined using at least one of the biomarker genes as described herein, or any linear combination of the biomarker genes as described herein (e.g., mean, weighted mean, or median) using methods known in the art.

Those of skill in the medical arts, particularly pertaining to the application of diagnostic tests and treatment with therapeutics, will recognize that biological systems are somewhat variable and not always entirely predictable, and thus many good diagnostic tests or therapeutics are occasionally ineffective. Thus, it is ultimately up to the judgment of the attending physician to determine the most appropriate course of treatment for an individual subject, based upon test results, subject condition and history, and his or her own experience. There may even be occasions, for example, when a physician will choose to treat a subject with a TRP antagonist, such as a TRPA1 antagonist, even when a subject is not predicted to be particularly sensitive to TRPA1 antagonists, based on data from diagnostic tests or from other criteria, particularly if all or most of the other obvious treatment options have failed, or if some synergy is anticipated when given with another treatment.

In further expressed embodiments, the present invention provides a method of predicting the sensitivity of a subject to treatment with a TRP antagonist, such as a TRPA1 antagonist, or predicting whether a subject will respond effectively to treatment with a TRP antagonist, comprising assessing the level of one or more of the genetic biomarkers identified herein expressed in the sample; and predicting the sensitivity of the subject to inhibition by a TRP antagonist, wherein expression levels of one or more of these genetic biomarkers correlates with high sensitivity of the subject to effective response to treatment with a TRP antagonist.

The sample may be taken from a subject who is suspected of having, or is diagnosed as having a cancer, and hence is likely in need of treatment, or from a normal individual who is not suspected of having any disorder. For assessment of marker expression, subject samples, such as those containing cells, or proteins or nucleic acids produced by these cells, may be used in the methods of the present invention. In the methods of this invention, the level of a biomarker can be determined by assessing the amount (e.g., the absolute amount or concentration) of the markers in a sample, preferably a tissue sample (e.g., a tumor tissue sample, such as a biopsy). In addition, the level of a biomarker can be assessed in bodily fluids or excretions containing detectable levels of biomarkers. Bodily fluids or secretions useful as samples in the present invention include, e.g., blood, urine, saliva, stool, pleural fluid, lymphatic fluid, sputum, ascites, prostatic fluid, cerebrospinal fluid (CSF), or any other bodily secretion or derivative thereof. The word "blood" is meant to include whole blood, plasma, serum, or any derivative of blood. Assessment of a biomarker in such bodily fluids or excretions can sometimes be preferred in circumstances where an invasive sampling method is inappropriate or inconvenient. However, in the case of samples that are bodily fluids, the sample to be tested herein is preferably blood, synovial tissue, or synovial fluid, most preferably blood.

The sample may be frozen, fresh, fixed (e.g., formalin fixed), centrifuged, and/or embedded (e.g., paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

In any of the methods described herein, the subject may be informed of an higher or lower likelihood of being sensitive or responsive to treatment with a TRP antagonist (e.g., a TRPA1 antagonist); provided a recommendation of an anti-cancer therapy (e.g., an anti-cancer therapy that includes or does not include a TRP antagonist); and/or selected a suitable therapy (e.g., a TRP antagonist and/or other anti-cancer agent).

A. Detection of Gene Expression

The genetic biomarkers described herein can be detected using any method known in the art. For example, tissue or cell samples from mammals can be conveniently assayed for, e.g., mRNAs or DNAs from a genetic biomarker of interest using Northern, dot-blot, or polymerase chain reaction (PCR) analysis, array hybridization, RNase protection assay, or using DNA SNP chip microarrays, which are commercially available, including DNA microarray snapshots. For example, real-time PCR (RT-PCR) assays such as quantitative PCR assays are well known in the art. In an illustrative embodiment of the invention, a method for detecting mRNA from a genetic biomarker of interest in a biological sample, such as a tumor sample (e.g., a glioblastoma tumor sample), comprises producing cDNA from the sample by reverse transcription using at least one primer; amplifying the cDNA so produced; and detecting the presence of the amplified cDNA. In addition, such methods can include one or more steps that allow one to determine the levels of mRNA in a biological sample (e.g., by simultaneously examining the levels a comparative control mRNA sequence of a "housekeeping" gene such as an actin family member). Optionally, the sequence of the amplified cDNA can be determined.

1. Detection of Nucleic Acids

In one specific embodiment, expression of the biomarker genes as described herein can be performed by RT-PCR technology. Probes used for PCR may be labeled with a detectable marker, such as, for example, a radioisotope, fluorescent compound, bioluminescent compound, a chemiluminescent compound, metal chelator, or enzyme. Such probes and primers can be used to detect the presence of expressed genes set forth in Table 1 in a sample. As will be understood by the skilled artisan, a great many different primers and probes may be prepared and used effectively to amplify, clone and/or determine the presence and/or levels expressed of one or more of the genes listed in Table 1.

Other methods include protocols that examine or detect mRNAs from at least one of the genes listed in Table 1 (e.g., 1, 2, 3, 4, 5, 6, 7, 8, 9, 10, 11, 12, 13, 14, 15, 16, 17, 18, 19, 20, 21, 22, 23, 24, 25, 26, 27, or 28 of the genes listed in Table 1) in a tissue (e.g., a tumor tissue) or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment.

In addition, the DNA profiling and detection method utilizing microarrays may be employed. This method rapidly identifies and distinguishes between different DNA sequences utilizing short tandem repeat (STR) analysis and DNA microarrays. In an embodiment, a labeled STR target sequence is hybridized to a DNA microarray carrying complementary probes. These probes vary in length to cover the range of possible STRs. The labeled single-stranded regions of the DNA hybrids are selectively removed from the microarray surface utilizing a post-hybridization enzymatic digestion. The number of repeats in the unknown target is deduced based on the pattern of target DNA that remains hybridized to the microarray.

One example of a microarray processor is the Affymetrix GENECHIP® system, which is commercially available and comprises arrays fabricated by direct synthesis of oligonucleotides on a glass surface. Other systems may be used as known to one skilled in the art.

Other methods for determining the level of the biomarker besides RT-PCR or another PCR-based method include proteomics techniques, as well as individualized genetic profiles that are necessary to treat cancer based on subject response at a molecular level. The specialized microarrays herein, e.g., oligonucleotide microarrays or cDNA microarrays, may comprise one or more biomarkers having expression profiles that correlate with either sensitivity or resistance to one or more TRP antagonists. Other methods that can be used to detect nucleic acids, for use in the invention, involve high throughput RNA sequence expression analysis, including RNA-based genomic analysis, such as, for example, RNASeq.

2. Detection of Proteins

As to detection of protein biomarkers such as a protein biomarker corresponding to at least one of the genes listed in Table 1 (e.g., 1, 2, 3, 4, 5, 6, 7, 8, 9, 10, 11, 12, 13, 14, 15, 16, 17, 18, 19, 20, 21, 22, 23, 24, 25, 26, 27, or 28 of the genes listed in Table 1), for example, various protein assays are available including, for example, antibody-based methods as well as mass spectroscopy and other similar means known in the art. In the case of antibody-based methods, for example, the sample may be contacted with an antibody specific for said biomarker under conditions sufficient for an antibody-biomarker complex to form, and then detecting said complex. Detection of the presence of the protein biomarker may be accomplished in a number of ways, such as by western blotting (with or without immunoprecipitation), 2-dimensional SDS-PAGE, immunoprecipitation, fluorescence activated cell sorting (FACS), flow cytometry, and ELISA procedures for assaying a wide variety of tissues and samples, including plasma or serum. A wide range of immunoassay techniques using such an assay format are available, including both single-site and two-site or "sandwich" assays of the non-competitive types, as well as in the traditional competitive binding assays. These assays also include direct binding of a labeled antibody to a target biomarker.

Treatment with the TRP Antagonist

A. Dosage and Administration

Once a subject responsive or sensitive to treatment with a TRP antagonist (e.g., a TRPA1 antagonist) as described herein has been identified, treatment with the TRP antagonist, alone or in combination with other medicaments, can be carried out. Such treatment may result in, for example, a reduction in tumor size (e.g., glioblastoma tumor size) or an increase in progression free survival (PFS) and/or overall survival (OS). Moreover, treatment with the combination of a TRP antagonist (e.g., a TRPA1 antagonist) and at least one second medicament(s) preferably results in an additive, more preferably synergistic (or greater than additive), therapeutic benefit to the subject. Preferably, in this combination method the timing between at least one administration of the second medicament and at least one administration of the antagonist herein is about one month or less, more preferably, about two weeks or less.

It will be appreciated by those of skill in the medical arts that the exact manner of administering a therapeutically effective amount of a TRP antagonist (e.g., a TRPA1 antagonist) to a subject following diagnosis of their likely responsiveness to the TRP antagonist will be at the discretion of the attending physician. The mode of administration, including dosage, combination with other agents, timing and frequency of administration, and the like, may be affected by the diagnosis of a subject's likely responsiveness to such TRP antagonist, as well as the subject's condition and history. Thus, even subjects having cancers who are predicted to be relatively insensitive to a TRP antagonist may still benefit from treatment therewith, particularly in combination with other agents, including agents that may alter a subject's responsiveness to the antagonist.

A composition comprising a TRP antagonist will be formulated, dosed, and administered in a fashion consistent with good medical practice. Factors for consideration in this context include the particular type of cancer being treated (e.g., a newly diagnosed cancer or a recurrent cancer), the particular mammal being treated (e.g., human), the clinical condition of the individual subject, the cause of the cancer, the site of delivery of the agent, possible side-effects, the type of antagonist, the method of administration, the scheduling of administration, and other factors known to medical practitioners. The effective amount of the TRP antagonist to be administered will be governed by such considerations.

A physician having ordinary skill in the art can readily determine and prescribe the effective amount of the pharmaceutical composition required, depending on such factors as the particular antagonist type. For example, the physician could start with doses of such a TRP antagonist (e.g., a TRPA1 antagonist), employed in the pharmaceutical composition at levels lower than that required in order to achieve the desired therapeutic effect and gradually increase the dosage until the desired effect is achieved. The effectiveness of a given dose or treatment regimen of the antagonist can be determined, for example, by assessing signs and symptoms in the subject using standard measures of efficacy.

In certain examples, the subject is treated with the same TRP antagonist (e.g., a TRPA1 antagonist) at least twice. Thus, the initial and second TRP antagonist exposures are preferably with the same antagonist, and more preferably all TRP antagonist exposures are with the same TRP antagonist, i.e., treatment for the first two exposures, and preferably all exposures, is with one type of TRP antagonist, for example, an antagonist that binds to TRP, such as a TRPA1 antagonist.

As a general proposition, the effective amount of the TRP antagonist administered parenterally per dose will be in the range of about 20 mg to about 5000 mg, by one or more dosages. Dosage regimens for antibodies, such as TRP antagonists (e.g., a TRPA1 antagonist), include 100 or 400 mg every 1, 2, 3, or 4 weeks or is administered a dose of about 1, 3, 5, 10, 15, or 20 mg/kg every 1, 2, 3, or 4 weeks. For example, an effective amount of a TRP antagonist (e.g., a TRPA1 antagonist) can be administered at 10 mg/kg every two weeks, optionally, by intravenous (i.v.) administration. In another example, an effective amount of a TRP antagonist (e.g., a TRPA1 antagonist) can be administered at 15 mg/kg every three weeks, optionally, by i.v. administration. The dose may be administered as a single dose or as multiple doses (e.g., 2 or 3 doses), such as infusions.

In some instances, depending on the type and severity of the disease, about 1 µg/kg to 100 mg/kg (e.g., 0.1-20 mg/kg) of the TRP antagonist (e.g., a TRPA1 antagonist) as an initial candidate dosage for administration to the subject, whether, for example, by one or more separate administrations, or by continuous infusion. In one embodiment, desirable dosages include, for example, 6 mg/kg, 8 mg/kg, 10 mg/kg, and 15 mg/kg. For repeated administrations or cycles over several days or longer, depending on the condition, the treatment is sustained until the cancer is treated, as measured by the methods described above or known in the art. However, other dosage regimens may be useful. In one example, the TRP antagonist is administered once every week, every two weeks, or every three weeks, at a dose range from about 6 mg/kg to about 15 mg/kg, including but not limited to 6 mg/kg, 8 mg/kg, 10 mg/kg or 15 mg/kg. The progress of the therapy of the invention is easily monitored by conventional techniques and assays. In other embodiments, such dosing regimen is used in combination with a chemotherapy regimen in glioblastoma.

If multiple exposures of TRP antagonist are provided, each exposure may be provided using the same or a different administration means. In one embodiment, each exposure is by intravenous administration. In another embodiment, each exposure is given by subcutaneous administration. In yet another embodiment, the exposures are given by both intravenous and subcutaneous administration.

The duration of therapy can be continued for as long as medically indicated or until a desired therapeutic effect (e.g., those described herein) is achieved. In certain embodiments, the therapy is continued for 1 month, 2 months, 4 months, 6 months, 8 months, 10 months, 1 year, 2 years, 3 years, 4 years, 5 years, or for a period of years up to the lifetime of the subject.

As noted above, however, these suggested amounts of TRP antagonist are subject to a great deal of therapeutic discretion. The key factor in selecting an appropriate dose and scheduling is the result obtained, as indicated above. In some embodiments, the TRP antagonist is administered as close to the first sign, diagnosis, appearance, or occurrence of the cancer as possible.

1. Routes of Administration

The TRP antagonist (e.g., a TRPA1 antagonist) can be administered by any suitable means, including peroral, parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated. In addition, the TRP antagonist may suitably be administered by pulse infusion, e.g., with declining doses of the TRP antagonist. Most preferably, the dosing is given by intravenous injections.

If multiple exposures of TRP antagonist are provided, each exposure may be provided using the same or a different administration means. In one embodiment, each exposure is by i.v) administration. For example, a TRP antagonist (e.g., a TRPA1 antagonist), can be infused through a dedicated line. For example, a TRP antagonist (e.g., a TRPA1 antagonist), can be administered initially intravenously over about 90 minutes, with subsequent infusions over about 60 minutes and then about 30 minutes. In another embodiment, each exposure is given by subcutaneous (s.c.) administration. In yet another embodiment, the exposures are given by both i.v. and s.c. administration.

2. Combination Therapy

In some embodiments, a TRP antagonist (e.g., a TRPA1 antagonist) may be used in combination with one or more additional anti-cancer agents or therapies. Examples of anti-cancer therapies include, without limitation, surgery, radiation therapy (radiotherapy), biotherapy, chemotherapy, or a combination of these therapies. In addition, cytotoxic agents, anti-angiogenic and anti-proliferative agents can be used in combination with the TRP antagonist. The one or more additional anti-cancer agents or therapies preferably have complementary activities to the TRP antagonist such that they do not adversely affect each other. The combined administration includes co-administration, using separate formulations or a single pharmaceutical formulation, and consecutive administration in either order, wherein preferably there is a time period while both (or all) active agents simultaneously exert their biological activities.

The one or more additional anti-cancer agents may be a chemotherapeutic agent, a cytotoxic agent, a cytokine, a growth inhibitory agent, an anti-hormonal agent, and combinations thereof. Such molecules are suitably present in combination in amounts that are effective for the purpose intended. A pharmaceutical composition containing a TRP antagonist (e.g., a TRPA1 antagonist) may also comprise a therapeutically effective amount of an anti-cancer agent.

Other therapeutic regimens in accordance with this invention may include administration of an anti-cancer agent and, including without limitation radiation therapy and/or bone marrow and peripheral blood transplants, and/or a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (ONCOVIN™) prednisolone, CHOP, CVP, or COP. In another embodiment, the combination includes docetaxel, doxorubicin, and cyclophosphamide. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with a TRP antagonist (e.g., a TRPA1 antagonist) involves the combined administration of an anti-cancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner.

Suitable dosages for any of the above co-administered agents are those presently used and may be lowered due to the combined action (synergy) of the TRP antagonist and other chemotherapeutic agents or treatments.

The combination therapy may provide "synergy" and prove "synergistic," i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In general, for the prevention or treatment of disease, the appropriate dosage of the additional therapeutic agent will depend on the type of disease to be treated, the type of antibody, the severity and course of the disease, whether the TRP antagonist (e.g., a TRPA1 antagonist) and additional agent are administered for preventive or therapeutic purposes, previous therapy, the subject's clinical history and response to the TRP antagonist and additional agent, and the discretion of the attending physician. The TRP antagonist and additional agent are suitably administered to the subject at one time or over a series of treatments. The TRP antagonist is typically administered as set forth above. Depending on the type and severity of the disease, about 20 mg/m$^2$ to 600 mg/m$^2$ of the additional agent is an initial candidate dosage for administration to the subject, whether, for example, by one or more separate administrations, or by continuous infusion. One typical daily dosage might range from about or about 20 mg/m$^2$, 85 mg/m$^2$, 90 mg/m$^2$, 125 mg/m$^2$, 200 mg/m$^2$, 400 mg/m$^2$, 500 mg/m$^2$ or more, depending on the factors mentioned above. For repeated administrations over several days or longer, depending on the condition, the treatment is sustained until a desired suppression of disease symptoms occurs. Thus, one or more doses of about 20 mg/m$^2$, 85 mg/m$^2$, 90 mg/m$^2$, 125 mg/m$^2$, 200 mg/m$^2$, 400 mg/m$^2$, 500 mg/m$^2$, 600 mg/m$^2$ (or any combination thereof) may be administered to the subject. Such doses may be administered intermittently, e.g., every week or every two, three weeks, four, five, or six (e.g., such that the subject receives from about two to about twenty, e.g., about six doses of the additional agent). An initial higher loading dose, followed by one or more lower doses may be administered. However, other dosage regimens may be useful. The progress of this therapy is easily monitored by conventional techniques and assays.

In one embodiment, the subject has never been previously administered any drug(s) to treat cancer. In another embodiment, the subject has been previously administered one or more medicaments(s) to treat cancer. In a further embodiment, the subject was not responsive to one or more of the medicaments that had been previously administered. Such drugs to which the subject may be non-responsive include, for example, anti-neoplastic agents, chemotherapeutic agents, ROS-inducing agents, cytotoxic agents, and/or growth inhibitory agents. More particularly, the drugs to which the subject may be non-responsive include TRP antagonists (e.g., a TRPA1 antagonist).

3. Pharmaceutical Formulations

Therapeutic formulations of the antagonists used in accordance with the present invention are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Remington's The Science and Practice of Pharmacy (22nd edition), ed. L. Allen, Jr., 2012, Pharmaceutical Press, London, UK.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's The Science and Practice of Pharmacy (22nd edition), ed. L. Allen, Jr., 2012, Pharmaceutical Press, London, UK.

Cancers

The terms "cancer" and "cancerous" refer to or describe the physiological condition in mammals that is typically characterized by unregulated cell growth. Included in this definition are benign and malignant cancers as well as dormant tumors or micrometastases. Cancers include but are not limited to, carcinoma, adenocarcinomas, lymphoma, blastoma, sarcoma, and leukemia. Other cancers include, for example, including colon cancers, rectal cancer, renal-cell carcinoma, liver cancer, non-small cell carcinoma of the lung, cancer of the small intestine and cancer of the esophagus, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of the cancers.

Cancer Treatments

In the invention, chemotherapeutic agents representing the standard-of-care, as known to those of skill in the art and to a physician treating a subject with cancer, may be administered to the subject in combination with a TRP channel antagonist, as determined by the method of the invention. Chemotherapeutic agents include alkylating agents, such as, for example, temozolomide (TMZ), the imidazotetrazine derivative of the alkylating agent dacarbazine. Additional examples of chemotherapeutics agents include, e.g., paclitaxel or topotecan or pegylated liposomal doxorubicin (PLD). Other examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin; bryostatin; callystatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, calicheamicin gammal I, and calicheamicin omegal1); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chlorambucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Examples of ROS-inducing agents include phenethylisothiocyanate (PEITC), parthenolide, piperlongumine, erastin, lanperisone, Aminoflavone (5-amino-2-(4-amino-3-fluoro-phenyl(-6,8-difluoro-7-methylchromen-4-one), combination therapy of gemcitabine with trichostatin A, and benzyl isothiocyanate (BITC).

Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, and ara-C. Further information can be found in The Molecular Basis of Cancer, (Mendelsohn et al. The Molecular Basis of Cancer E-Book. Elsevier Health Sciences, 2014) and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

Examples of cancer type(s) that would be susceptible to treatment with combinations of anti-cancer agents combined with TRP antagonists are listed in Table 2 (based on National Cancer Institute (www.cancer.gov/) cancer treatment listings).

TABLE 2

Anti-Cancer Agents for Various Cancer Types

| Anti-cancer agent combined with TRP antagonist | Cancer type(s) |
| --- | --- |
| Doxorubicin | Acute lymphoblastic leukemia (ALL). Acute myeloid leukemia (AML). Breast cancer. Gastric cancer. Hodgkin lymphoma. Neuroblastoma. Non-Hodgkin lymphoma. Ovarian cancer. Small cell lung cancer. Soft tissue and bone sarcomas. Thyroid cancer. Transitional cell bladder cancer. Wilms tumor. |
| Gemcitabine | Breast cancer. Non-small cell lung cancer (NSCLC). Ovarian cancer. Pancreatic cancer. |
| Gemcitabine + Paclitaxel | Breast cancer. Pancreatic cancer. |
| Gemcitabine + Cisplatin | NSCLC. |
| Gemcitabine + Carboplatin | Ovarian cancer. |
| Tamoxifen | Breast cancer. |
| Methotrexate | ALL. Breast cancer. Gestational trophoblastic disease. Head and neck cancer. Lung cancer. Mycosis fungoides. Non-Hodgkin lymphoma. Osteosarcoma. |
| Arsenic trioxide | Acute promyelocytic leukemia. |
| Anastrozole | Breast cancer in postmenopausal women who have any of the following types of breast cancer: Early-stage, hormone receptor positive (HR+) breast cancer. Locally advanced or metastatic breast cancer that is HR+ or hormone receptor unknown (it is not known whether it is HR+ or hormone receptor negative). Advanced breast cancer that has gotten worse after treatment with tamoxifen citrate. |
| Exemestane | Breast cancer (e.g., that is advanced or that is early-stage and estrogen receptor positive). |
| Letrozole | Breast cancer in postmenopausal women who have any of the following types of breast cancer: Early-stage, hormone receptor positive (HR+) breast cancer in women who have already received other treatment. Early-stage breast cancer that has been treated with tamoxifen citrate for at least five years. Breast cancer that is locally advanced or has metastasized, is HER2 positive (HER2+) and HR+. Breast cancer that is locally advanced or has metastasized and it is not known whether the cancer is HR+ or hormone receptor negative (HR−). Advanced breast cancer that has gotten worse after antiestrogen therapy. |
| Formestane | Breast cancer (e.g., that is estrogen receptor positive). |
| Fadrozole | Breast cancer. |
| Cisplatin | Bladder cancer (e.g., that cannot be treated with surgery or radiation therapy). Ovarian cancer (e.g., that has metastasized). Testicular cancer (e.g., that has metastasized in patients who have already had surgery or radiation therapy). |
| Carboplatin | Ovarian cancer that is advanced. It is used with other chemotherapy as first-line treatment. It is used alone as palliative treatment for disease that has recurred (come back) after earlier chemotherapy. |
| Oxaliplatin | Colorectal cancer (e.g., that is advanced or has recurred). Colon cancer. |
| Nedaplatin (see, e.g., Shimada et al, Cancer Manag. Res. 8: 67-76, 2013) | Squamous cell lung cancer. NSCLC. Esophageal cancer. Uterine cervical cancer. Head and neck cancer. Urothelial cancer. |

TABLE 2-continued

Anti-Cancer Agents for Various Cancer Types

| Anti-cancer agent combined with TRP antagonist | Cancer type(s) |
|---|---|
| Triplatin tetranitrate (see, e.g., Wheate et al, Dalton Trans, 39: 8113-8127, 2010) | Ovarian cancer. Small cell lung cancer. Gastric cancer. |
| Phenanthriplatin | Leukemias. NSCLC. Colon cancer. Central nervous system cancers. Melanoma. Ovarian cancer. Renal cancer. Prostate cancer. Breast cancer. |
| Picoplatin | Lung cancer. Ovarian cancer. Colorectal cancer. Hormone-refractory prostate cancer. |
| Satraplatin | Prostate cancer. Lung cancer. Ovarian cancer. |

EXAMPLES

The following examples are provided to illustrate, but not to limit the presently claimed invention.

Example 1: Materials and Methods

Animals and In Vivo Procedures

All animal studies were performed according to protocols approved by the Institutional Animal Care and Use Committee, the Standing Committee on Animals at Harvard University. One million HCC1569 cells stably expressing either TRPA1 or GFP (control) shRNAs were injected into cleared mammary fatpads of 8-week-old female NOD-Rag1$^{null}$ IL2rg$^{null}$ (NRG) mice. Tumor volume (mm$^3$) was monitored by caliper measurements in two perpendicular dimensions (the formula: (d$^2$×D)/2, where d and D represent the shortest and longest diameters, respectively) at the indicated time points. After tumors reached 3 to 5 mm in diameter, animals were randomized into the following treatment arms: (i) 37.5 mg/kg carboplatin or (ii) its vehicle (H$_2$O) administered via intraperitoneal injection for HCC1569 cell-transplanted animals; (i) oral administration of 30.0 mg/kg AM-0902, (ii) intraperitoneal administration of 37.5 mg/kg carboplatin, (iii) oral administration of 30.0 mg/kg AM-0902 plus intraperitoneal administration of 37.5 mg/kg carboplatin, or (iv) oral administration of 1% Tween 80/2% HPMC/97% water/methanesulfonic acid pH 2.2 (vehicle for AM-0902) plus intraperitoneal administration of H$_2$O (vehicle for carboplatin) for EL-12-58 cell-transplanted animals. Power calculations are based on the standard deviation and effect size from pilot experiments in HCC1569 cells. The sample size of seven mice per group provides greater than 95% power to detect a ~80% difference in change in tumor volume between control and shTRPA1-treated cells with a two-sided type I error rate of 5%. Averaged tumor volume represents mean±SEM.

Development of Subject Derived HCl-002 Cell Line

Subject-derived xenograft HCl-002 was expanded in mammary fat pads of NOD-SCID mice to 1 cm diameter (DeRose et al., Nat. Med., 17:1514-1520, 2011). Tumors were mechanically dissociated then digested with collagenase/hyaluoronidase (Stem Cell Technologies) followed by TrypLE Express (Thermo Fisher Scientific) with DNase (Roche Diagnostics). The resultant organoid suspension was plated in conditioned media from irradiated J2 3T3 fibroblasts with Rho kinase inhibitor as previously described. Contaminating fibroblasts were minimized by a combined approach of differential trypsinization and differential adhesion over passages 1-3 with a highly pure human epithelial population (>95% EPCAM-positive by FACS). The cell culture remained phenotypically stable over multiple passages and recapitulated the histologic appearance of the parent subject-derived xenograft upon orthotopic implantation into mammary fat pads of immunocompromised mice. Early-passage cultures (passage 4-8) were used for all experiments.

Cell Culture

MCF-10A cells were cultured in DMEM/F12 (Life Technologies) supplemented with 5% horse serum, 20 ng/ml epidermal growth factor (EGF), 10 µg/ml insulin, 0.5 µg/mL hydrocortisone, 100 ng/mL cholera toxin, and penicillin and streptomycin (P/S) (Life Technologies). HCC1569, HCC38, HCC202, HCC70, HCC1500, MDAMB-175, T47D, BT-549, H1792, H647, A549, and H23 cells were cultured in RPMI (Life Technologies)+10% fetal bovine serum (FBS) (Life Technologies) with P/S (Life Technologies). HLF-a cells were cultured in Eagle's Minimum Essential Medium (ATCC)+10% FBS with P/S. sNF96.2, 90-BTL, 88-14, and S462 cells were cultured in Dulbecco's Modified Eagle Medium (DMEM; Life Technology)+10% FBS with P/S, 1 mM sodium pyruvate (Thermo Fisher Scientific), and 2 mM L-glutamine (Thermo Fisher Scientific). EL-12-58 and HCl-002 cells were cultured in F-12 (Lonza)/DMEM (3:1 mixture)+5% FBS with P/S, hydrocortisone (0.4 µg/mL, Sigma), cholera toxin (8.4 ng/mL, Sigma), insulin (5 µg/mL, Sigma), EGF (10 ng/mL, PeproTech), and Y-27632 (5 µM, ENZO life sciences). All cells were routinely cultured in 37° C. with 5% CO$_2$. For 3D culture, MCF-10A cells were plated on Matrigel-coated glass bottom 24-well plates in DMEM/F12 (Life Technologies), 2% horse serum (Life Technologies), EGF (5 ng/mL), hydrocortisone (0.5 µg/mL), cholera toxin (100 ng/mL), insulin (10 µg/mL), and P/S supplemented with 2% Growth Factor Reduced Matrigel (BD Biosciences). HCC1569 cells were plated on Matrigel-coated glass bottom 24-well plates in the regular HCC1569 growth media supplemented with 2% Growth Factor Reduced Matrigel (BD Biosciences). The cells were refed with fresh media every three days. For suspension culture, MCF-10A and HCC1569 cells were plated on poly HEMA (poly-2-hydroxyethyl methacrylate, Sigma)-coated plates in the regular MCF-10A or HCC1569 growth media. In 3D and suspension culture, cells were maintained in 37° C. with 5% $CO_2$ and 6% $O_2$ (physiological partial pressure of $O_2$).

Immunohistochemistry Staining

Unstained breast cancer and normal breast tissue arrays were purchased from US Biomax (BR1504a for breast tumors, BN08111 for normal breast tissues). Formalin-fixed tumor samples derived from mouse xenografts were processed and embedded in paraffin. Tissue sections were deparaffinized and antigen retrieval was achieved by use of heat-induced epitope retrieval with pH 6.0 citrate buffer (Sigma). Tissue sections were stained with hematoxylin and eosin (H&E), anti-TRPA1 antibody (Sigma), or anti-Cleaved Caspase-3 (Asp175) antibody (Cell Signaling). TRPA1 antibody was validated using sections from tumors that expressed TRPA1 shRNA vectors. Immunostained slides were counterstained with hematoxylin (Sigma). Tumor slides stained for TRPA1, blinded and were evaluated by light microscopy and scored by a veterinary pathologist. Images of tissue sections were captured at 4× magnification to create a merged image of the entire section and at 20× magnification for quantification of cleaved caspase-3-positive nuclei, using a Olympus VS120 Slide Scanner. Images of tumor sections stained with H&E or cleaved caspase-3 are representative of two independent experiments. Relative apoptosis was quantified by determining the percentage of cleaved caspase-3-positive cells from more than five random fields, per section, from each tumor in the group, and normalized to the shGFP-expressing tumors treated with vehicle. Data is mean±SEM from the sum of two independent experiments.

Plasmids, siRNAs, shRNAs, and Virus Production

The pC1-HyPer-2 (Cat #42211) and pC1-HyPer-C199S (Cat #42213) plasmids were obtained by Addgene. The lentiviral constructs of pCDH (Puro or Hygromycin B)-HyPer-2 and pCDH (Puro or Hygromycin B)-HyPer-C199S were conducted by transferring the NheI and BamHI digested fragments of HyPer-2 and HyPer-C199S from the pC1 constructs into the NheI and BamHI digested pCDH (Puro or Hygromycin B) vector. pENTR223.1-TRPA1 was purchased from GE Healthcare and cloned into a Gateway compatible pLX304 vector. LentiCRISPR plasmids were constructed using lentiCRISPRv2 containing two expression cassettes, hSpCas9 and the chimeric guide RNA. Design of gRNAs and off-target sites prediction were performed by using the Zhang laboratory CRISPR design tool (crispr.mit.edu). TRPA1 mutants were constructed according to standard Quickchange protocol. Primers used for the construction are shown in Table 3. The nucleotide sequences of the mutants were verified by sequencing the corresponding cDNA. TRPA1 shRNAs were acquired from the RNAi Consortium, and have 100% sequence homology for TRPA1 (shRNA #1 is TRCN0000044801 and shRNA #2 is TRCN0000434290). shRNA against GFP was purchased from Addgene (plasmid #: 30323). Lentiviruses for shRNAs against TRPA1 or GFP and plasmids for TRPA1 or Hyper-2 constructs were made in 293T cells according to standard protocol and selected with Blasticidin, Puromycin, or Hygromycin B for at least 1 week. SMARTpool siRNA for Pyk2 (L-003165-00), NFE2L2 (L-003755-00), and siGENOME Non-Targeting siRNA Pool #2 (D-001206-14) were purchased from GE Healthcare and was transfected according to standard protocol and experiments were performed within 48-72 h of transfection. MCF-10A cells expressing HER2 were generated as described previously (Schafer et al., Nature, 461:109-113, 2009).

TABLE 3

Primer Sequences Used for the Construction of TRPA1 Mutants

| Genes | Mutants | Mutation primer sequences (5'→3') |
|---|---|---|
| TRPA1 | L259P | for: GATCAAAATGTGCCCGGACAATGGTGC (SEQ ID NO: 1)<br>rev: GCACCATTGTCCGGGCACATTTTGATC (SEQ ID NO: 2) |
| | S296F | for: CTGATGATATCGTCCTATTTTGGTAGCGTGG (SEQ ID NO: 3)<br>rev: CCACGCTACCAAAATAGGACGATATCATCAG (SEQ ID NO: 4) |
| | N431S | for: CTGGTTCTGTAAATTCCCTACTTGGCTTTAATGTGTCC (SEQ ID NO: 5)<br>rev: GGACACATTAAAGCCAAGTAGGGAATTTACAGAACCAG (SEQ ID NO: 6) |
| | K491N | for: CCATCTGGCAGCAAACAATGGACATG (SEQ ID NO: 7)<br>rev: CATGTCCATTGTTTGCTGCCAGATGG (SEQ ID NO: 8) |
| | G505S | for: CAGCTTCTTCTGAAAAAATCTGCATTGTTTCTCAGTG (SEQ ID NO: 9)<br>rev: CACTGAGAAACAATGCAGATTTTTTCAGAAGAAGCTG (SEQ ID NO: 10) |
| | E681K | for: CACCTACACAGGATGTTATATATAAACCGCTTACAGCCCTC (SEQ ID NO: 11)<br>rev: GAGGGCTGTAAGCGGTTTATATATAACATCCTGTGTAGGTG (SEQ ID NO: 12) |
| | K771Q | for: CCACGAATTCATATCTAATACAAACTTGTATGATTTTAGTG (SEQ ID NO: 13)<br>rev: CACTAAAATCATACAAGTTTGTATTAGATATGAATTCGTGG (SEQ ID NO: 14) | for: forward primer;
rev: reverse primer $H_2O_2$ Measurement

For the measurement of $[H_2O_2]_i$ levels in MCF-10A acini and HCC1569 spheroids, cells were transduced with a lentiviral vector encoding Hyper-2 or Hyper-2 (C199S). The Hyper-2 fluorescence was measured at 37° C. in HEPES-buffered saline (HBS) containing the following (in mM): 150 NaCl, 6 KCl, 1.2 $MgSO_4$, 2 $CaCl_2$, 11.5 glucose, and 25 HEPES (pH adjusted to 7.4 with NaOH). Fluorescence images of the cells were acquired through the Eclipse Ti-E microscope (Nikon) with ORCA-R2 cooled CCD camera (Hamamatsu Photonics) and analyzed with Metafluor image acquisition software (Molecular Devices). The 488:405-nm ratio images were obtained on a pixel-by-pixel basis. 3D images are shown as one section from midstructure. For the measurement of $[H_2O_2]_i$ levels in MCF-10A cells cultured in suspension, cell clumps were dissociated with trypsin and stained with 10 μM peroxy green-1 for 30 min at 37° C. Cells were then subjected to flow cytometric analysis (FACSCalibur; BD Biosciences). ROS levels determined by flow cytometry are reported as mean fluorescence intensity expressed in arbitrary units. Hyper-2 ratio images are representative from two independent experiments and averaged Hyper-2 ratio represents mean±SD from the sum of two independent experiments.

$Ca^{2+}$ Measurement

For the measurement of $[Ca^{2+}]_i$ levels in cells cultured in 2D or 3D (in Matrigel), cells were stained with 3.5 μM fura-2-AM (Life Technology) in the presence of 2.5 mM probenecid (Sigma) and 0.02% Pluronic F-127 (Sigma) for 45 min at 37° C. The fura-2 fluorescence was measured in HBS solution containing 1.25 mM probenecid at 37° C. Fluorescence images of the cells were acquired through the Eclipse Ti-E microscope with ORCA-R2 cooled CCD camera and analyzed with Metafluor. The 340:380-nm ratio images were obtained on a pixel-by-pixel basis and were converted to $Ca^{2+}$ concentrations by in vivo calibration using 5 µM ionomycin as described previously (Nishida et al., Biochem. Biophys. Res. Commun., 262:350-354, 1999). 3D images are shown as one section from midstructure. For the measurement of $[Ca^{2+}]_i$ levels in cells cultured in suspension, cell clumps were dissociated with trypsin and $[Ca^{2+}]_i$ levels were determined by using Fluo-4 NW Calcium Assay Kit (Molecular Probes). Cells were stained with Fluo-4 according to the manufacturer's instructions and subjected to flow cytometric analysis (FACSCalibur) using HBS as sheath fluid. $[Ca^{2+}]_i$ levels determined by flow cytometry are reported as mean fluorescence intensity expressed in arbitrary units. Time courses of $[Ca^{2+}]_i$ rises in 2D culture are representative of three independent experiments and averaged $\Delta[Ca^{2+}]_i$ represents mean±SEM from the sum of three independent experiments. Fura-2 ratio images in 3D culture are representative of two independent experiments and averaged $[Ca^{2+}]_i$ in 3D culture represents mean±SEM from the sum of two independent experiments.

Immunofluorescence Staining

MCF-10A acini and HCC1569 spheroids were fixed with 4% paraformaldehyde at room temperature for 20 min and permeabilized in 0.15% Triton X-100 in PBS containing 5% goat serum at room temperature for 2 h. Antibodies used were Ki67 (DAKO) and Cleaved Caspase-3 (Asp175) antibody (Cell Signaling). Fluorescent images were acquired through the Eclipse Ti-E microscopes with A1R point scanning confocal (Nikon). Data are processed with NIS Elements software (Nikon). 3D images are shown as one section from midstructure. Images shown are representative of at least three independent experiments. For examination of luminal filling, spheroids were scored as clear (~90-100% clear), mostly clear (~50-90% clear), mostly filled (~10-50% clear), or clear (~0-10% clear), as previously reported (Schafer et al., Nature, 461:109-113, 2009).

Cell Viability, Apoptosis, and Cell Cycle Assays

For the measurements of live cell number and cell death under treatment with $H_2O_2$, diamide, or chemotherapies, cells were cultured on 96-well plates in the presence or absence of these drugs for indicated times and stained with 5 µM bisBenzimide H 33342 trihydrochloride (Hoechst; Sigma) and 5 µM propidium iodide (PI; Sigma) for 1 h at 37° C. Hoechst- and/or PI-positive cells were counted using a laser scanning cytometer, Acumen Cellista (TTPLabTech). Apoptotic cells induced by $H_2O_2$ treatment were measured by staining with Annexin V-Alexa Fluor® 488 conjugate (Life Technologies) and PI in $Ca^{2+}$-containing solution (10 mM HEPES pH 7.4, 140 mM NaCl; 2.5 mM $CaCl_2$), followed by flow cytometric measurement of fluorescence using a FACSCalibur. Flow cytometry plots are representative of three independent experiments. For the counting of viable cells cultured in suspension, cell clumps were dissociated with trypsin and stained with trypan blue. Viable cells were counted using the Countless Automated Cell Counters (Thermo Fisher Scientific). For the measurement of percentage of dead cells cultured in suspension, cells were cultured on poly HEMA-coated 96-well plates and stained with 5 µM Hoechst and 5 µM PI for 1 h at 37° C. without enzymatic dissociation of cell clumps. Hoechst- and/or PI-positive areas were measured using Acumen Cellista. Apoptotic cells induced by detachment were measured by staining with 5 µM Hoechst and 5 µM of CellEvent™ Caspase-3/7 Green Detection Reagent (Thermo Fisher Scientific) for 1 h at 37° C. without enzymatic dissociation of cell clumps. Hoechst- and/or CellEvent™ Caspase-3/7 Green Detection Reagent-positive areas were measured using Acumen Cellista. For the cell cycle analysis, enzymatically dissociated cells were fixed with ice-cold 70% EtOH for at least 30 min at 4° C., washed three times with PBS at 4° C., resuspended in PBS, treated with 100 µg/ml RNase A (Sigma), and stained with 50 µg/ml PI. The stained samples were subjected to flow cytometric analysis (FACSCalibur).

Soft Agar Assay

Cells were added to the regular MCF-10A or HCC1569 growth media (±AP-18, A-967079, or Trolox) plus 0.4% low-melt agarose (Sigma) and layered onto a bed of growth media plus 0.5% low-melt agarose. Cells were fed every 4 days with growth media (±AP-18, A-967079, or Trolox) plus 0.4% low-melt agarose. At the indicated times, viable colonies were stained with iodonitrotetrazolium chloride (Sigma). Colony number and colony size were determined using ImageJ. Images shown are representative of at least three independent experiments.

RPPA and Immunoblot Assay

For RPPA assay, sample preparation and probing with antibodies to the indicated proteins, normalization of data points, and analysis were performed as previously described. For immunoblot analysis for all the indicated proteins except for TRPA1, cells were lysed in cell lysis buffer (1% Triton X-100, 150 mM NaCl, 1.5 mM $MgCl_2$, 1 mM EGTA, 100 mM NaF, 10 mM Na pyrophosphate, 10% glycerol, 50 mM HEPES pH 7.4) with protease and phosphatase inhibitor cocktails (Roche) and 1 mM $Na_3VO_4$ (Sigma). Protein concentrations were determined by BCA protein assay (Life Technologies). Equal protein amounts were denatured in SDS sample buffer (10% Glycerol, 2% SDS, 62.5 mM Tris-HCL, pH 6.8) with 1% β-mercaptoethanol for 10 min at 95° C. For immunoblot analysis for TRPA1 protein, membrane fraction was isolated by using Mem-PER™ Plus Membrane Protein Extraction Kit (Life Technologies) according to the manufacturer's instructions. Equal protein amounts were denatured in SDS sample buffer with 50 mM dithiothreitol using a vortex mixer for 30 min at room temperature. Proteins were analyzed by SDS-PAGE and immunoblot using the indicated antibodies. Blots were imaged with the Odyssey CLx infrared imaging system (LI-COR) and are representative of at least two independent experiments where indicated. Ras activities were assessed using the Active Ras Pull-Down and Detection Kit (Thermo Fisher Scientific) according to the manufacturer's instructions.

Quantitative PCR mRNA prepared from cell extracts using the RNeasy Mini Kit (QIAGEN) was reverse-transcribed into cDNA using the qScript cDNA synthesis kit (Quanta Biosciences). Real-time PCR was performed on an ABI PRISM 7900HT or QuantStudio 7 Flex Real-Time PCR System (Life Technologies) with Power SYBR Green PCR Mix (Life Technologies). Primers used for the analysis are shown in Table 4.

TABLE 4

Primer sequences used for Real-time PCR

| Genes or ID | Mutation primer sequences (5'→3') |
|---|---|
| TRPA1 | for: ATCAGAAATCCACCATCGTG (SEQ ID NO: 15) rev: TTGACTGCTCTCAACACAGTATTC (SEQ ID NO: 16) |

TABLE 4-continued

Primer sequences used for Real-time PCR

| Genes or ID | Mutation primer sequences (5'→3') |
|---|---|
| B-Actin | for: GACAGGATGCAGAAGGAGATC (SEQ ID NO: 17)<br>rev: TGCTGATCCACATCTGCTG (SEQ ID NO: 18) |
| RF2 | for: GAGAGCCCAGTCTTCATTGC (SEQ ID NO: 19)<br>rev: TTGGCTTCTGGACTTGGAAC (SEQ ID NO: 20) |
| NQO1 | for: TGAAGAAGAAAGGATGGGAGGT (SEQ ID NO: 21)<br>rev: GGCCTTCTTTATAAGCCAGAACA (SEQ ID NO: 22) |
| Peak1 region | for: ATGTTTATTGCTGTGGTTTGAG (SEQ ID NO: 23)<br>rev: CTTCCGCAATGATGACTCAG (SEQ ID NO: 24) |
| Peak2 region | for: AAGTGAGAGCCAGACAGTCC (SEQ ID NO: 25)<br>rev: GGAATTGAGAAGAGAAGACAGATTG (SEQ ID NO: 26) |
| Peak3 region | for: CCCAGAAATAGGATTTAAGACAGG (SEQ ID NO: 27)<br>rev: AGGAACTTACAAGATTCTAAAGCTG (SEQ ID NO: 28) |
| Non-Peak region | for: GTGTACAGAATGCGGAAAAC (SEQ ID NO: 29)<br>rev: CCCAAAGTGCTAGGATTACAG (SEQ ID NO: 30) |
| NQO1 promoter | for: AAGTGCAGAATCTGAATCTTG (SEQ ID NO: 31)<br>rev: AGATTCTGCTGAGTCACTGTG (SEQ ID NO: 32) | for: forward primer;
rev: reverse primer

Chromatin Immunoprecipitation

H1792 cells overexpressing Flag-NRF2 were cross-linked in the culture medium with 1% formaldehyde for 10 min at room temperature. The reaction was stopped by the addition of 100 mM glycine, followed by 5 mg/mL BSA in PBS and then two washing in cold PBS. Cells were harvested and resuspended in lysis buffer [50 mM Tris.HCl, pH 8.0, 10 mM EDTA, 1% SDS, 1× Protease Inhibitor Cocktail (Selleck Chemicals)], and then sonicated with a Sonic Dismembrator (Fisher Scientific, Model FB120) to obtain a fragment size of 300-500 bp. Fragmented chromatin was diluted in IP buffer (20 mM Tris.HCl, pH 8.0, 150 mM NaCl, 2 mM EDTA, 1% Triton X-100, 1× Protease Inhibitor Cocktail) and incubated overnight at 4° C. with Protein G magnetic beads (Dynabeads; Thermo Fisher Scientific) that had been pre-incubated with monoclonal anti-Flag M2 antibody (Sigma, F1804) or mouse IgG (Thermo Fisher Scientific). Immunoprecipitates were washed three times with wash buffer (50 mM Hepes, pH 7.6, 0.5 M LiCl, 1 mM EDTA, 0.7% Na deoxycholate, and 1% Nonidet P-40) and twice with TE buffer. Immunoprecipitated (or no IP input) DNA was recovered in Elution Buffer (1% SDS and 0.1 M NaHCO3) over 6 h at 65° C., and then column-purified with QiaQuick columns (Qiagen). Quantitative PCR was performed with Fast SYBR Green Master Mix (Life Technologies) on a QuantStudio 7 Flex Real-Time PCR System (Life Technologies). Primer sequences are listed in Table 5.

TABLE 5

Primer Sequences Used for the Construction of LentiCRISPR Plasmids

| Plasmid ID | Mutation primer sequences (5'→3') |
|---|---|
| sgPeak1 #1 | for: caccgTGAGTCATCATTGCGGAAGT (SEQ ID NO: 33)<br>rev: aaacACTTCCGCAATGATGACTCAc (SEQ ID NO: 34) |
| sgPeak1 #2 | for: caccgACTTCCGCAATGATGACTCA (SEQ ID NO: 35)<br>rev: aaacTGAGTCATCATTGCGGAAGTc (SEQ ID NO: 36) |
| sgPeak1 #3 | for: caccgAACTTCCGCAATGATGACTC (SEQ ID NO: 37)<br>rev: aaacGAGTCATCATTGCGGAAGTTc (SEQ ID NO: 38) |
| sgPeak1 #4 | for: caccgAAGCCCTGAGTCATCATTG (SEQ ID NO: 39)<br>rev: aaacCAATGATGACTCAGGGCTTCc (SEQ ID NO: 40) |
| sgPeak1 #5 | for: caccgAGGACCTCTATTTATTCAGC (SEQ ID NO: 41)<br>rev: aaacGCTGAATAAATAGAGGTCCTc (SEQ ID NO: 42) |
| sgPeak1 #6 | for: caccgATGGTGGAATTTGTGTTACT (SEQ ID NO: 43)<br>rev: aaacAGTAACACAAATTCCACCATc (SEQ ID NO: 44) |
| sgPeak1 #7 | for: caccgTACCATAAAGGTTTACTAAT (SEQ ID NO: 45)<br>rev: aaacATTAGTAAACCTTTATGGTAc (SEQ ID NO: 46) |
| sgPeak1 #8 | for: caccgCCACTGTATTTCAAAAGCTT (SEQ ID NO: 47)<br>rev: aaacAAGCTTTTGAAATACAGTGGc (SEQ ID NO: 48) |
| sgPeak2 #1 | for: caccgTAAGAGCTGAATGGTAGCAC (SEQ ID NO: 49)<br>rev: aaacGTGCTACCATTCAGCTCTTAc (SEQ ID NO: 50) |
| sgPeak2 #2 | for: caccgTTGAACTCAGGCATAGTGCT (SEQ ID NO: 51)<br>rev: aaacAGCACTATGCCTGAGTTCAAc (SEQ ID NO: 52) |
| sgPeak2 #3 | for: caccgAAGAGCTGAATGGTAGCACA (SEQ ID NO: 53)<br>rev: aaacTGTGCTACCATTCAGCTCTTc (SEQ ID NO: 54) |
| sgPeak2 #4 | for: caccgAGTGGGGCAGAAGTTTGGAC (SEQ ID NO: 55)<br>rev: aaacGTCCAAACTTCTGCCCCACTc (SEQ ID NO: 56) |
| sgPeak2 #5 | for: caccgGAGAGAATGACTCAGCAGAT (SEQ ID NO: 57)<br>rev: aaacATCTGCTGAGTCATTCTCTCc (SEQ ID NO: 58) |
| sgPeak2 #6 | for: caccgTTGGACTGGTAAGAGCTGAA (SEQ ID NO: 59)<br>rev: aaacTTCAGCTCTTACCAGTCCAAc (SEQ ID NO: 60) |
| sgPeak2 #7 | for: caccgAATGGTAGCACAGGGCAGC (SEQ ID NO: 61)<br>rev: aaacGCTGCCCTGTGCTACCATTCc (SEQ ID NO: 62) |

TABLE 5-continued

Primer Sequences Used for the Construction of LentiCRISPR Plasmids

| Plasmid ID | Mutation primer sequences (5'→3') |
|---|---|
| sgPeak2 #8 | for: caccgAGAGAGAATGACTCAGCAGA (SEQ ID NO: 63)<br>rev: aaacTCTGCTGAGTCATTCTCTCTc (SEQ ID NO: 64) |
| sgPeak3 #1 | for: caccgTTCAGGCACTGTCACACCCT (SEQ ID NO: 65)<br>rev: aaacAGGGTGTGACAGTGCCTGAAc (SEQ ID NO: 66) |
| sgPeak3 #2 | for: caccgATAGGATTTAAGACAGGTTC (SEQ ID NO: 67)<br>rev: aaacGAACCTGTCTTAAATCCTATc (SEQ ID NO: 68) |
| sgPeak3 #3 | for: caccgCTTGGCTCTGTCATTATTAG (SEQ ID NO: 69)<br>rev: aaacCTAATAATGACAGAGCCAAGc (SEQ ID NO: 70) |
| sgPeak3 #4 | for: caccgACATATATAGTGACTCAGCA (SEQ ID NO: 71)<br>rev: aaacTGCTGAGTCACTATATATGTc (SEQ ID NO: 72) |
| sgPeak3 #5 | for: caccgCACTAATAATGACAGAGCCA (SEQ ID NO: 73)<br>rev: aaacTGGCTCTGTCATTATTAGTGc (SEQ ID NO: 74) |
| sgPeak3 #6 | for: caccgACTAATAATGACAGAGCCAA (SEQ ID NO: 75)<br>rev: aaacTTGGCTCTGTCATTATTAGTc (SEQ ID NO: 76) |
| sgPeak3 #7 | for: caccgTACAAGATTCTAAAGCTGAA (SEQ ID NO: 77)<br>rev: aaacTTCAGCTTTAGAATCTTGTAc (SEQ ID NO: 78) |
| sgPeak3 #8 | for: caccgTAATAAGTCATCTTTGTCAA (SEQ ID NO: 79)<br>rev: aaacTTGACAAAGATGACTTATTAc (SEQ ID NO: 80) | for: forward primer;
rev: reverse primer

ATP and Glucose Uptake Assay

For the measurement of ATP levels, the ATPlite assay kit (PerkinElmer) was used. Cells were plated in poly HEMA-coated (or uncoated) 96-well plates. After 24 h, ATP assay was conducted according to the manufacturer's protocol. ATP levels were measured through the detection of luminescent signals by using the SpectraMax M5 (Molecular Devices) and were normalized by total cell number. For the analysis of glucose uptake, the Amplex Red Glucose Assay Kit (Invitrogen) was used. Cells were plated in poly HEMA-coated (or uncoated) 96-well plates. After 24 h, the media was collected and the amount of glucose was determined through the detection of fluorescent signals using the SpectraMax M5, according to the manufacturer's protocol. Glucose uptake was determined by subtracting the amount of glucose in each sample from the total amount of glucose in the media (without cells). The data were normalized by total cell number.

Bioinformatics and Statistical Analysis

Analysis of the TCGA invasive breast carcinoma data was conducted on processed data downloaded through Oncomine (www.oncomine.com). mRNA and protein heatmaps were generated in Cluster 3.0 as a hierarchical cluster using Pearson Correlation and a center metric. The resulting heatmap was visualized in Java Treeview. Published NSCLC and MPNST datasets were downloaded from Hou et al. (GSE19188, Gene Expression Omnibus www.ncbi.nlm.nih.gov/geo) and Miller et al. (GSE14038, GEO). Error bars represent either the SD or SEM, as described in the figure legends. The sample size for each experiment, n, is included in the associated figure legend. Statistical significance was determined by the Student's t test and the one-way or two-way ANOVA followed by Tukey's test using Graph Pad Prism 7.0. P-values<0.05 were considered significant. P values for each experiment are also included in the associated figure legends.

Example 2: TRPA1 is Highly Expressed in Breast Tumors

Figure 1B:
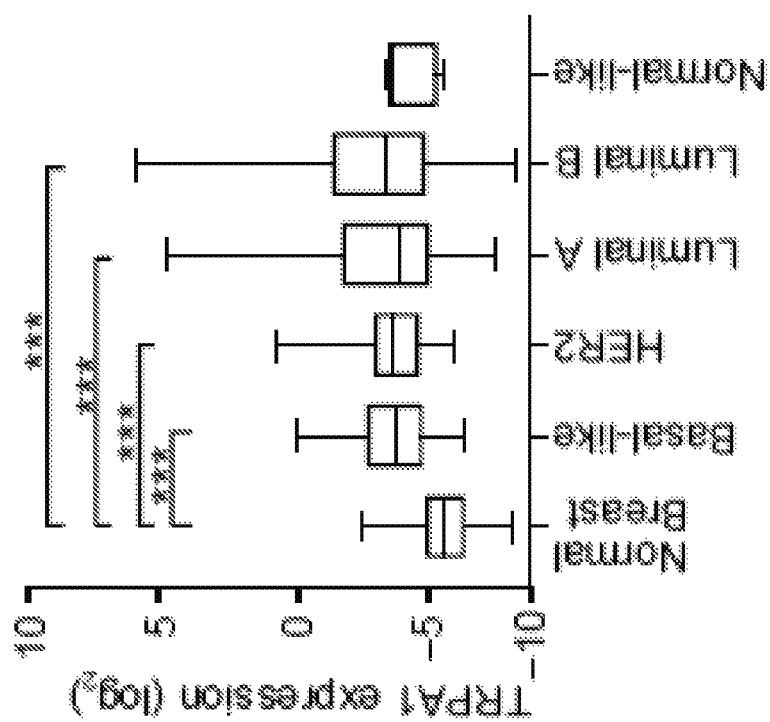
FIG. 1B is a series of box plots displaying TRPA1 mRNA levels in normal breast tissues (n=61) and Basal-like (n=78), HER2 (n=49), Luminal A (n=151), Luminal B (n=100), and Normal-like (n=5) subtypes of breast tumors. ***P<0.001 (one-way ANOVA).

To assess the expression of TRP channel subtypes in breast tumors, we first analyzed their mRNA expression profiles using the Cancer Genome Atlas (TCGA) dataset. A subset of TRP channels exhibited altered expression in breast tumors relative to normal mammary tissues (FIG. 1A); upregulated: TRPA1, PKD2L1, TRPML2, TRPM2, TRPM4, TRPM5, TRPM7, TRPC4, TRPML1, TRPV1, and TRPC7, downregulated: TRPM1, PKD2, TRPC1, and TRPC6). Within this subset, TRPA1, which is predominantly expressed in sensory neurons, was the most highly upregulated (P<0.001; ANOVA followed by Tukey's test). TRPA1 mRNA was indiscriminately upregulated in all breast cancer subtypes except for normal-like subtype (FIG. 1B). Consistent with this result, immunohistochemistry (IHC) analysis of a panel of breast cancer and normal breast tissue samples revealed that TRPA1 protein expression was significantly higher in ductal breast carcinoma [FIG. 1C; 16/70 positive in breast cancer tissues (3+ or greater), 0/15 positive in normal breast tissues, $\chi^2$ test: P=0.0399]. Prominent membranous and cytoplasmic TRPA1 staining was detected in 6/11 breast tumors (with an additional 3/11 showing low intensity staining) from the Human Protein Atlas initiative (www.proteinatlas.org/).

Figures 1D, 1E, 1F:
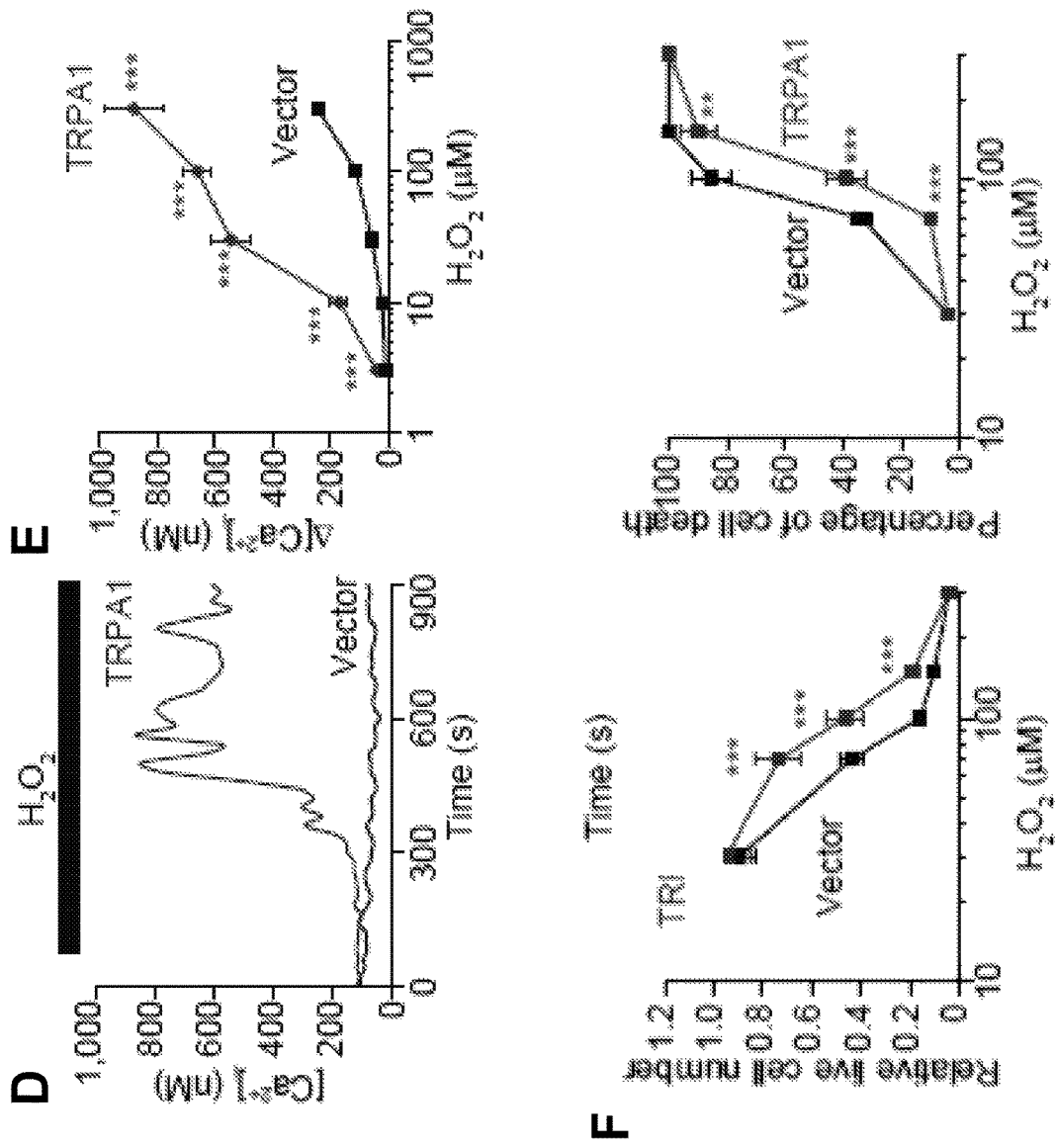
FIG. 1D is a graph of a representative time course of $[Ca^{2+}]_i$ rises evoked by 100 μM $H_2O_2$ applied during periods indicated by black bar in MCF-10A cells transduced with an empty lentiviral vector or TRPA1.
FIG. 1E is a graph of a dose-response of the maximal $[Ca^{2+}]_i$ rises ($\Delta[Ca^{2+}]_i$) elicited upon treatment with increasing concentrations of $H_2O_2$. Data shown as mean±SEM (n=58-167). ***P<0.001 compared to vector (Student's t test).
FIG. 1F is a series of graphs of live cell numbers relative to $H_2O_2$-untreated cells and percentage of cell death in the indicated cells treated with $H_2O_2$ for 72 h, as determined by dual staining of Hoechst and propidium iodide (PI). Data shown as mean±SD (n=6: the sum of three independent experiments performed in duplicate). P<0.01 and *P<0.001 compared to vector (Student's t test).

Example 3: TRPA1 Expression Promotes Cell Survival in Response to Exogenous Oxidative Stress or Loss of Matrix Attachment We investigated the impact of exogenous TRPA1 expression on viability of MCF-10A mammary epithelial cells in response to treatment with $H_2O_2$, a stable, membrane permeable cellular ROS molecule. $H_2O_2$ elicited enhanced $[Ca^{2+}]_i$ increases in TRPA1-expressing cells in a concentration-dependent manner (FIGS. 1D and 1E). We removed EGF from MCF-10A culture medium to mimic the situation of detachment and examined the effect of $H_2O_2$ treatment on cell viability. TRPA1 expression increased live cell number and suppressed cell death and apoptosis in response to $H_2O_2$ (FIG. 1F).

Figures 1G, 1H:
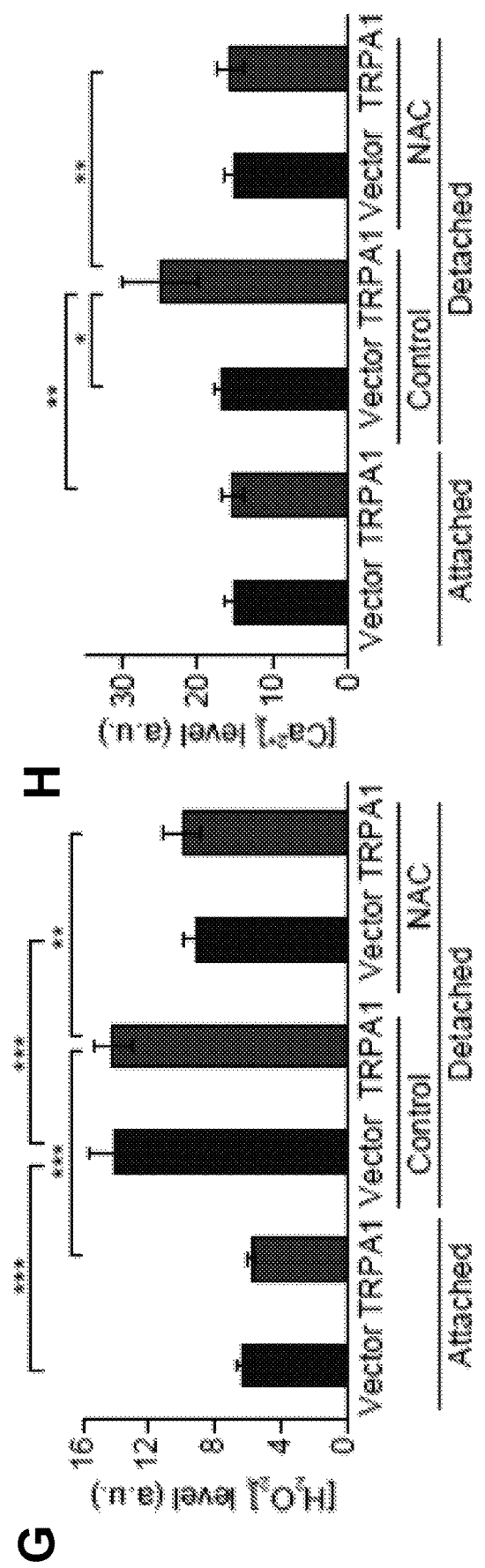
FIG. 1G is a graph of $[H_2O_2]_i$ levels as determined by peroxy green-1 and Fluo-4 staining, respectively, in the indicated cells 24 h after plating in adherent or non-adherent plates. Cells were treated with or without 1 mM NAC. Data shown as mean±SD of three independent experiments. *P<0.05, P<0.01, and *P<0.001 (one-way ANOVA).
FIG. 1H is a graph of $[Ca^{2+}]_i$ levels as determined by peroxy green-1 and Fluo-4 staining, respectively, in the indicated cells 24 h after plating in adherent or non-adherent plates. Cells were treated with or without 1 mM NAC. Data shown as mean±SD of three independent experiments. *P<0.05, P<0.01, and *P<0.001 (one-way ANOVA).
Figures 1I, 1J:
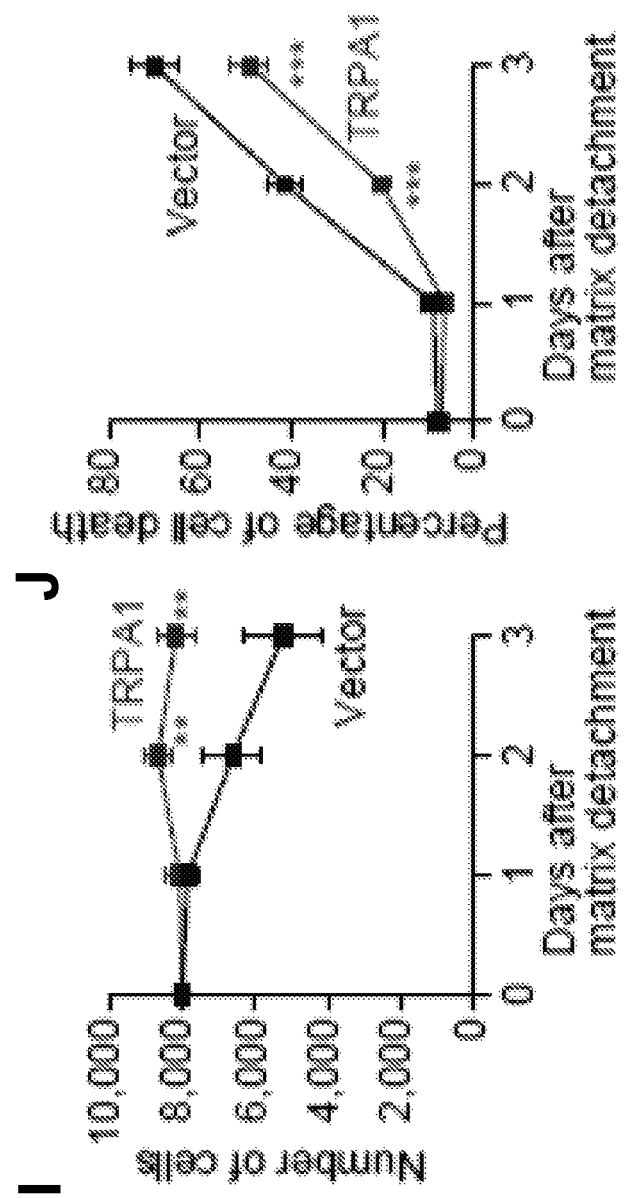
FIG. 1I is a graph of cell number marked by tripan blue assay in the indicated cells after matrix detachment. Data shown as mean±SD of four independent experiments. P<0.01 and P<0.001 compared to vector (Student's t test).
FIG. 1J is a graph of percentage of cell death marked by dual staining of Hoechst and PI in the indicated cells after matrix detachment. Data shown as mean±SD of four independent experiments. P<0.01 and P<0.001 compared to vector (Student's t test).

We next examined the effects of TRPA1 on the intracellular concentration of $H_2O_2$ ($[H_2O_2]_i$), $[Ca^{2+}]_i$, and survival in ECM-detached cells cultured on non-adherent (poly-HEMA-coated) plates. Flow cytometry analysis with the $H_2O_2$-specific probe peroxy green-1 showed that detachment induced a significant increase in $[H_2O_2]_i$ (FIG. 1G). This increase in $[H_2O_2]_i$ was unaffected by TRPA1 expression but was suppressed by the antioxidant N-Acetyl-L-cysteine (NAC), indicating that TRPA1 does not act as an antioxidant per se. Notably, detachment induced a TRPA1- dependent increase in $[Ca^{2+}]_i$ that was abolished by NAC (FIG. 1H), suggesting that TRPA1 mediates $Ca^{2+}$ entry in response to $H_2O_2$ induction following ECM detachment. TRPA1 expression increased cell number and suppressed cell death and apoptosis in suspension culture (FIGS. 1I and 1J). Collectively, these data demonstrate that TRPA1 promotes cell survival and proliferation under oxidative conditions, including ECM detachment, without affecting cellular ROS levels, suggesting that TRPA1 mediates these effects through a mechanism distinct from canonical antioxidant pathways.

Figure 2A:
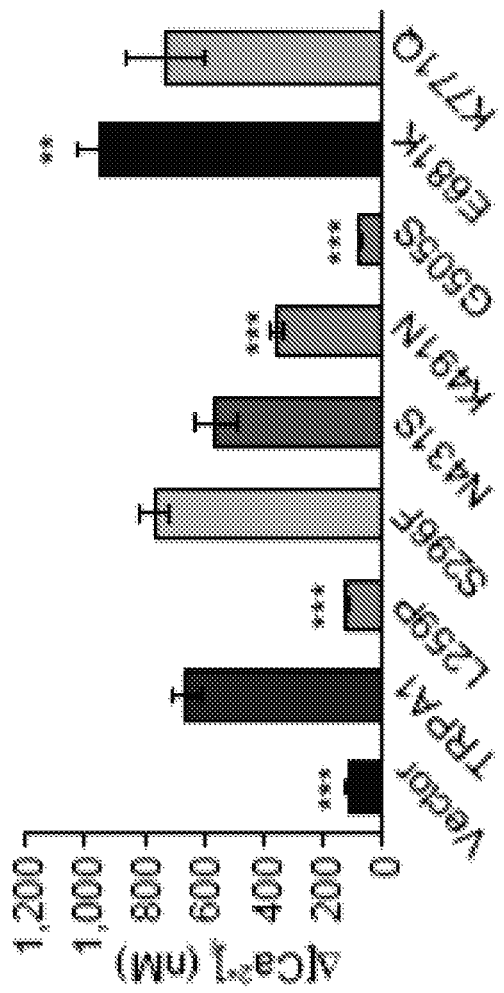
FIG. 2A is a graph of $Ca^{2+}$ responses to 100 μM $H_2O_2$ in MCF-10A cells transduced with vector or TRPA1 constructs: $\Delta[Ca^{2+}]_i$ rises. Data shown as mean±SEM (n=21-167). P<0.01 and P<0.001 compared to TRPA1 (Student's t test).

Example 4: Breast Cancer-Associated TRPA1 Mutations Affect TRPA1-Mediated Redox Adaptation in an Activity-Dependent Manner To investigate whether the ability of TRPA1 to promote redox adaptation is dependent on its $Ca^{2+}$ channel activity and to evaluate the functional activity of TRPA1 mutations associated with breast cancer, we analyzed seven TRPA1 missense mutations that were identified in breast tumors by TCGA. Most of the mutations either reduced or failed to affect $Ca^{2+}$ responses of TRPA1 to $H_2O_2$ (FIG. 2A). In contrast, the E681K mutation, which has also been identified in endometrial tumors, prominently sensitized TRPA1 to $H_2O_2$.

Figure 2B:
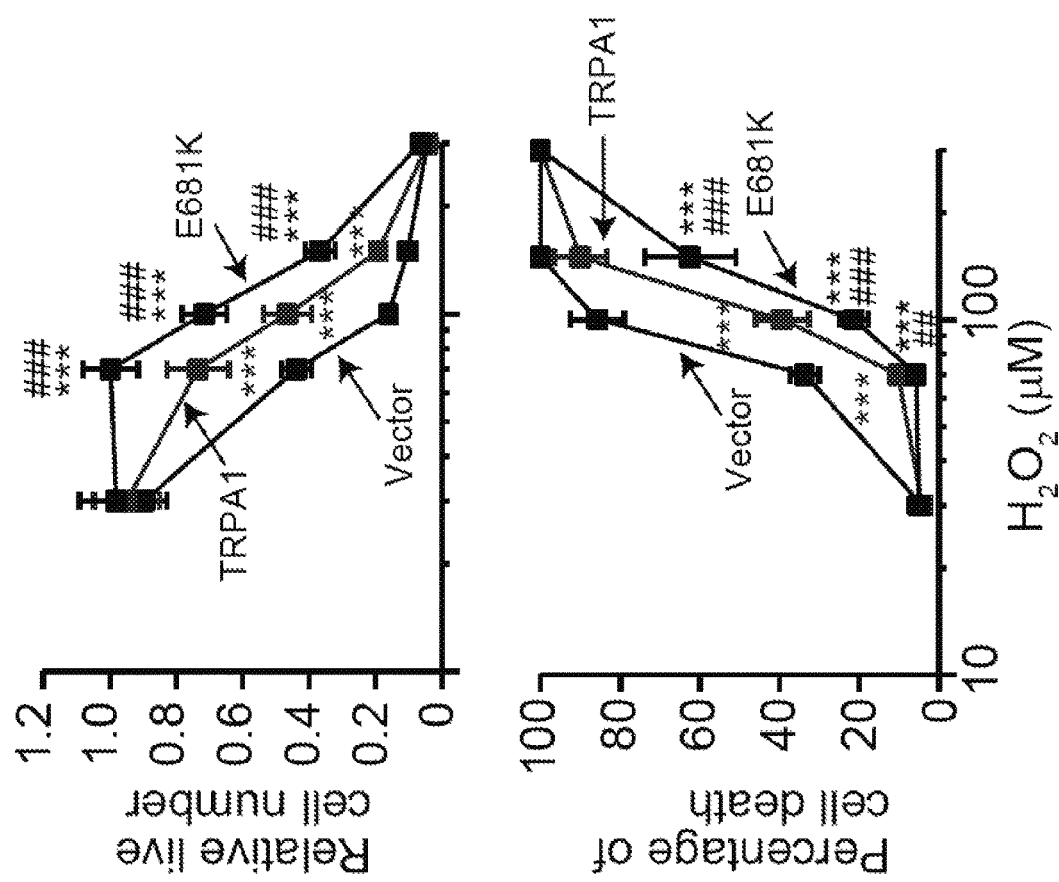
FIG. 2B is a series of graphs of live cell numbers relative to $H_2O_2$-untreated cells and percentage of cell death in the indicated cells treated with increasing concentrations of $H_2O_2$ for 72 h. Data shown as mean±SD (n=6: the sum of three independent experiments performed in duplicate). ***P<0.001 compared to vector and ##P<0.01 and ###P<0.001 compared between TRPA1 and E681K (one-way ANOVA). The data for TRPA1 and vector are from FIG. 1G as these samples were analyzed at the same time.
Figures 2C, 2D:
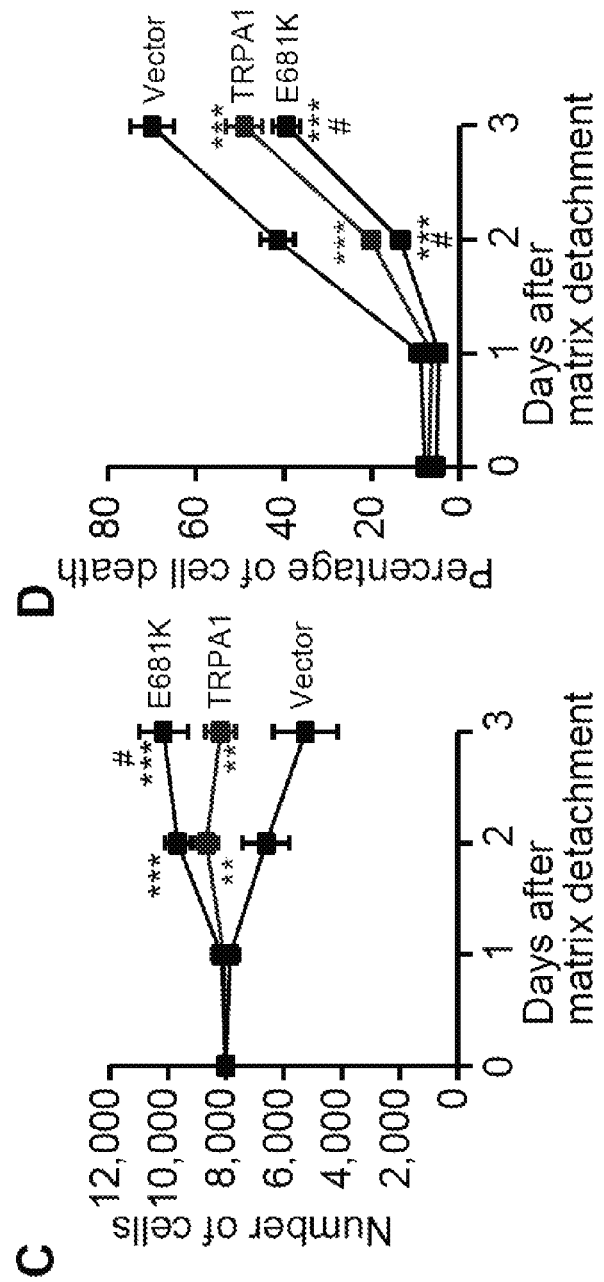
FIG. 2C is a graph of cell number in the indicated cells after matrix detachment for the indicated time. Data shown as mean±SD of four independent experiments. P<0.01 and *P<0.001 compared to vector and #P<0.05 compared between TRPA1 and E681K (one-way ANOVA). The data for TRPA1 and vector in are from FIG. 1H as these samples were analyzed at the same time.
FIG. 2D is a graph of the percentage of cell death in the indicated cells after matrix detachment for the indicated time. Data shown as mean±SD of four independent experiments. P<0.01 and *P<0.001 compared to vector and #P<0.05 compared between TRPA1 and E681K (one-way ANOVA). The data for TRPA1 and vector in are from FIG. 1I as these samples were analyzed at the same time.

We next examined whether the activity of the TRPA1 mutant variants affected their ability to protect cells from cell death induced by $H_2O_2$ or matrix detachment. The ability of the TRPA1 mutants to promote cell viability in response to $H_2O_2$ mirrored their observed $Ca^{2+}$ responses elicited by this treatment, with those mutants with impaired activity showing reduced cell viability, and only E681K, the lone mutant with enhanced activity, showing improved cell viability compared to wild-type TRPA1 (FIG. 2B). The E681K mutant also enhanced cell survival compared to wild-type TRPA1 in suspension culture (FIGS. 2C and 2D). Thus, the observed parallel between $Ca^{2+}$ responses and cell survival phenotypes strongly suggests that TRPA1-mediated redox adaptation is largely dependent on its activity. In addition, the evidence that only one of the mutations displayed significant enhancement of $Ca^{2+}$ responses suggests that most TRPA1 mutations associated with breast cancer are not of functional significance.

Figures 3A, 3B:
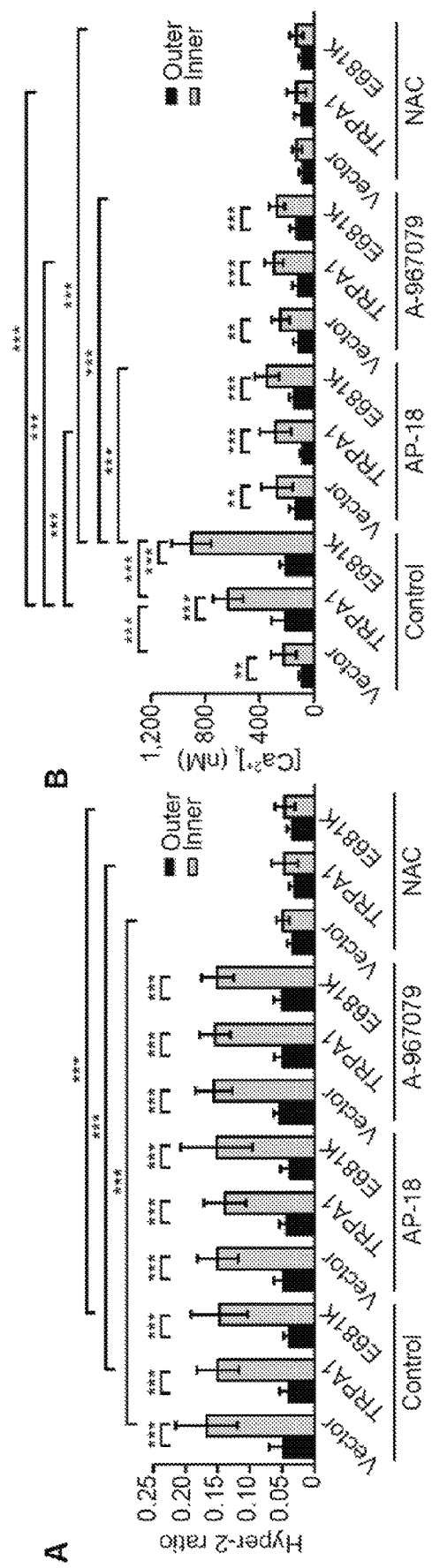
FIG. 3A is a graph of the averaged Hyper-2 ratio in the inner and outer region of acini. Data shown as mean±SD (n=4-13). P<0.01 and P<0.001 (one-way ANOVA).
FIG. 3B is a graph of the averaged $[Ca^{2+}]_i$ in the inner and outer region of acini. Data shown as mean±SD (n=4-13). P<0.01 and *P<0.001 (one-way ANOVA).

Example 5: TRPA1 Expression in MCF-10A Acini Elevates $[Ca^{2+}]_i$ in the Inner ECM-Deprived Cells and Promotes Their Viability in Response to ROS To extend our analysis to a model with more physiological relevance, we investigated the impact of TRPA1 expression on $[Ca^{2+}]_i$ and cell viability in MCF-10A three-dimensional (3D) acini cultured with reconstituted basement membrane (Matrigel), a well-suited model to examine putative regulators and effectors of oxidative stress because centrally localized cells that lack ECM attachment accumulate ROS which contribute to the induction of cell death, mimicking the developing mammary gland. To assess the level of $[H_2O_2]_i$ in the inner ECM-deprived cells of MCF-10A acini, we used the genetically-encoded ratiometric $H_2O_2$ probe Hyper-2. Hyper-2 showed increased signal in the inner ECM-deprived cells of MCF-10A acini (FIG. 3A), indicating that the inner ECM-deprived cells accumulate $H_2O_2$. This increase in $[H_2O_2]_i$ was unaffected by TRPA1 or E681K expression, or the TRPA1-specific antagonists AP-18 or A-967079, but was abolished by NAC, indicating that TRPA1 does not act as an antioxidant. We also observed that $[Ca^{2+}]_i$ was marginally increased in the inner ECM-deprived region of MCF-10A acini and this effect was markedly augmented by expression of TRPA1, with the E681K mutant inducing a more pronounced effect than wild-type (FIG. 3B). TRPA1- or E681K-induced $[Ca^{2+}]_i$ rises were abolished by AP-18, A-967079, or NAC, suggesting that $H_2O_2$ produced as a result of ECM detachment activates TRPA1 channels in MCF-10A acini.

Figures 3C, 3D:
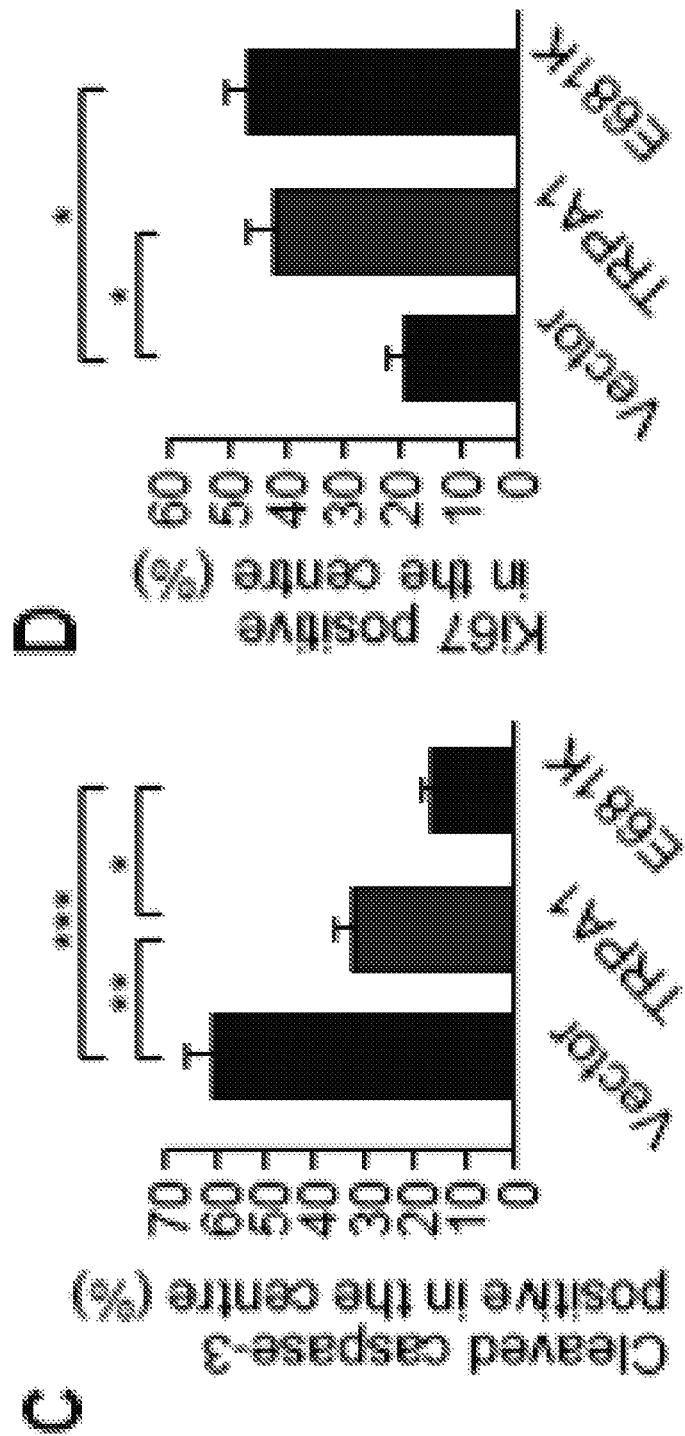
FIG. 3C is a graph of the percentage of acini with cleaved caspase-3-positive staining in the center. Data shown as mean±SEM of three or five independent experiments. *P<0.05, P<0.01, and *P<0.001 (one-way ANOVA).
FIG. 3D is a graph of the percentage of acini with cleaved Ki67-positive staining in the center. Data shown as mean±SEM of three or five independent experiments. *P<0.05, P<0.01, and *P<0.001 (one-way ANOVA).

To understand the implications of TRPA1-dependent $[Ca^{2+}]_i$ rises with regard to cell viability in the MCF-10A 3D model, we examined the effects of TRPA1 expression on apoptosis and proliferation of the inner ECM-deprived cells. TRPA1 expression prominently suppressed apoptosis (marked by cleaved caspase-3 staining) and enhanced proliferation (marked by Ki67 staining) of the cells localized in the inner region of the MCF-10A acini, indicating that TRPA1 promotes anchorage-independent survival (FIGS. 3C and 3D). Compared to wild-type TRPA1, the E681K mutant substantially suppressed apoptosis, but not proliferation, of the inner cells.

Figure 3E:
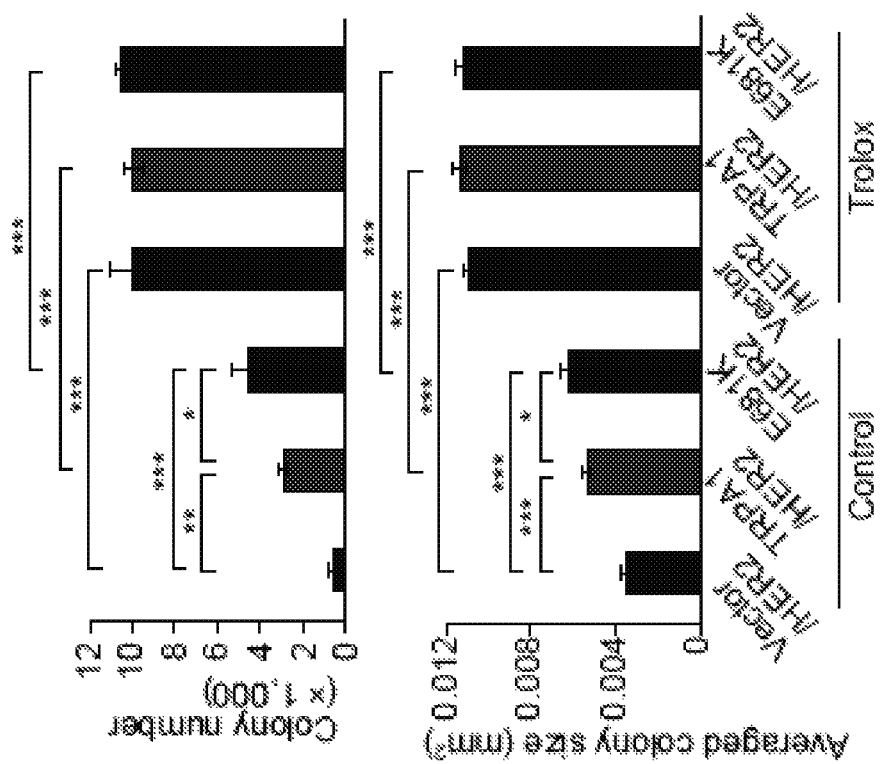
FIG. 3E is a series of graphs of colony number and averaged colony size. Data shown as mean±SD of three independent experiments. *P<0.05, P<0.01, and *P<0.001 (one-way ANOVA).

The evidence that TRPA1 expression can promote anchorage-independent survival raises the question of whether it could promote the transforming activity of mammary epithelial cells. To examine this, we assayed anchorage-independent colony formation in soft agar. As reported previously, MCF-10A cells require the expression of oncogenes to form colonies in soft agar even in the presence of the antioxidant Trolox (a water-soluble vitamin E derivative). Therefore, we investigated the effects of TRPA1 on the colony forming ability of MCF-10A cells expressing HER2, which exhibit relatively weak activity in this assay. Trolox treatment strongly increased both colony number and size (FIG. 3E). Expression of either wild-type or E681K TRPA1 induced a substantial increase in the number and average size of colonies, and this effect was eliminated by Trolox, suggesting that ROS-induced TRPA1 activation can enhance the transforming activity of cells that harbor oncogenic insults.

Example 6: TRPA1 Confers Anchorage-Independent Survival on Breast Cancer Cells

Figures 4A, 4B:
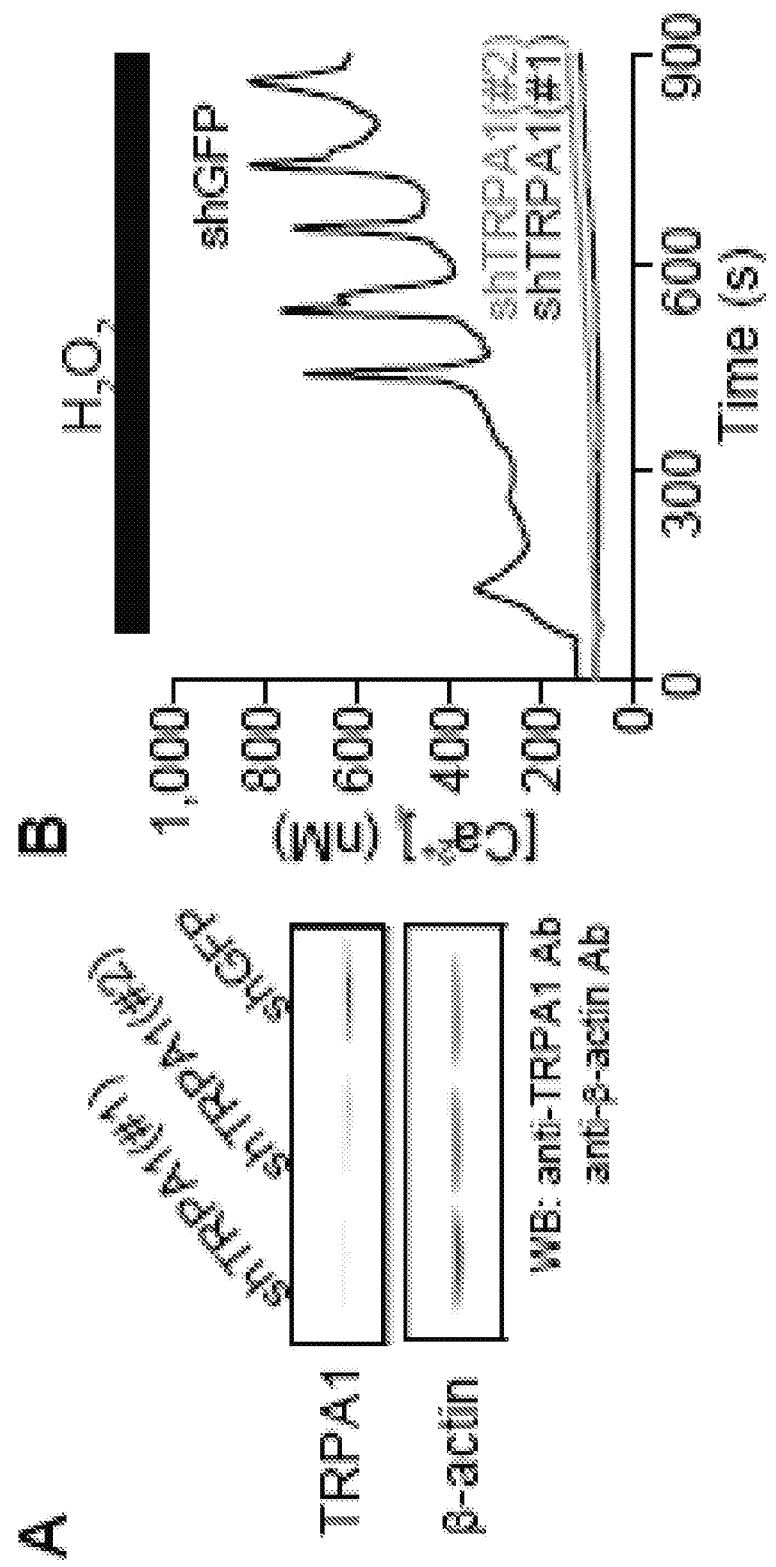
FIG. 4A is a photograph of an immunoblot analysis of TRPA1 in HCC1569 cells transduced with shRNA against TRPA1 or GFP (control).
FIG. 4B is a graph of representative time courses of $Ca^{2+}$ responses to 10 μM $H_2O_2$ in the indicated cells.
Figure 4C:
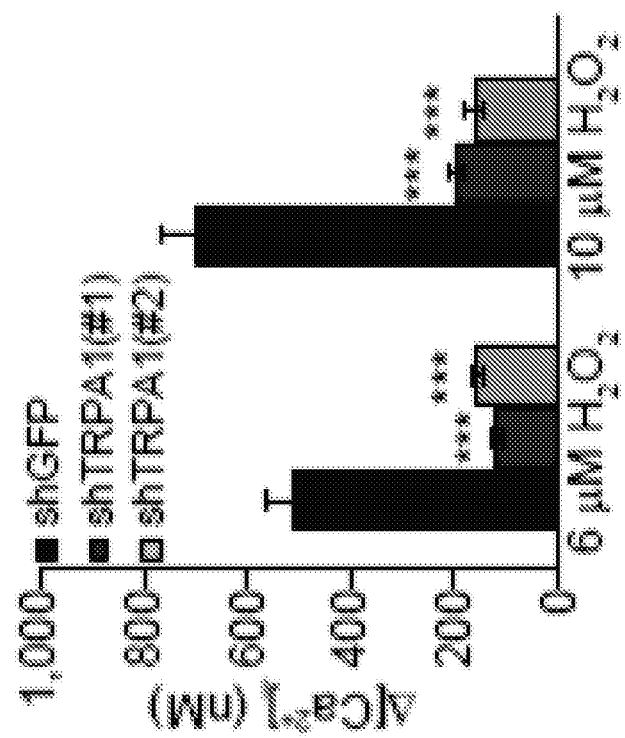
FIG. 4C is a graph of the $\Delta[Ca^{2+}]_i$ upon treatment with $H_2O_2$. Data is mean±SEM (n=35-77). ***P<0.001 compared to shGFP (Student's t test).
Figure 4D:
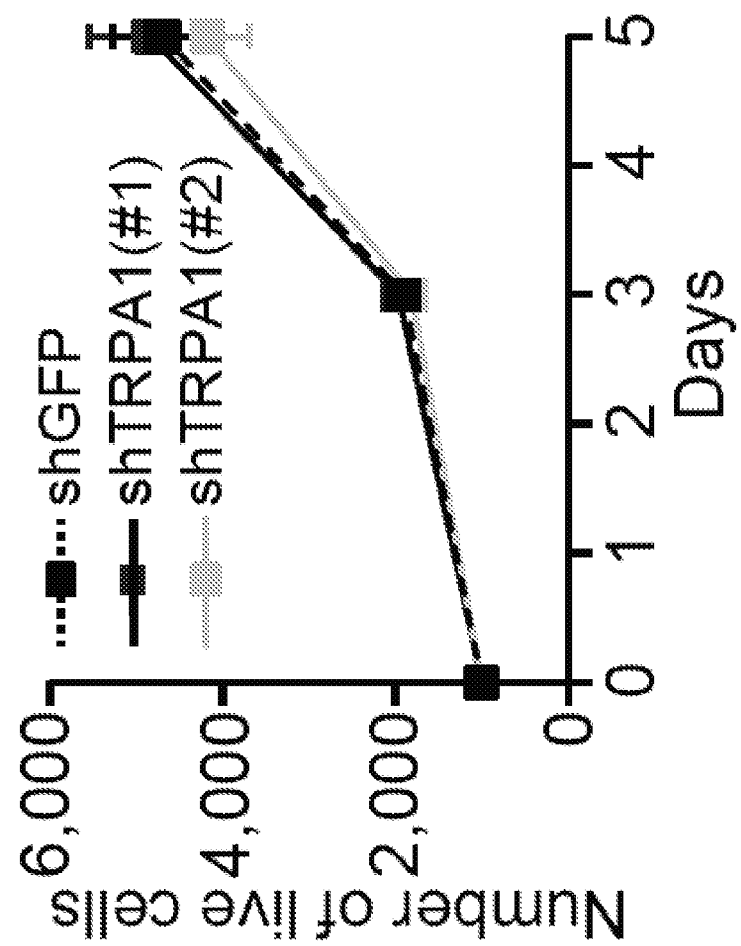
FIG. 4D is a graph of live cell numbers in HCC1569 cells transduced with shTRPA1 or shGFP for the indicated times. Data shown as mean±SD (n=6: the sum of three independent experiments performed in duplicate).
Figure 4E:
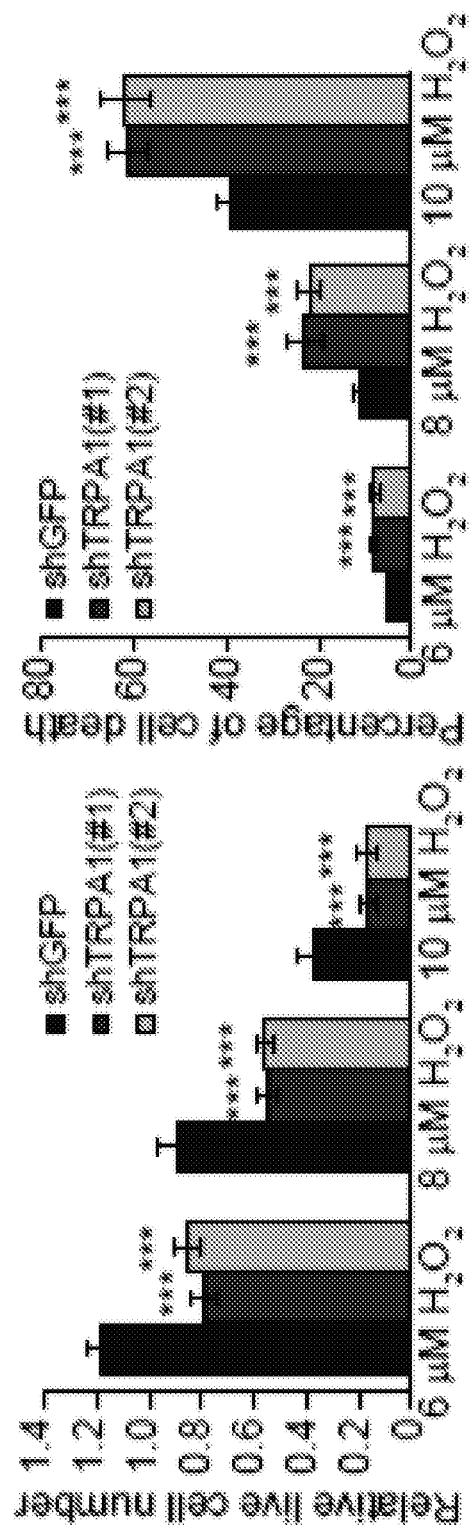
FIG. 4E is a series of graphs of live cell numbers relative to $H_2O_2$-untreated cells (left) and percentage of cell death (right) in HCC1569 cells transduced with shTRPA1 or shGFP upon treatment with $H_2O_2$ for 72 h, which were calculated as in FIG. 1G. Data shown as mean±SD (n=6: the sum of three independent experiments performed in duplicate). ***P<0.001 compared to shGFP (Student's t test).
Figure 4F:
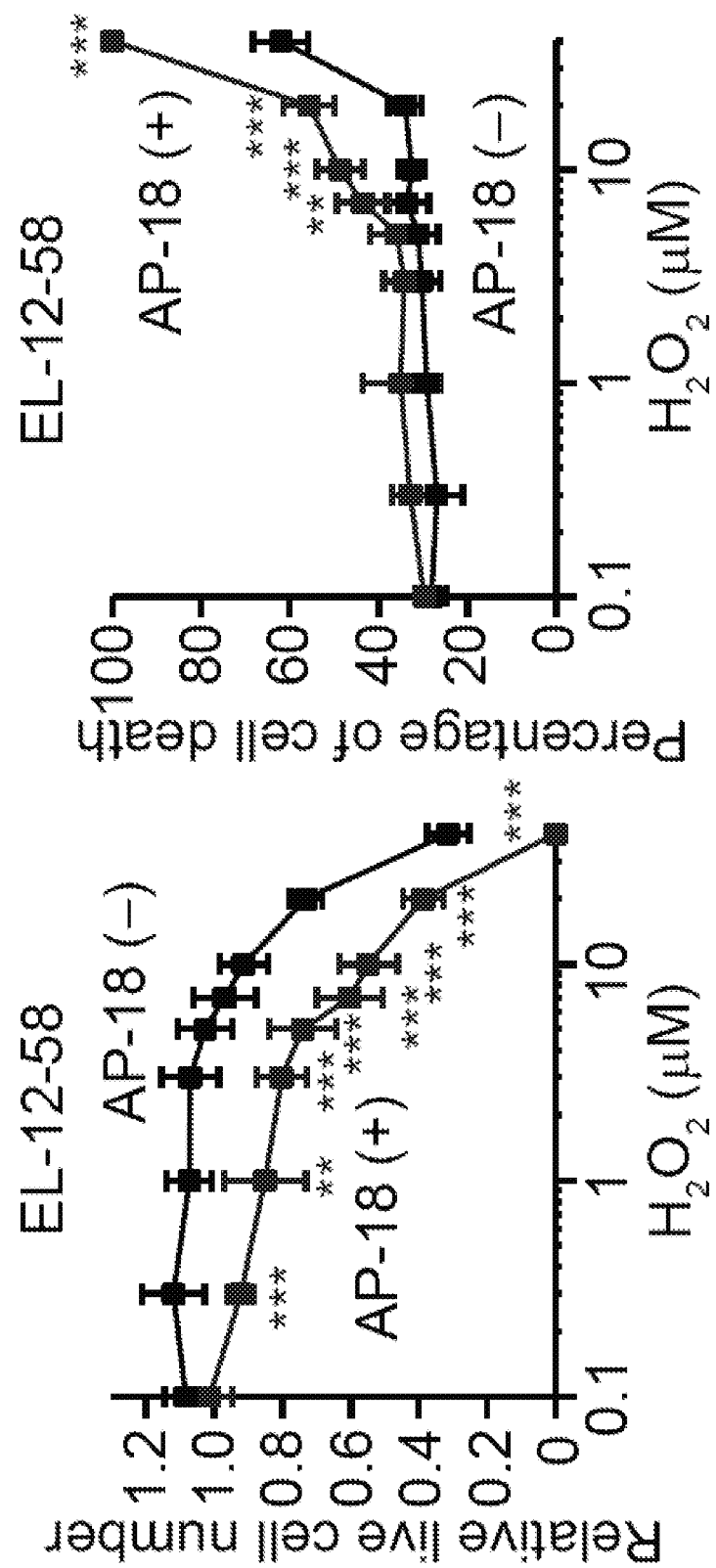
FIG. 4F is a series of graphs of live cell numbers relative to $H_2O_2$-untreated cells (left) and percentage of cell death (right) in EL-12-58 cells treated with $H_2O_2$ for 72 h in the presence or absence of 10 μM AP-18, which were calculated as in FIG. 1G. Data shown as mean±SD (n=6: the sum of three independent experiments performed in duplicate). P<0.01 and *P<0.001 compared to vehicle control for AP-18 [AP-18 (−)] (Student's t test).

We next examined the impact of shRNA-mediated TRPA1 knockdown (FIG. 4A) on $[Ca^{2+}]_i$ and cell viability under $H_2O_2$ treatment in HCC1569 cells. $H_2O_2$ caused an increase in $[Ca^{2+}]_i$ and, interestingly, also induced oscillatory $Ca^{2+}$ responses in HCC1569 cells that were largely dependent on TRPA1, as they were strongly suppressed by TRPA1 knockdown (FIGS. 4B and 4C). TRPA1 knockdown did not affect cell growth in monolayer culture (FIG. 4D) but substantially decreased live cell number and increased cell death in response to $H_2O_2$ in HCC1569 cells (FIG. 4E). Interestingly, HCC1569 cells were more sensitive to $H_2O_2$ than MCF-10A cells, suggesting that, like most cancer cells, the cellular redox status of HCC1569 cells is intrinsically more oxidative (Trachootham et al., Nat. Rev. Drug Disc., 8:579-591, 2009). Inhibition of TRPA1 with AP18 also sensitized EL-12-58 cells to $H_2O_2$ cytotoxicity (FIG. 4F). These results indicate that endogenous TRPA1 protects breast cancer cells from $H_2O_2$ insults.

Figure 4G:
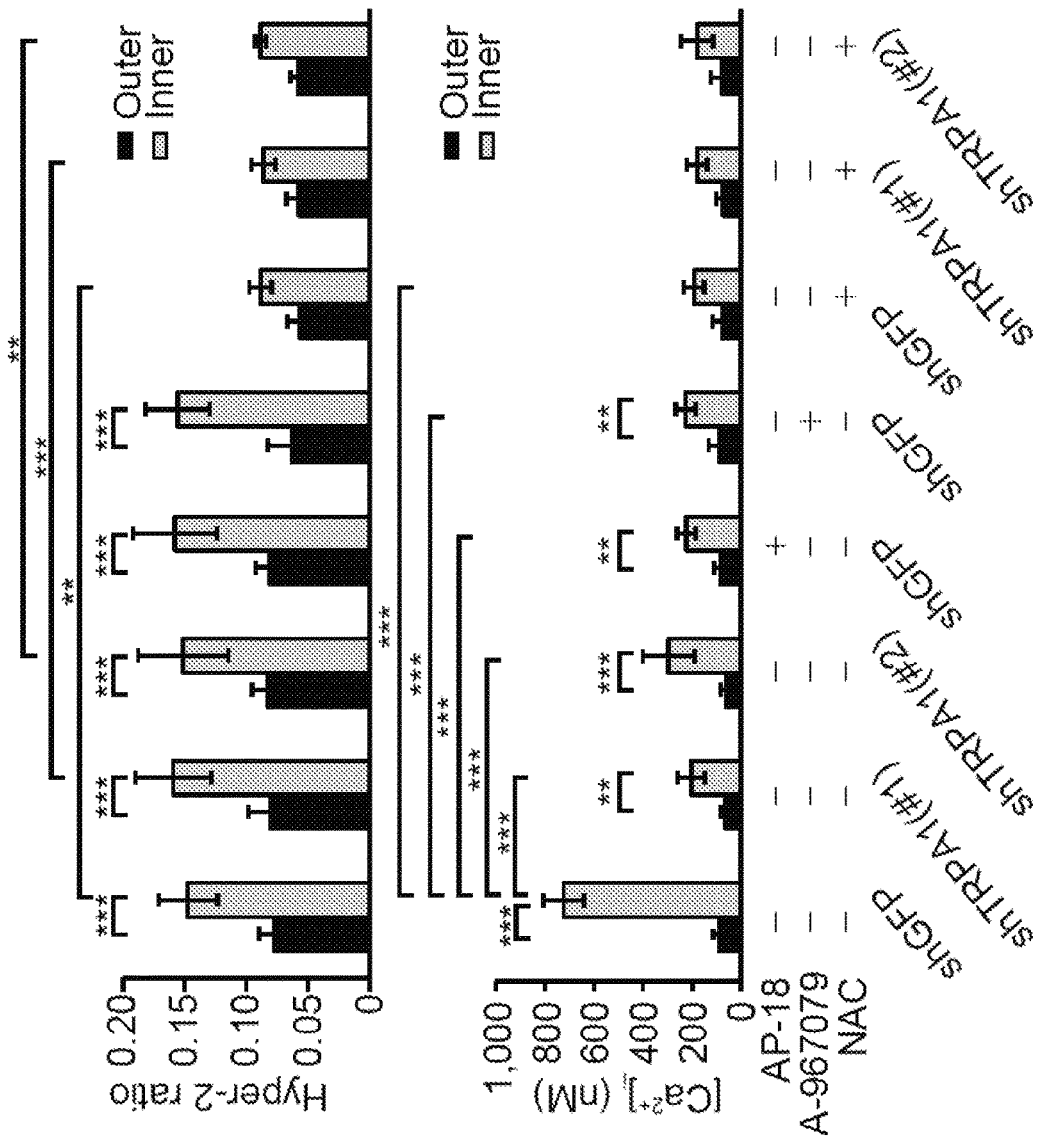
FIG. 4G is a series of graphs of the averaged Hyper-2 ratio and $[Ca^{2+}]_i$ in the inner and outer region of the spheroids treated with or without AP-18, 300 nM A-967079, or 5 mM NAC (pH was adjusted to 7.4). Data is mean±SD (n=3-11). P<0.01 and *P<0.001 (one-way ANOVA).
Figure 4H:
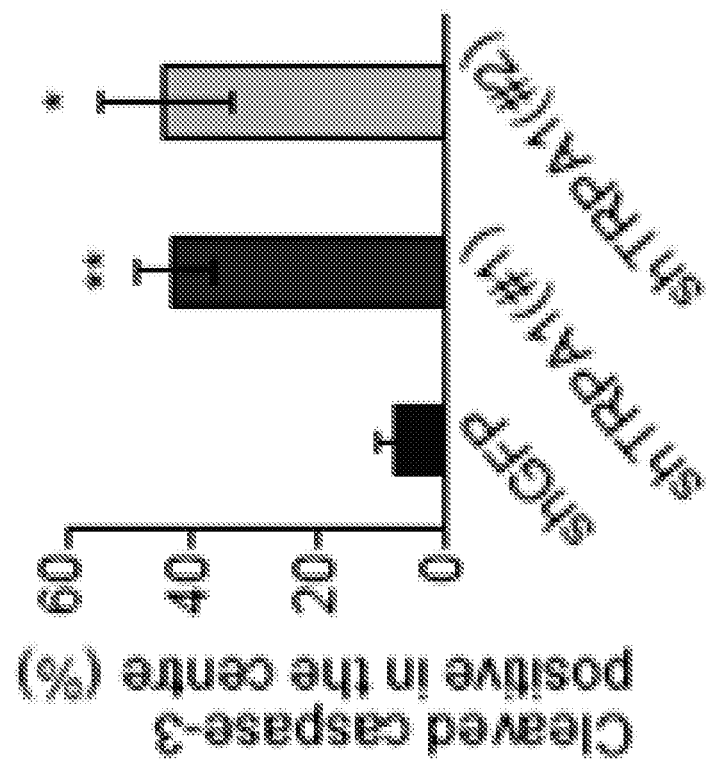
FIG. 4H is a graph of the percentage of spheroids with cleaved caspase-3 staining in the center. Data shown as mean±SEM from three independent experiments. *P<0.05 and **P<0.01 compared to shGFP (Student's t test).
Figure 4I:
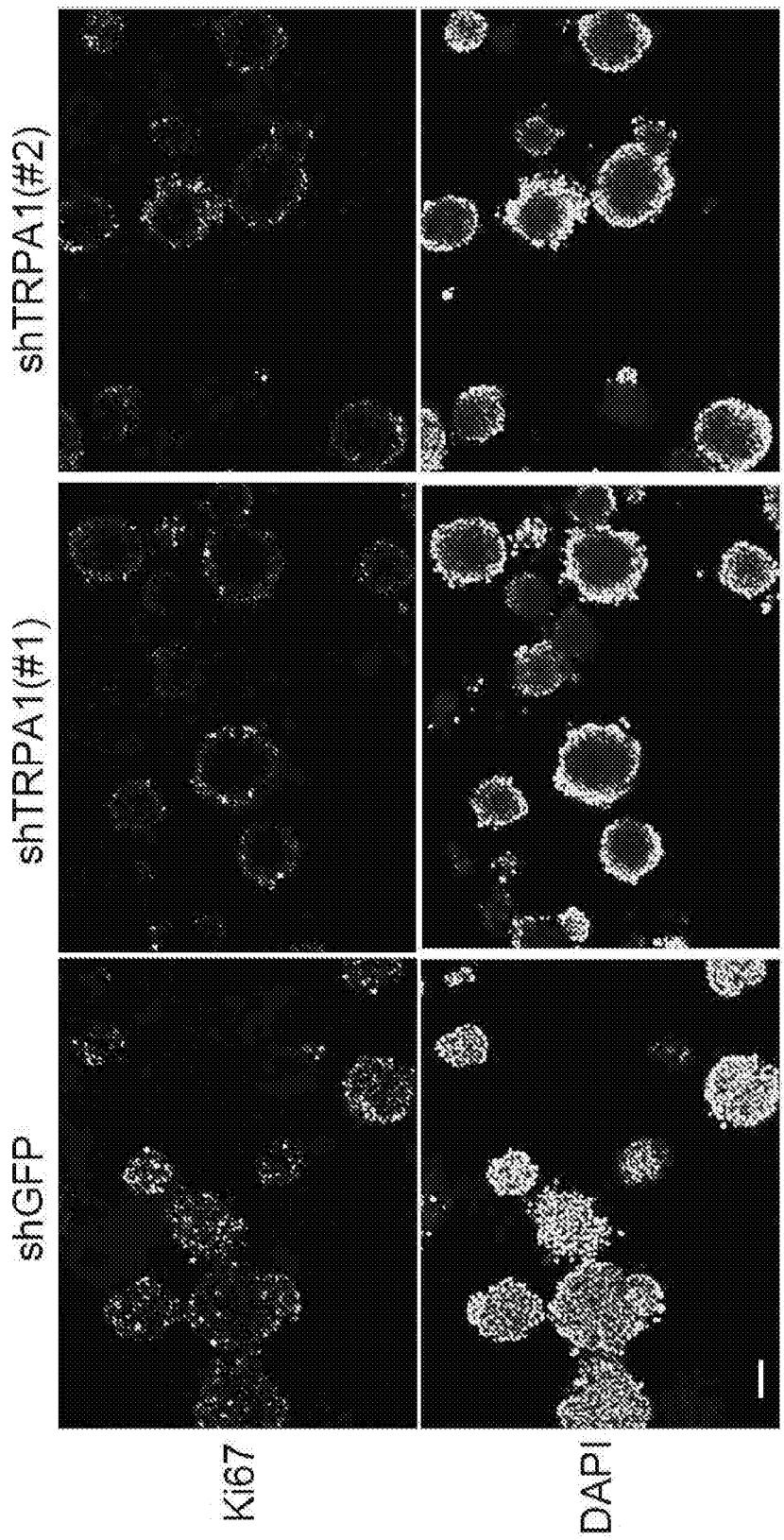
FIG. 4I is a series of photographs of representative images of day-15 spheroids stained with Ki67 and DAPI. Scale bar 100 μm.
Figures 4J, 4K:
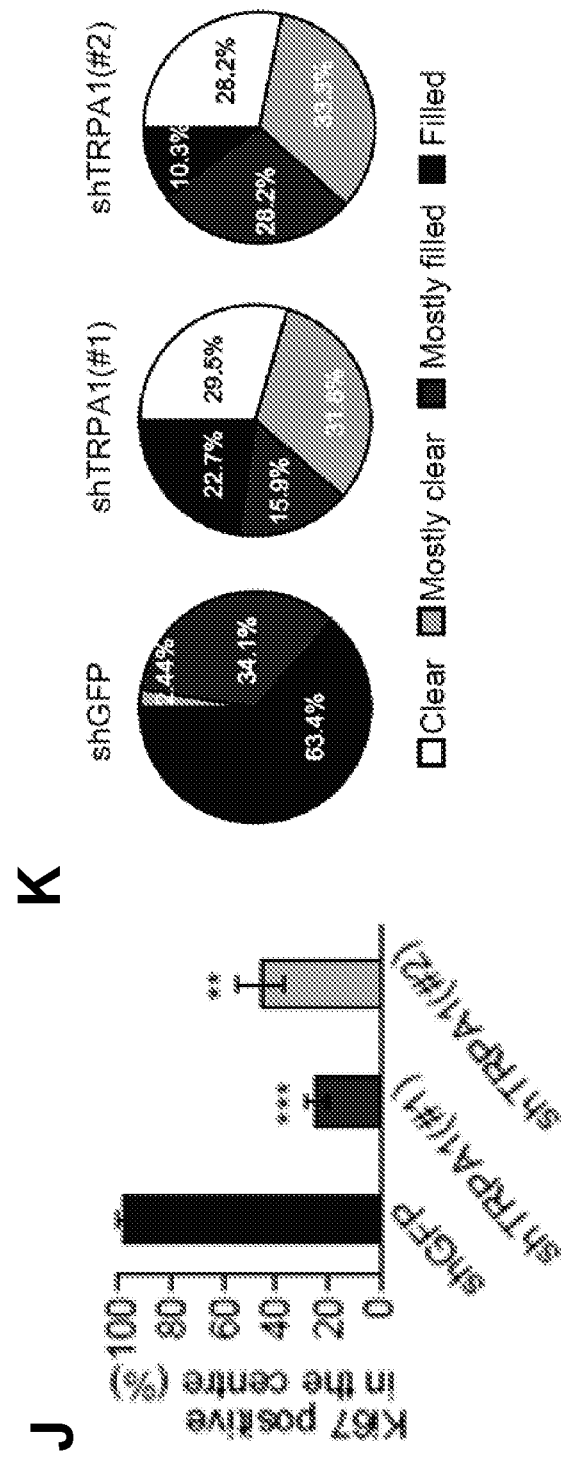
FIG. 4J is a graph of the percentage of spheroids with Ki67 staining in the center. Data is mean±SEM from three independent experiments. P<0.01 and *P<0.001 compared to shGFP (Student's t test).
FIG. 4K is a series of pie charts of clearance levels of Day-15 spheroid (n=39-44: the sum of three independent experiments).
Figure 4L:
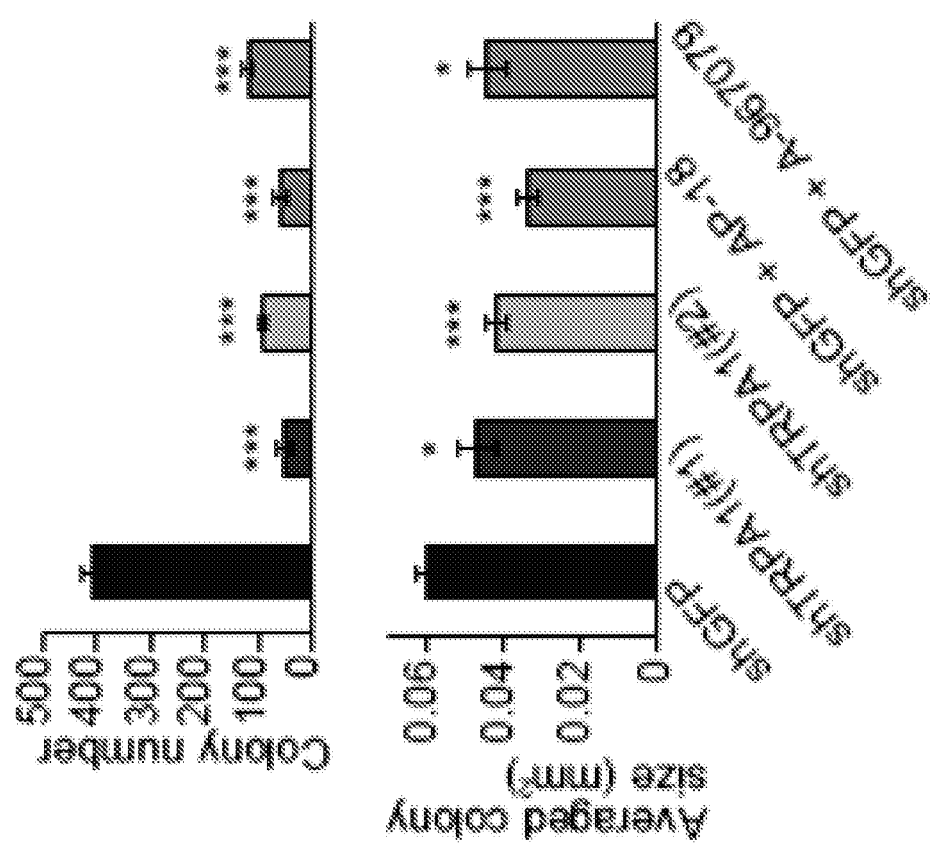
FIG. 4L is a series of graphs of colony number and averaged colony size. Data is mean±SEM of three independent experiments. *P<0.05 and ***P<0.001 compared to shGFP (Student's t test).

In 3D culture, HCC1569 cells formed filled spheroid structures that, even after days in culture, never developed a hollow lumen. Nevertheless, Hyper-2 analysis revealed that $[H_2O_2]_i$ was substantially increased in the inner region of these spheroids and this increase was unaffected by either TRPA1 knockdown, AP-18, or A-967079, but was abolished by NAC (FIG. 4G). Moreover, the inner cells showed elevated $[Ca^{2+}]_i$ that was suppressed by either TRPA1 knockdown or treatment with AP-18, A-967079, or NAC. TRPA1 knockdown prominently increased apoptosis of HCC1569 cells localized in the inner region of day 10 spheroids (FIG. 4H) and strongly induced clearance of these cells from the luminal space by day 15 (FIGS. 4I-4K). In soft agar assays, TRPA1 knockdown or treatment with either AP-18 or A-967079 impaired the anchorage-independent growth of HCC1569 cells, as demonstrated by the suppression of the number and average size of colonies (FIG. 4L). Together, these results suggest that in cells with upregulated TRPA1 expression, ROS produced as a result of matrix deprivation induce TRPA1-mediated $[Ca^{2+}]$ rises that in turn provide a survival advantage to breast cancer cells.

Figure 5A:
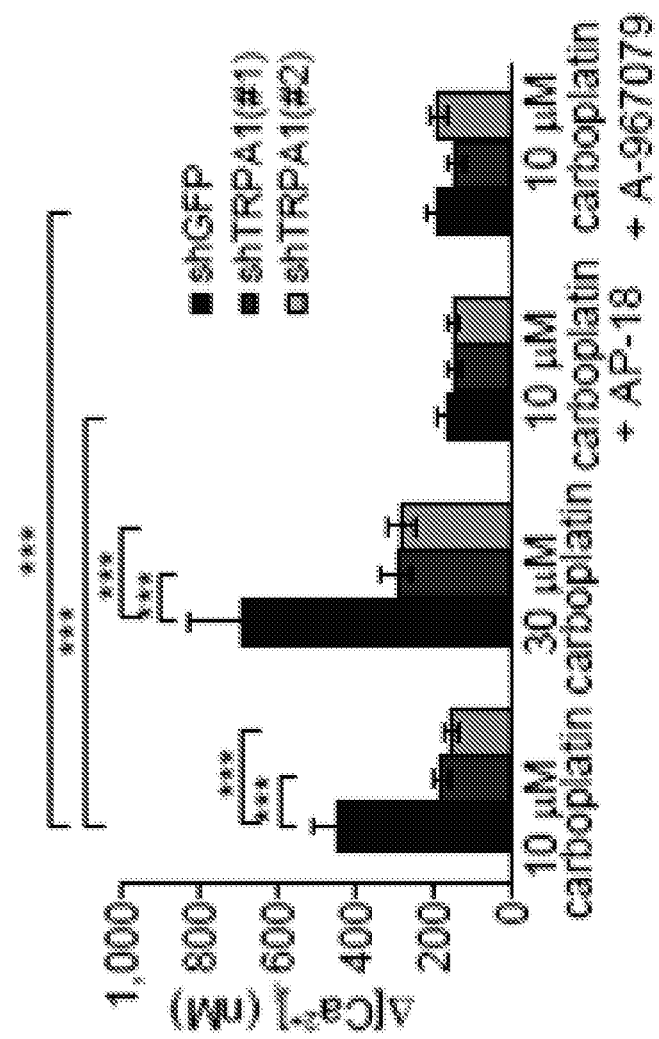
FIG. 5A is a graph of the $\Delta[Ca^{2+}]_i$, upon carboplatin treatment in HCC1569 cells transduced with shTRPA1 or shGFP in the presence or absence of 10 μM AP-18 or 300 nM A-967079. Data is mean±SEM (n=22-61). ***P<0.001 (one-way ANOVA).
Figure 5B:
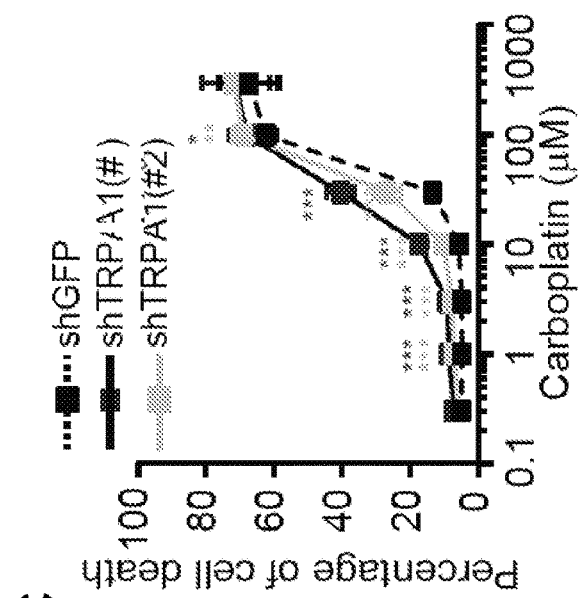
FIG. 5B is a graph of the frequency of $Ca^{2+}$ transient ($\Delta[Ca^{2+}]_i$>200 nM) in HCC1569 cells transduced with shRNA against TRPA1 or GFP and treated with or without carboplatin in the presence or absence of 10 μM AP-18 or 300 nM A-967079. Data shown as mean±SEM (n=34-151). ***P<0.001 (one-way ANOVA).
Figure 5C:
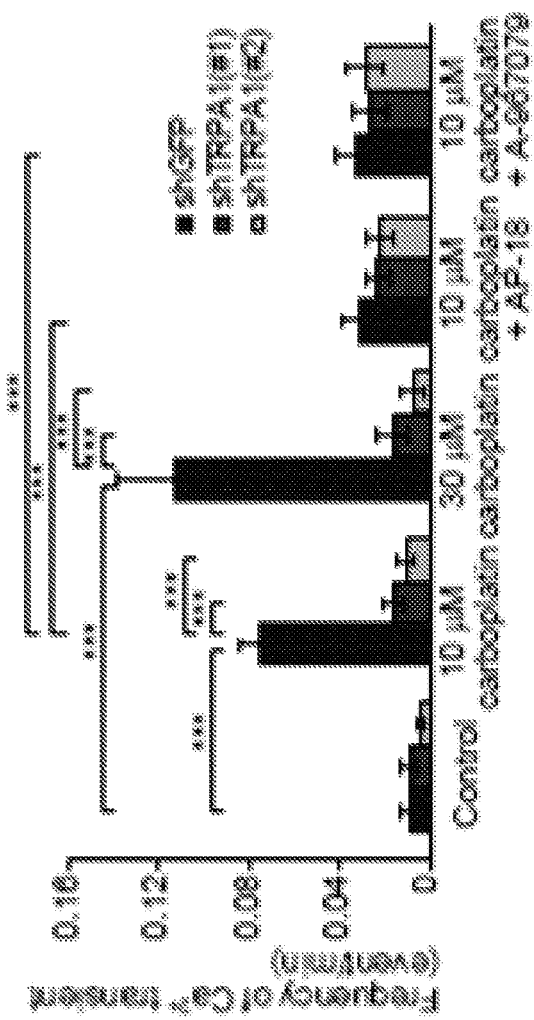
FIG. 5C is a graph of the percentage of cell death in HCC1569 cells transduced with shGFP or shTRPA1 and treated with carboplatin for 72 h, which was calculated as in FIG. 1G. Data shown as mean±SD (n=6: the sum of three independent experiments performed in duplicate). *P<0.05, P<0.01, and *P<0.001 compared to shGFP (Student's t test).
Figure 5D:
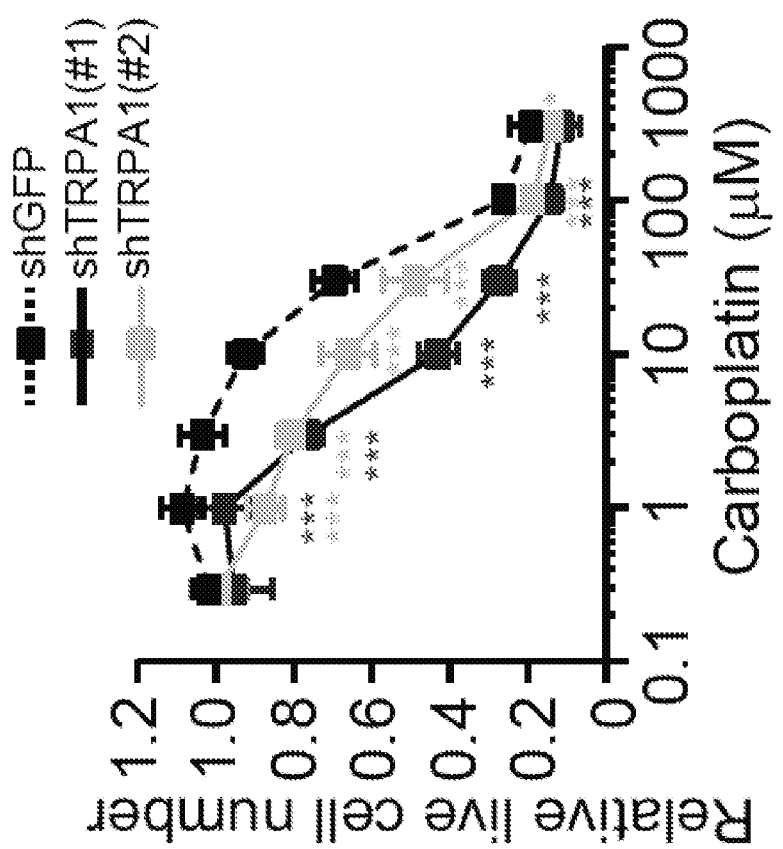
FIG. 5D is a graph of live cell numbers in the indicated HCC1569 cells treated with carboplatin for 72 h. Data is mean±SD (n=6: the sum of three independent experiments performed in duplicate). *P<0.05 and ***P<0.001 compared to shGFP (Student's t test). Live cell numbers are calculated as in FIG. 1G and are expressed relative to chemotherapy-untreated cells.
Figure 5E:
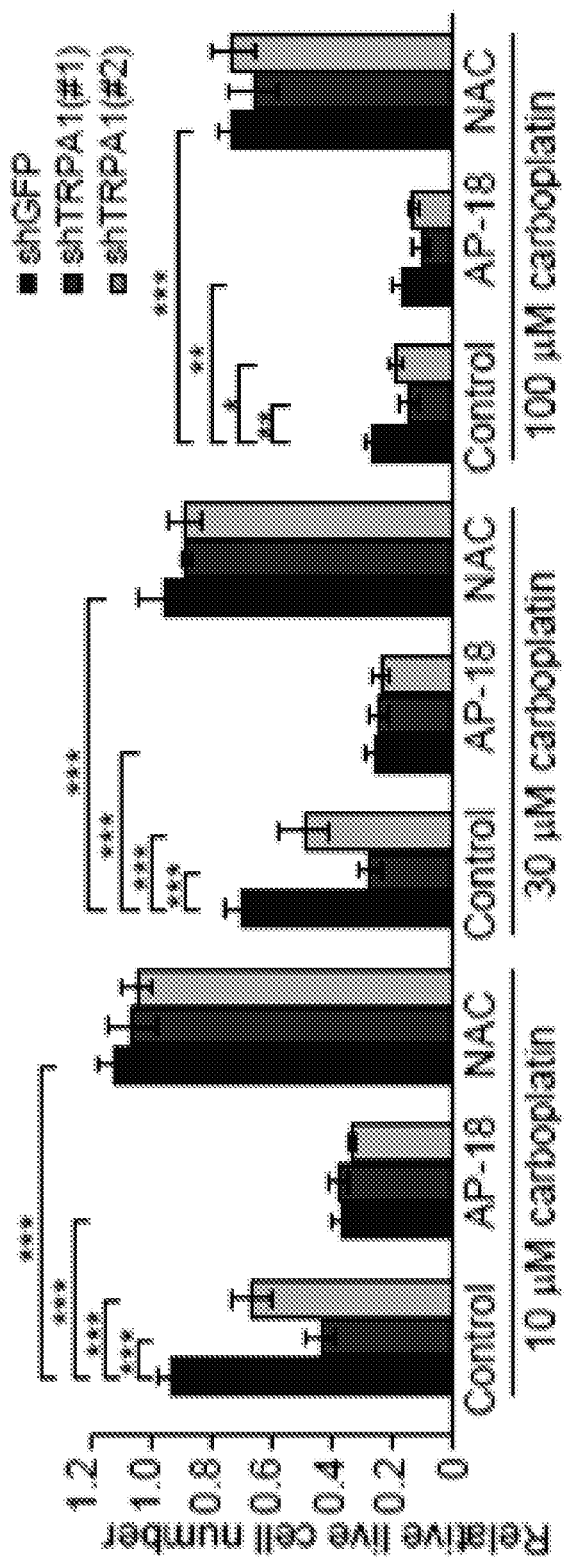
FIG. 5E is a series of graphs of live cell numbers in the indicated HCC1569 cells treated with carboplatin in the presence or absence of 10 μM AP-18 or 5 mM NAC (pH was adjusted to 7.4) for 72 h. Data is mean±SD (n=4-6: the sum of two or three independent experiments performed in duplicate). *P<0.05, P<0.01, and *P<0.001 (one-way ANOVA). Live cell numbers are calculated as in FIG. 1G and are expressed relative to chemotherapy-untreated cells.
Figure 5F:
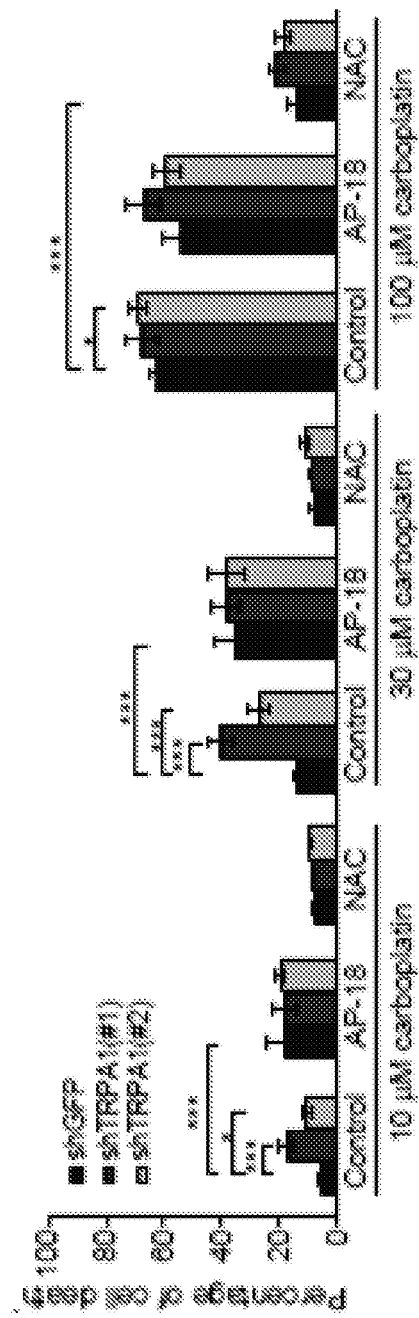
FIG. 5F is a series of graphs of the percentage of cell death in HCC1569 cells transduced with shGFP or shTRPA1 and treated with carboplatin in the presence or absence of 10 μM AP-18 or 5 mM NAC (pH was adjusted to 7.4) for 72 h, which was calculated as in FIG. 1G. Data shown as mean±SD (n=4-6: the sum of two or three independent experiments performed in duplicate). *P<0.05 and ***P<0.001 (one-way ANOVA).
Figures 5G, 5H:
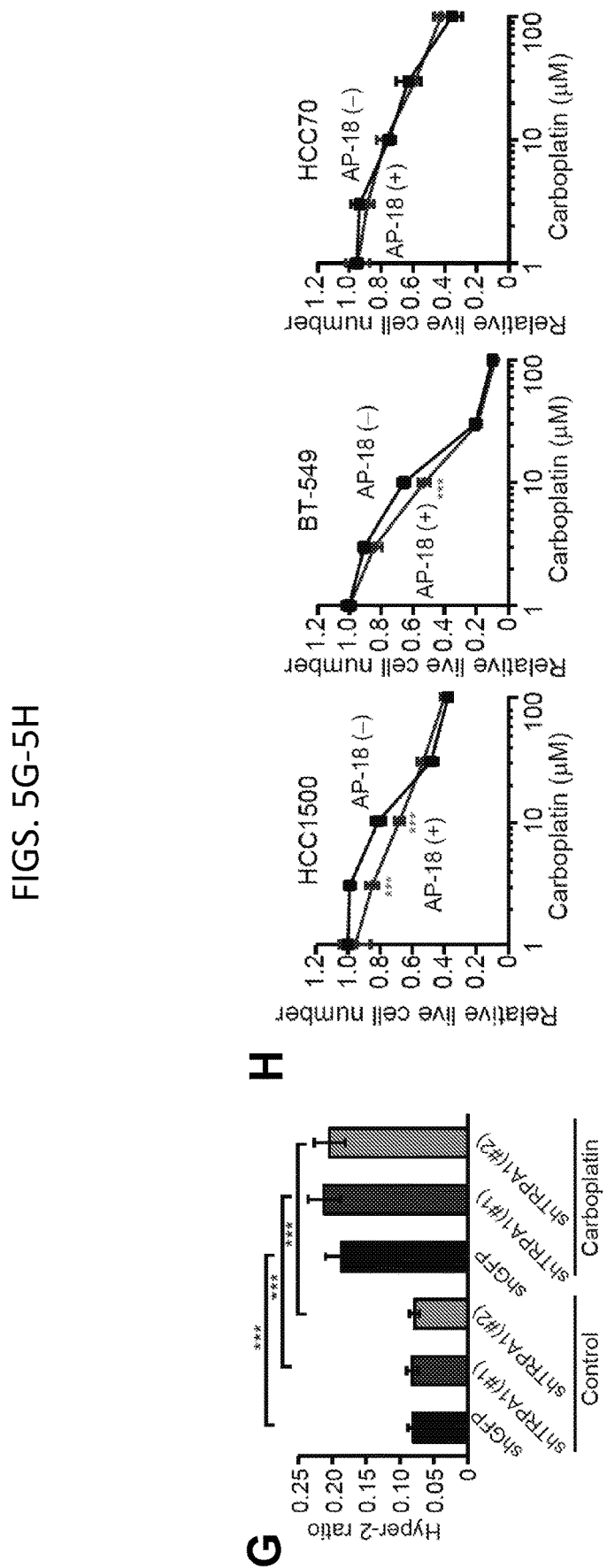
FIG. 5G is a graph of the averaged Hyper-2 ratio in the indicated HCC1569 cells treated with or without 30 μM carboplatin for 48 h. Data shown as mean±SD (n=106-233). ***P<0.001 (one-way ANOVA).
FIG. 5H is a series of graphs of live cell numbers relative to carboplatin-untreated cells in the indicated breast cancer cells upon treatment with carboplatin for 72 h in the presence or absence of 10 μM AP-18, which were calculated as in FIG. 1G. Data shown as mean±SD (n=4: the sum of two independent experiments performed in duplicate). ***P<0.001 compared to vehicle control for AP-18 [AP-18 (−)] (Student's t test).
Figure 5I:
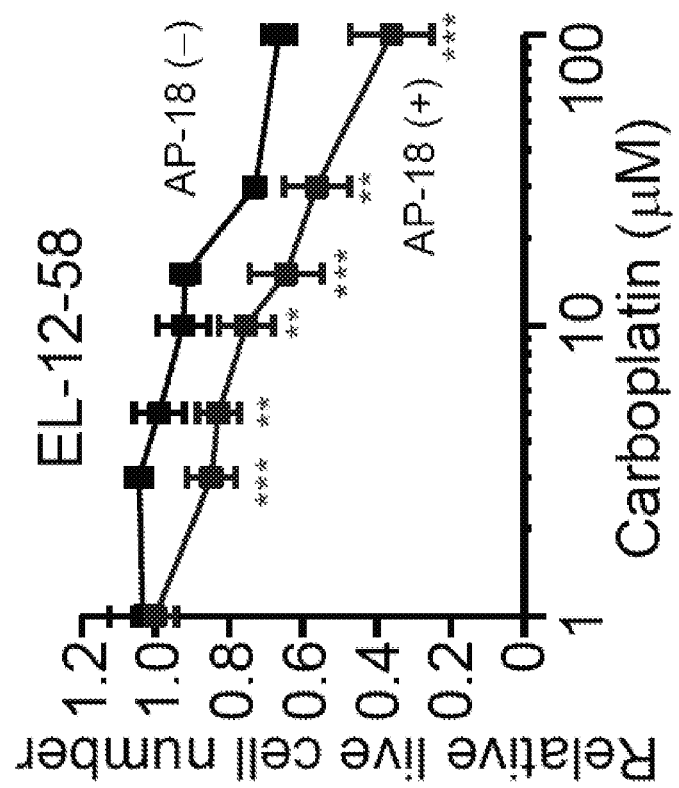
FIG. 5I is a graph of live cell numbers in EL-12-58 cells treated with carboplatin in the presence or absence of 10 μM AP-18 for 72 h. Data is mean±SD (n=6: the sum of three independent experiments performed in duplicate). P<0.01 and *P<0.001 compared to vehicle control for AP-18 [AP-18 (−)] (Student's t test). Live cell numbers are calculated as in FIG. 1G and are expressed relative to chemotherapy-untreated cells.

Example 7: TRPA1 Confers Therapy Resistance on Breast and Lung Cancer and MPNST Cells We investigated the effects of TRPA1 expression on carboplatin sensitivity. In HCC1569 cell treated with carboplatin, TRPA1 knockdown or treatment with either AP-18 or A-967079 significantly suppressed both $[Ca^{2+}]_i$ rises and oscillatory $Ca^{2+}$ responses (FIGS. 5A and 5B), and substantially suppressed live cell number and enhanced cell death in response to carboplatin treatment (FIGS. 5C-5F). Carboplatin-induced ROS generation was unaffected by TRPA1 knockdown (FIG. 5G), indicating that TRPA1 promotes carboplatin resistance through a mechanism distinct from antioxidant programs. TRPA1-mediated chemoresistance was largely eliminated by NAC (FIGS. 5E and 5F), suggesting that TRPA1 activation by carboplatin (either directly through its electrophilic binding to the channel or indirectly through ROS production) is involved in the chemoresistance of HCC1569 cells. AP-18 also sensitized the EL-12-58 breast cancer PDX-derived cell line which displays comparable TRPA1 expression to HCC1569 cells, but had minimal to no effect on HCC1500, BT-549 and HCC70, which express very low levels of TRPA1 (FIGS. 5H and 5I).

Figure 5J:
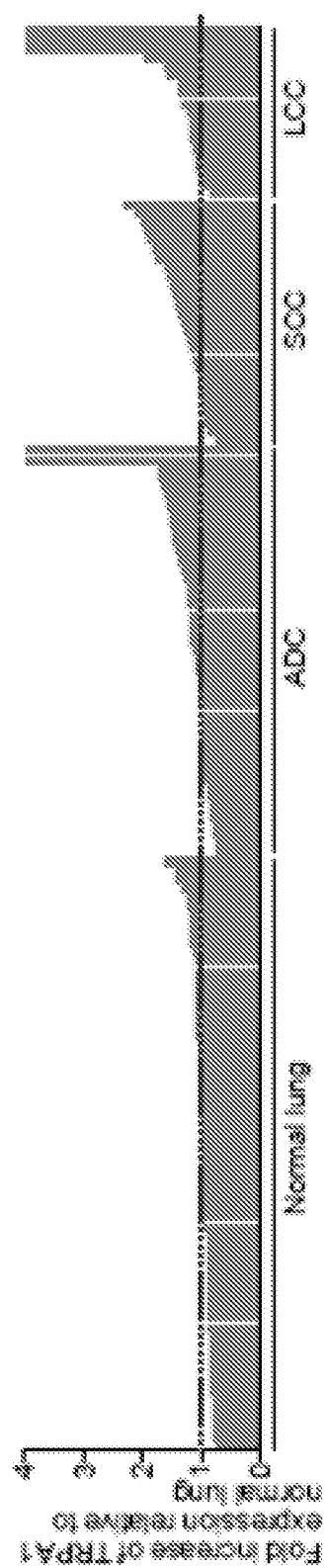
FIG. 5J is a schematic of a waterfall plot displaying fold increases of TRPA1 mRNA expression in NSCLCs relative to normal lung tissues, using published microarray data sets. The vertical axis of the graph is cut off at 4.
Figures 5K, 5L:
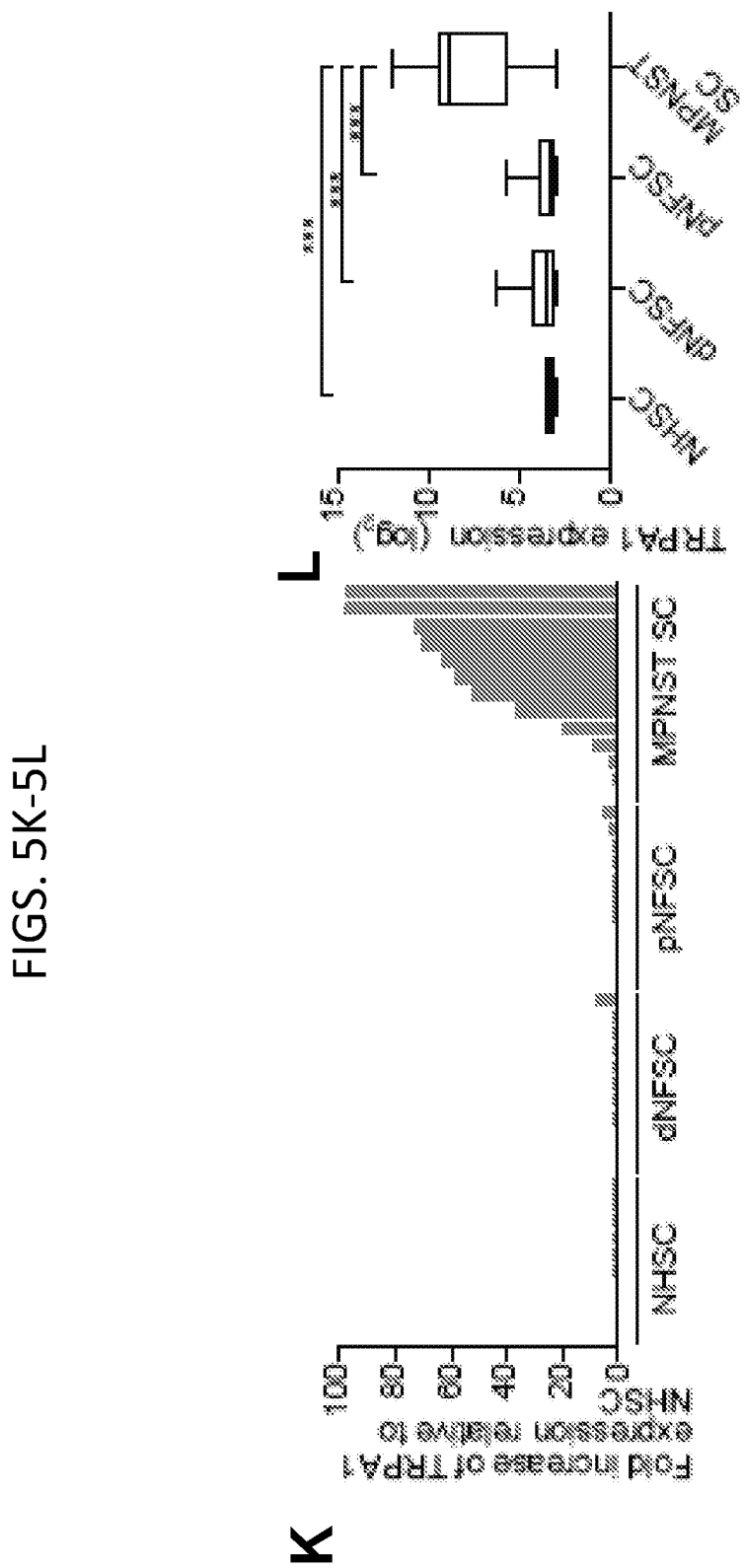
FIG. 5K is a schematic of a waterfall plot displaying fold increases of TRPA1 mRNA expression in dermal and plexiform NF1-derived primary benign neurofibroma Schwann cells (dNFSCs and pNFSCs, respectively) and MPNST Schwann cells (MPNST SC) relative to normal human Schwann cells (NHSC), using published microarray data sets (Miller et al., EMBO Mol. Med.: 236-248, 2009). The vertical axis of the graph is cut off at 100.
FIG. 5L is a series of box plots displaying TRPA1 mRNA levels in NHSC (n=10), dNFSC (n=11), pNFSC (n=11), and MPNST SC (n=13).
Figure 5M:
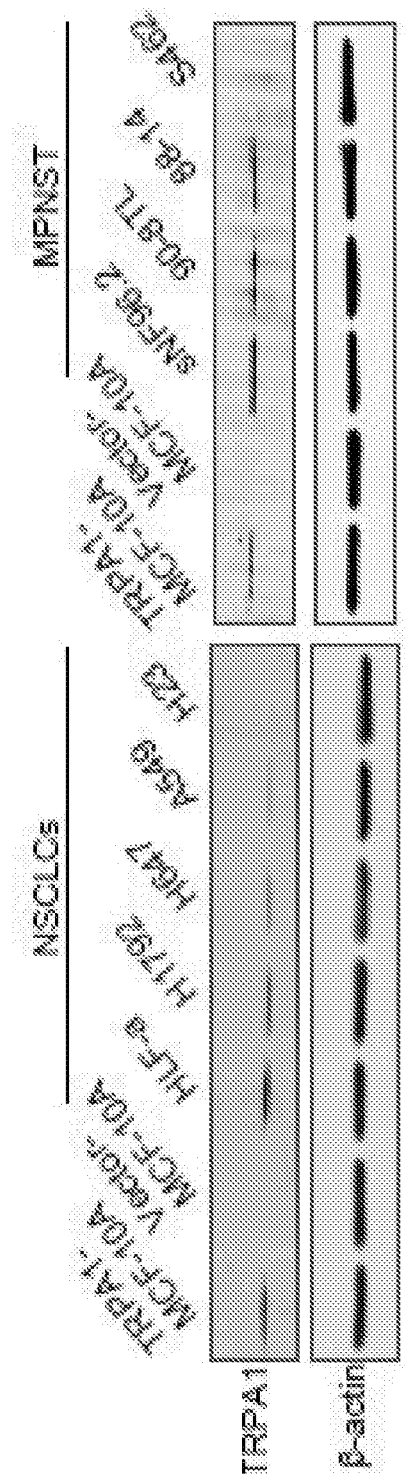
FIG. 5M is a series of photographs of immunoblot analyses of TRPA1 in the indicated NSCLC and MPNST cell lines.
Figure 5N:
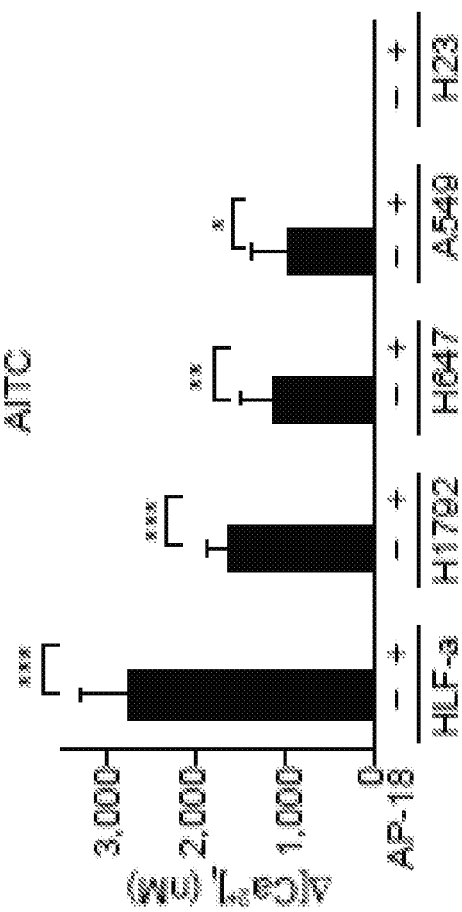
FIG. 5N is a graph of averaged time courses of $\Delta[Ca^{2+}]_i$ evoked by 30 μM AITC in the indicated NSCLC cells treated with or without 10 μM AP-18. Data shown as mean±SEM (n=21-60). *P<0.05, P<0.01, and *P<0.001.
Figure 50:
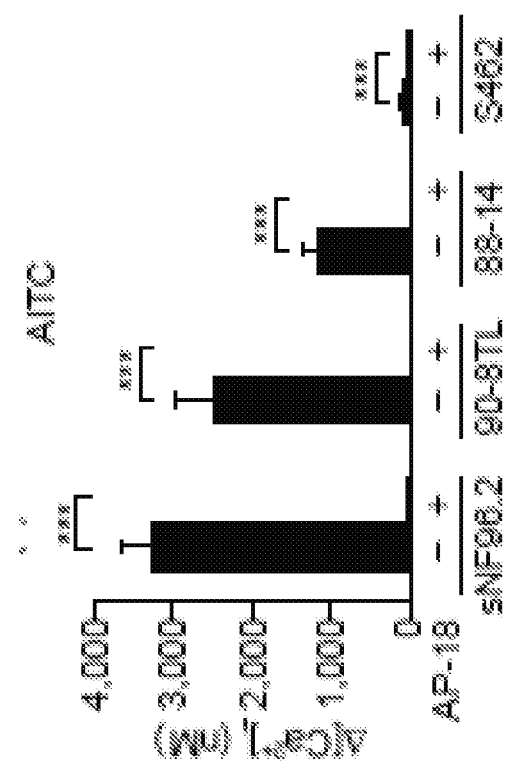
Figure 5P:
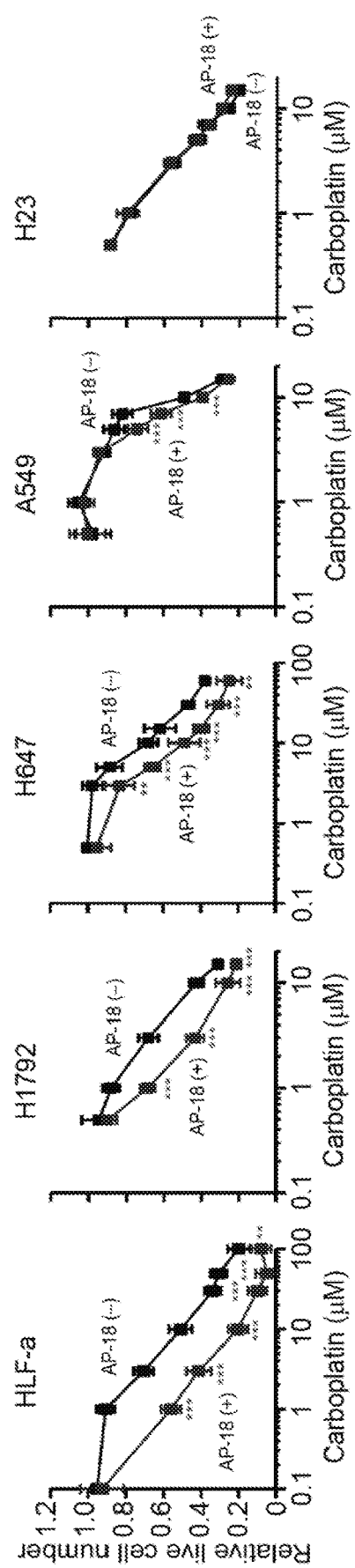
FIG. 5P is a series of graphs of live cell numbers in NSCLC cells treated with carboplatin in the presence or absence of 10 μM AP-18 for 72 h. Data is mean±SD (n=6: the sum of three independent experiments performed in duplicate). *P<0.05, P<0.01, and *P<0.001 compared to AP-18 (−) (Student's t test). Live cell numbers are calculated as in FIG. 1G and are expressed relative to chemotherapy-untreated cells.
Figure 5Q:
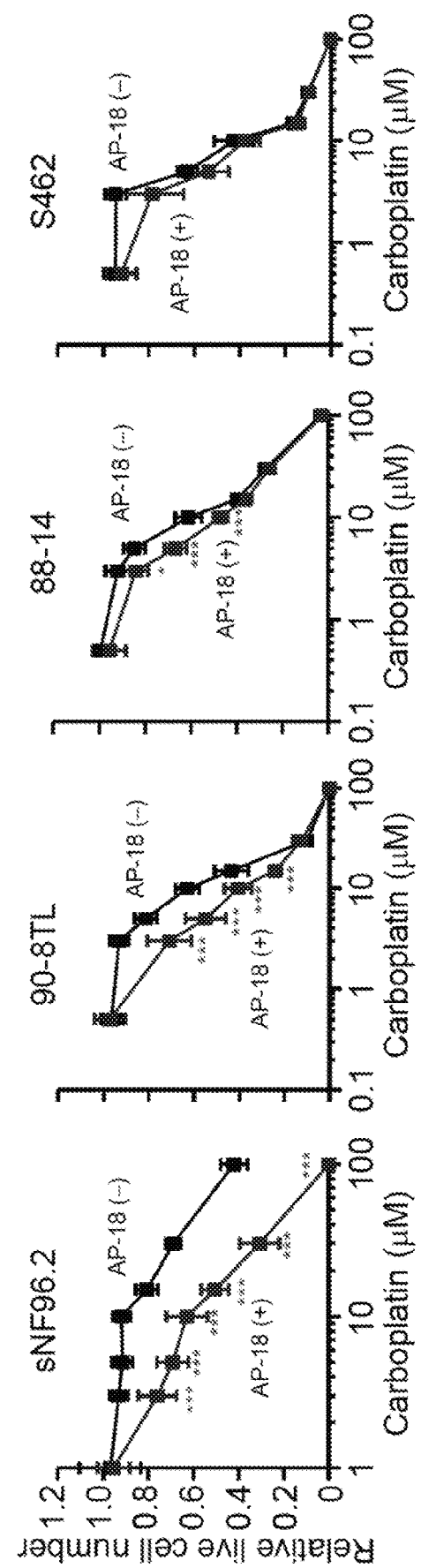
FIG. 5Q is a series of graphs of live cell numbers in MPNST cells treated with carboplatin in the presence or absence of 10 μM AP-18 for 72 h. Data is mean±SD (n=6: the sum of three independent experiments performed in duplicate). *P<0.05, P<0.01, and *P<0.001 compared to AP-18 (−) (Student's t test). Live cell numbers are calculated as in FIG. 1G and are expressed relative to chemotherapy-untreated cells.

In addition to breast cancer cell lines, we also examined the effects of TRPA1 in lung cancer and malignant peripheral nerve sheath tumor (MPNST) cells, as TRPA1 is upregulated in non-small cell lung cancers (NSCLCs), including adenocarcinomas (ADC), squamous cell carcinoma (SCC), and large cell carcinoma (LCC), and is highly upregulated in MPNST (FIGS. 5J-5L). Immunoblot analysis revealed that TRPA1 expression is enriched in a subset of NSCLC cell lines [very high: HLF-a (SCC); high: H1792 (ADC); moderate: H647 (adenosquamous carcinoma); low: A549 (ADC); negative: H23 (ADC)] and MPNST cell lines (very high: sNF96.2; high: 90-8TL and 88-14; negative: S462) (FIG. 5M). AITC induced robust $[Ca^{2+}]_i$ rises that were abolished by AP-18 in TRPA1-enriched NSCLC and MPNST cells (FIGS. 5N and 5O), indicating that TRPA1 is functional in these cell lines. Moreover, AP-18 sensitized NSCLC and MPNST cells to $H_2O_2$— and carboplatin-induced cytotoxicity in a TRPA1 expression-dependent manner (FIGS. 5M-5O).

Figure 5R:
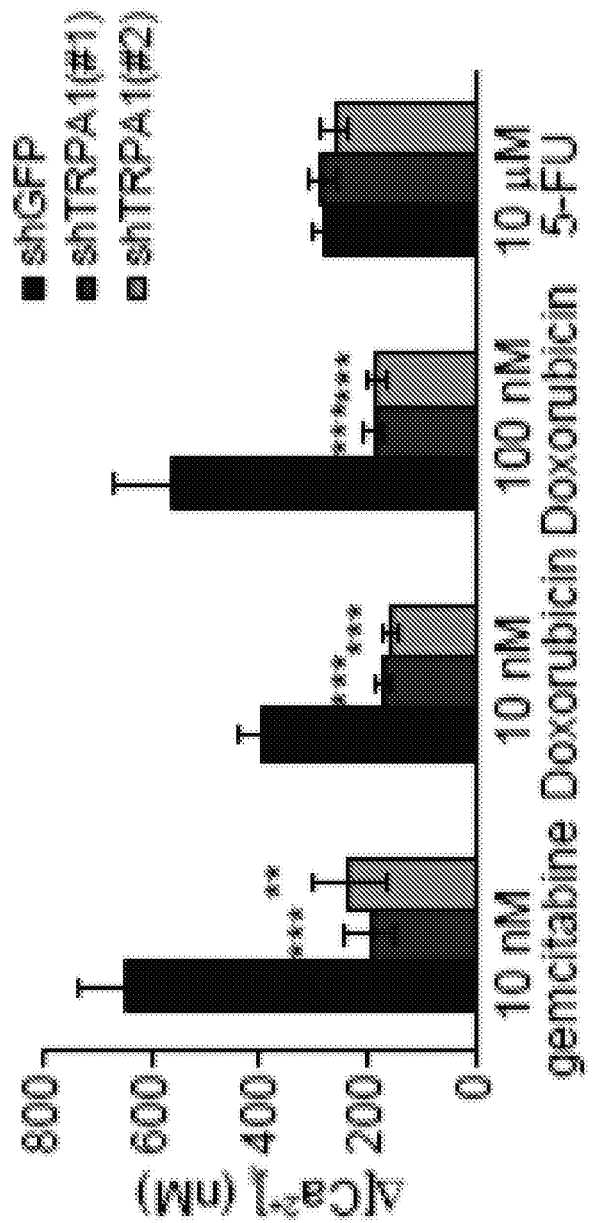
FIG. 5R is a graph of $\Delta[Ca^{2+}]_i$ upon treatment with the indicated chemotherapies. Data is mean±SEM (n=26-62). P<0.01 and *P<0.001 compared to shGFP (Student's t test).
Figure 5S:
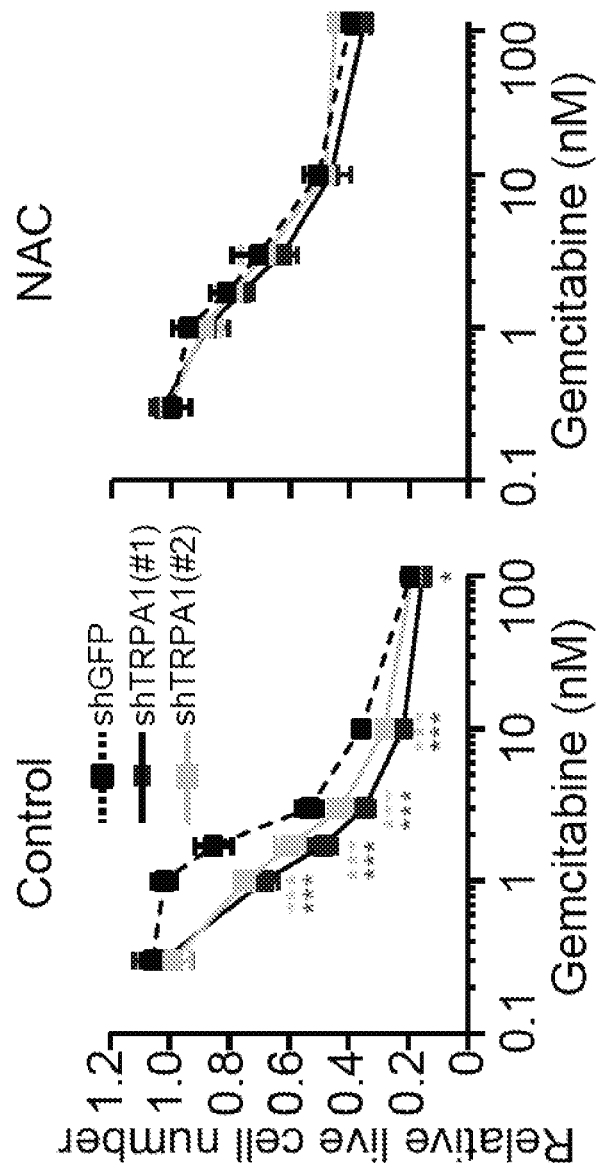
FIG. 5S is a series of graphs of live cell numbers in the indicated HCC1569 cells treated with gemcitabine in the presence or absence of 5 mM NAC (pH was adjusted to 7.4) for 72 h. Data is mean±SD (n=4-6: the sum of two or three independent experiments performed in duplicate). *P<0.05 and ***P<0.001 compared to shGFP (Student's t test). Live cell numbers are calculated as in FIG. 1G and are expressed relative to chemotherapy-untreated cells.
Figure 5T:
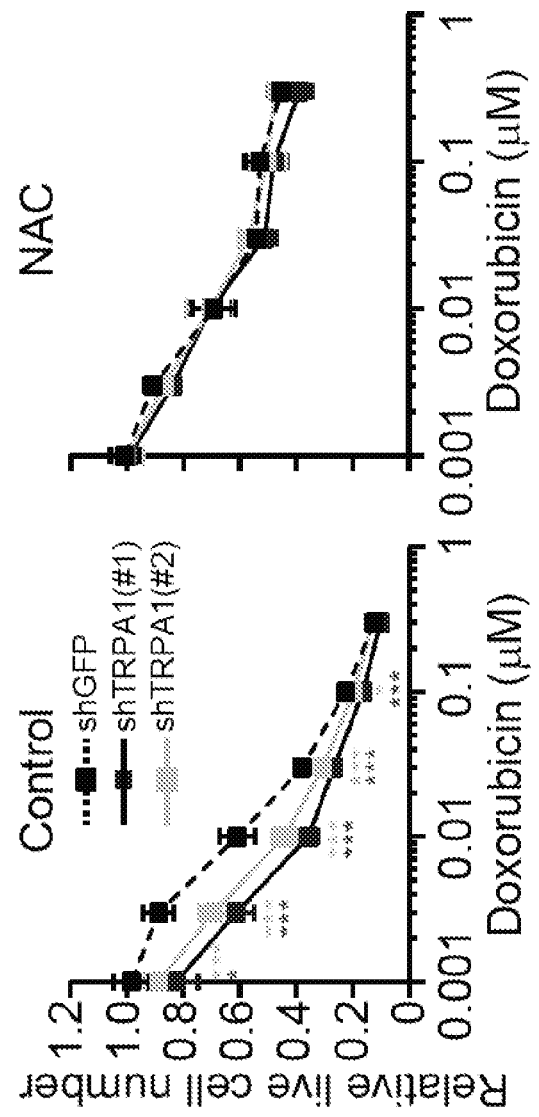
FIG. 5T is a series of graphs of live cell numbers in the indicated HCC1569 cells treated with doxorubicin in the presence or absence of 5 mM NAC (pH was adjusted to 7.4) for 72 h. Data is mean±SD (n=4-6: the sum of two or three independent experiments performed in duplicate). *P<0.05 and ***P<0.001 compared to shGFP (Student's t test). Live cell numbers are calculated as in FIG. 1G and are expressed relative to chemotherapy-untreated cells.
Figure 5U:
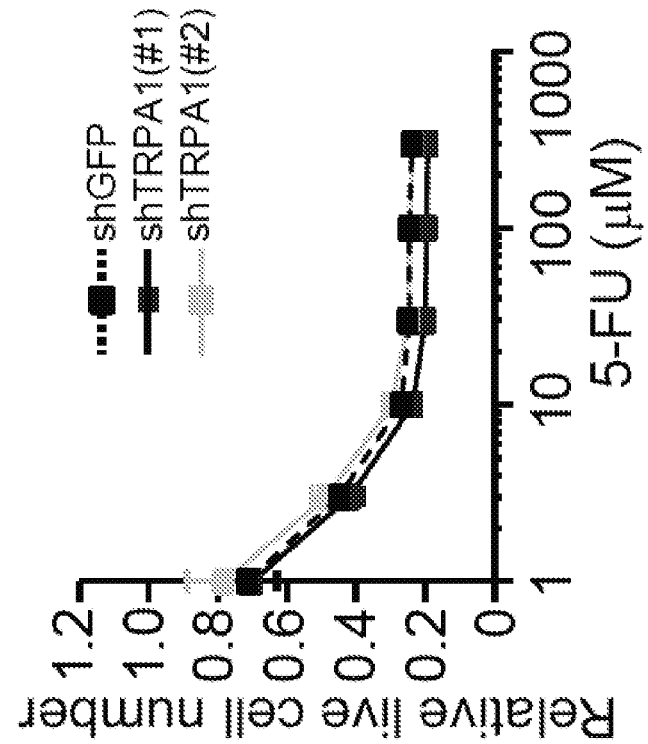
FIG. 5U is a graph of live cell numbers in the indicated HCC1569 cells treated with 5-FU in the presence or absence of 5 mM NAC (pH was adjusted to 7.4) for 72 h. Data is mean±SD (n=4-6: the sum of two or three independent experiments performed in duplicate). *P<0.05 and ***P<0.001 compared to shGFP (Student's t test). Live cell numbers are calculated as in FIG. 1G and are expressed relative to chemotherapy-untreated cells.

Given the fact that many standard-of-care therapies induce high levels of oxidative stress that causes apoptosis, we investigated whether other ROS-associated chemotherapies, such as gemcitabine, doxorubicin, and 5-Fluorouracil (5-FU), induce TRPA1 activation and whether this activation allows breast cancer cells to adapt to chemotherapy. TRPA1 knockdown significantly suppressed both $[Ca^{2+}]_i$ rises and oscillatory $Ca^{2+}$ responses induced by gemcitabine and doxorubicin, but not by 5-FU, in HCC1569 cells (FIG. 5R). Accordingly, TRPA1 knockdown sensitized HCC1569 cells to gemcitabine and doxorubicin, but not 5-FU, and this effect was eliminated by NAC (FIGS. 5S-5U).

Figure 6A:
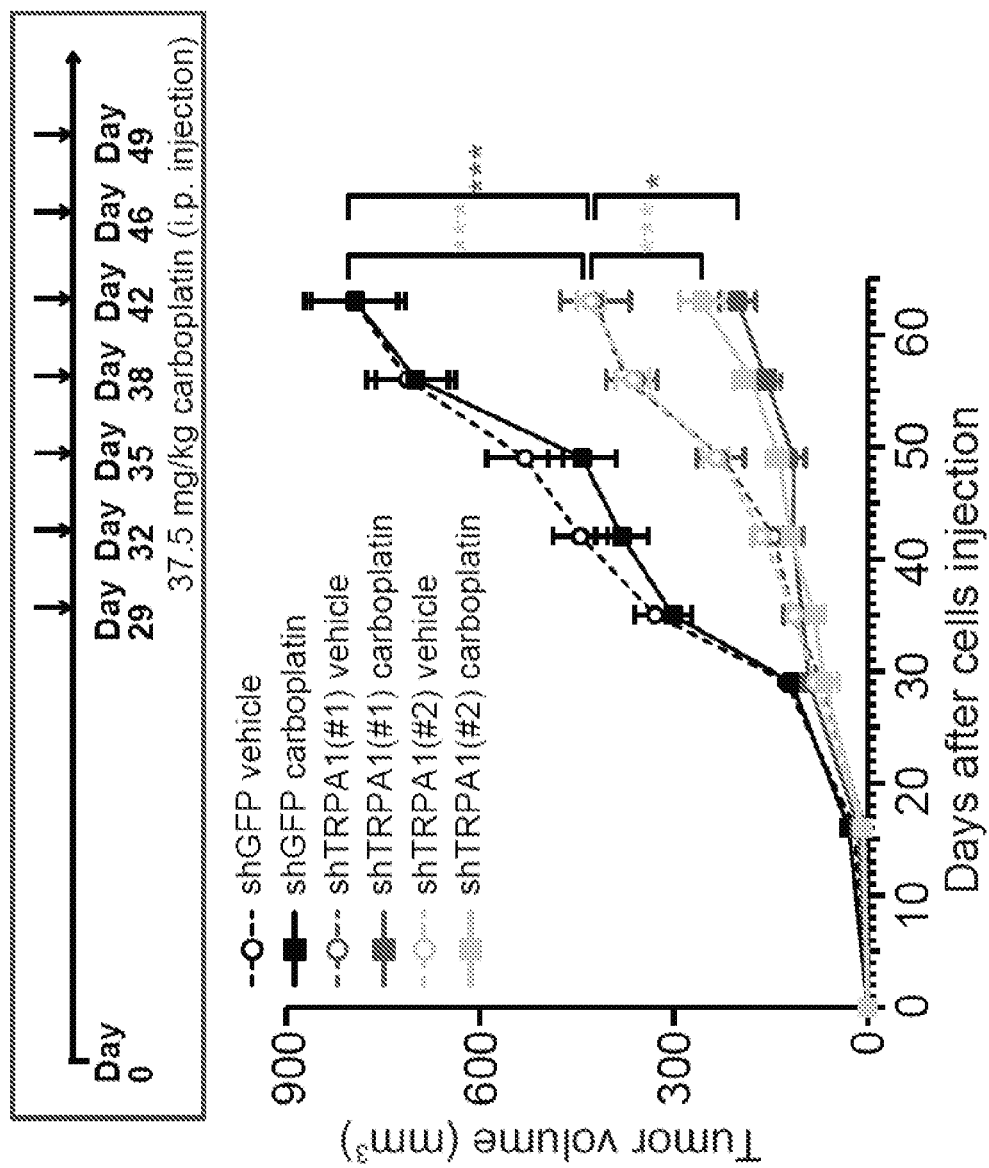
FIG. 6A is a schematic (top) and graph (bottom) of tumor growth of shGFP- or shTRPA1-transduced HCC1569 cells injected into cleared mammary fat pads of NRG mice, represented as mean tumor volume (mm$^3$)±SEM, was monitored over time (n=7-9). Carboplatin (solid lines) or vehicle (dotted lines) was administered twice a week from Days 29 to 49. *P<0.05 and ***P<0.001 (two-way ANOVA).
Figure 6B:
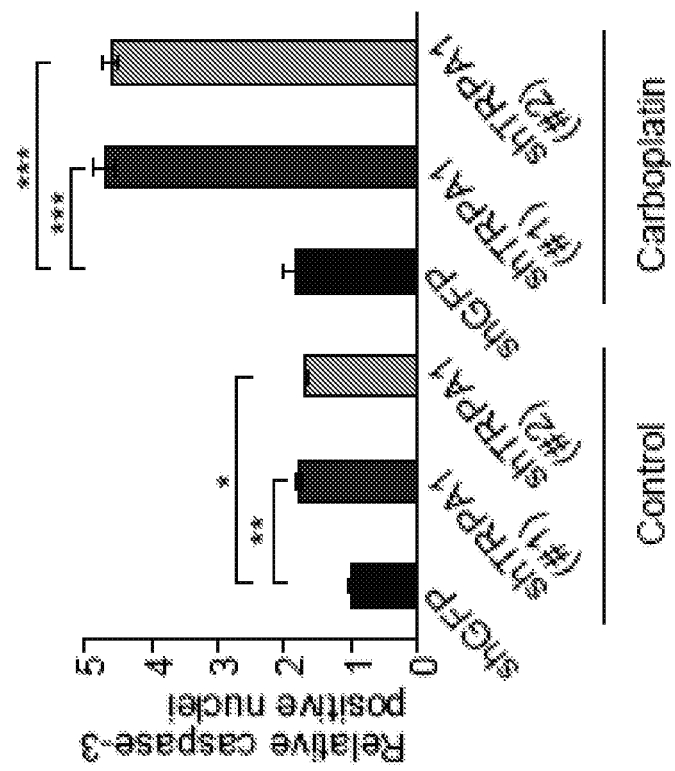
FIG. 6B is a graph of the quantification of cleaved caspase-3-positive nuclei. Data are normalized to shGFP-expressing tumors treated with vehicle and shown as mean±SEM (n=3-9). *P<0.05, P<0.01, and P<0.001 (one-way ANOVA).

Example 8: TRPA1 Regulates Tumor Growth and Chemoresistance in a Breast Xenograft Tumor Model To investigate whether TRPA1 contributes to tumor growth and chemoresistance in vivo, HCC1569 cells stably expressing TRPA1 shRNAs were transplanted into cleared mammary fat pads of immunocompromised NOD-Rag1$^{null}$ IL2rg$^{null}$ (NRG) mice and tumor growth was measured. TRPA1 knockdown substantially suppressed tumor growth (compare vehicle controls, FIG. 6A), suggesting that TRPA1 promotes tumorigenesis in vivo. Carboplatin was intraperitoneally injected at the indicated time points (FIG. 6A). Tumors expressing shGFP (control) were resistant to carboplatin, which is consistent with the observation that HCC1569 cells display relatively pronounced resistance to cisplatin among 893 cancer cell lines (Resistance rank: 45$^{th}$, z-score: 1.54) based on the Genomics of Drug Sensitivity in Cancer database (www.cancerrxgene.org). In contrast, tumors expressing either shTRPA1 vector displayed significant reduction in tumor growth after carboplatin treatment. This reduction in tumor growth was associated with increased apoptosis, as assessed by cleaved caspase-3 staining of tumor sections (FIG. 6B). Together, these data demonstrate that TRPA1 can contribute to tumor growth and carboplatin resistance in a xenograft model.

Figure 7A:
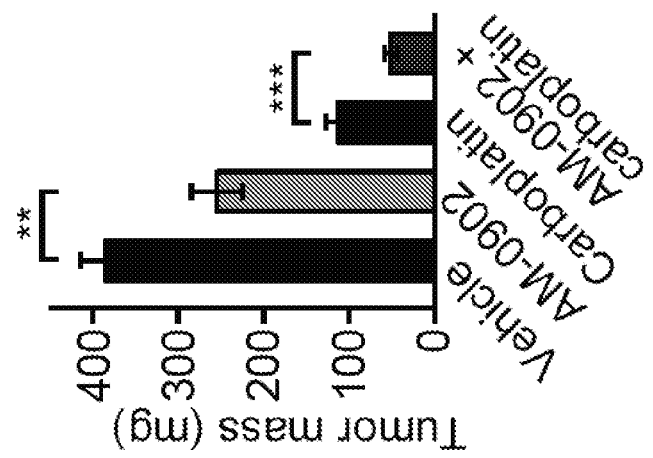
FIG. 7A is a schematic (top) and graph (bottom) of tumor growth of EL-12-58 cells injected into cleared mammary fat pads of NRG mice (n=10 for each arm). AM-0902, carboplatin, or vehicle was administered at the time schedule as described in the figure. *P<0.05 (two-way ANOVA).
Figure 7B:
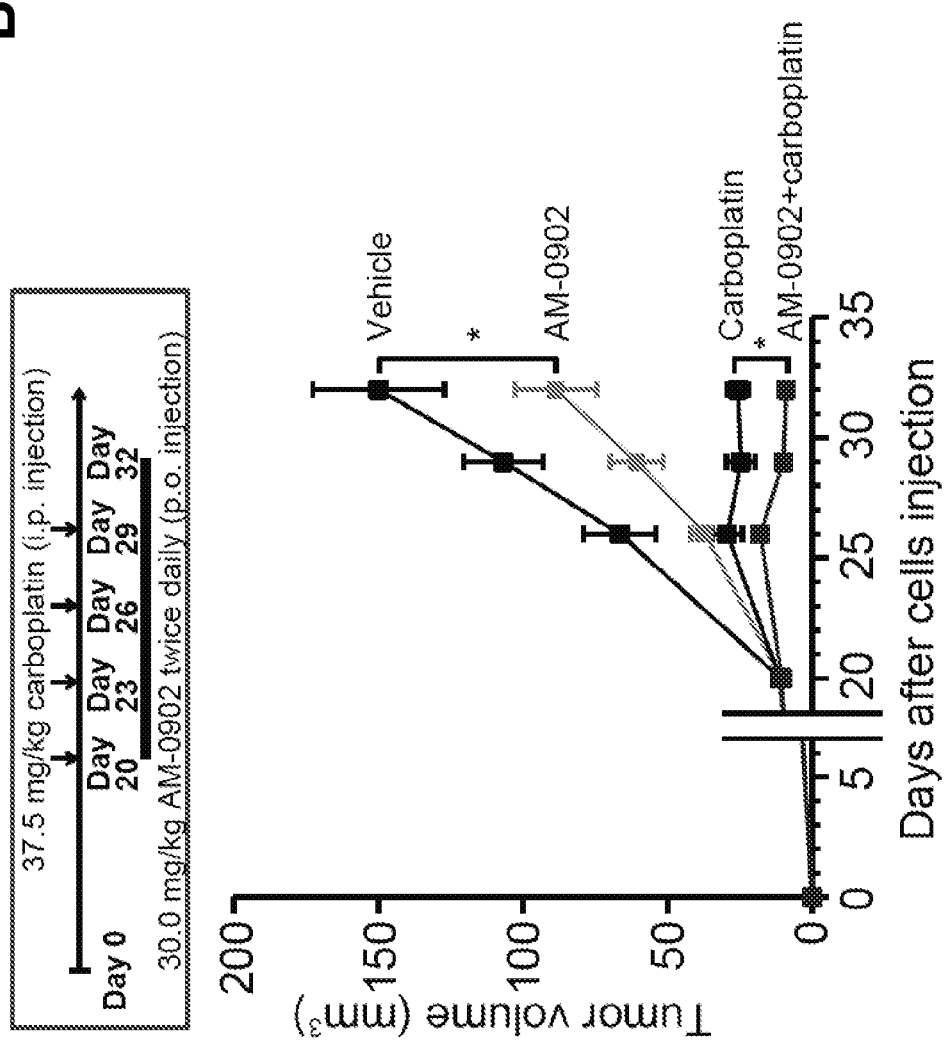
FIG. 7B is a graph of the tumor weight at the end point. P<0.01 and *P<0.001 (Student's t test).
Figure 7C:
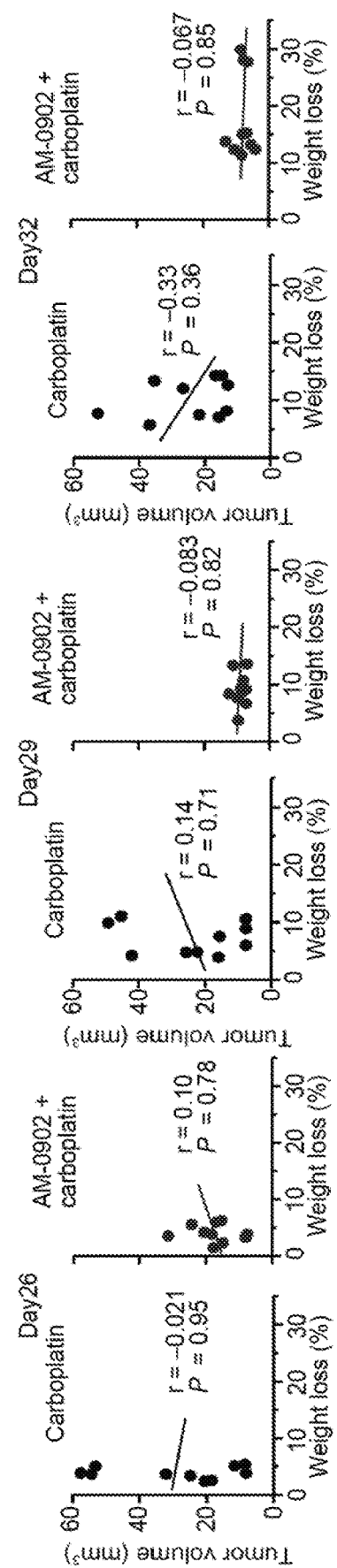
FIG. 7C is a series of graphs of correlation of weight loss (%) with tumor volume (mm$^3$) in EL-12-58 xenograft tumors treated with carboplatin (n=10) or AM-0902+carboplatin (n=10) at the indicated time points. Averaged weight loss: day 26, 3.94±1.02% for carboplatin and 4.20±1.52% for carboplatin+AM-0902; day 29, 7.01±2.80% for carboplatin and 9.07±2.94% for carboplatin+AM-0902; day 32, 10.3±3.36% for carboplatin and 17.6±7.45% for carboplatin+AM-0902. Data are shown as mean±SD.
Figures 7D, 7E:
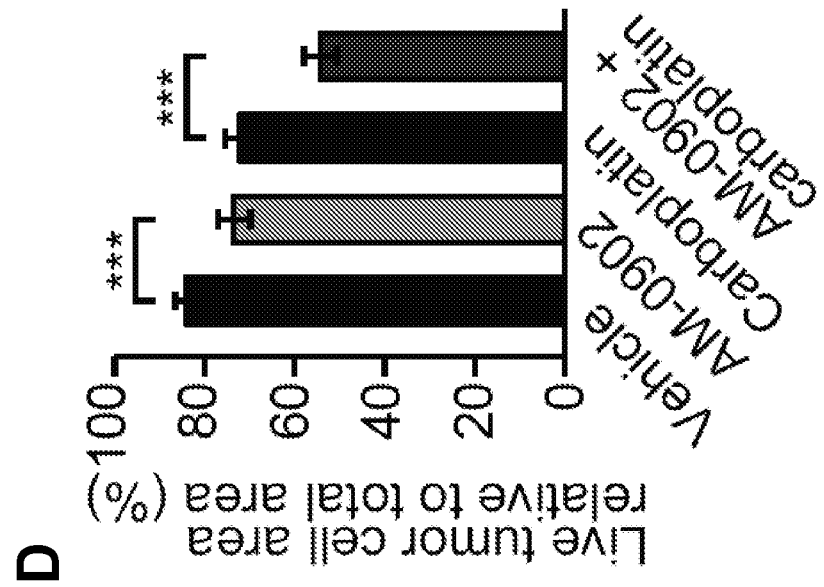
FIG. 7D is a graph of quantification of live tumor cell area relative to total area. Data are shown as mean±SD (n=5 for each arm). ***P<0.001 (Student's t test).
FIG. 7E is a graph of quantification of collagenous stroma area relative to total area. Data are shown as mean±SD (n=5 for each arm). ***P<0.001 (Student's t test).

We next examined the effect of pharmacological TRPA1 inhibition on tumor growth in a PDX model. While numerous types of TRPA1 inhibitors have been developed as novel pain and respiratory therapies, their pharmacokinetics are not optimal. We used an oral bioactive TRPA1 inhibitor, AM-0902, which has the best pharmacokinetics reported to date, but still exhibits a short plasma half-life ($T_{1/2}$=2.8 h). Despite this limitation, oral administration of AM-0902 twice daily reduced both tumor volume and mass in EL-12-58 xenograft models without significant side toxicities (0.188±2.42% weight loss at day 32) (FIGS. 7A and 7B). Moreover, combined administration of AM-0902 and carboplatin substantially reduced tumor growth and mass, compared with each single treatment. Although 3/10 animals treated with AM-0902+carboplatin exhibited significant weight loss during the last three days (from Day 29 to Day 32), most likely due to diarrhea, animals treated with either AM-0902+carboplatin or carboplatin alone showed comparable weight loss until day 29 and there was no correlation between weight loss and tumor growth at any time points (FIG. 7C). H&E staining of tumor sections revealed that AM-0902 treatment reduced live tumor cell area relative to total area, compared with vehicle or single carboplatin treatment (FIG. 7D). Furthermore, Masson trichrome staining showed that the population of collagenous stroma was enhanced by AM-0902+carboplatin treatment (FIG. 7E), probably because dead tumor cells were replaced by stroma due to a desmoplastic response.

Example 9: TRPA1 Expression in Tumor Cells is Regulated by the ROS-Activated Transcription Factor, NRF2

Figure 8A:
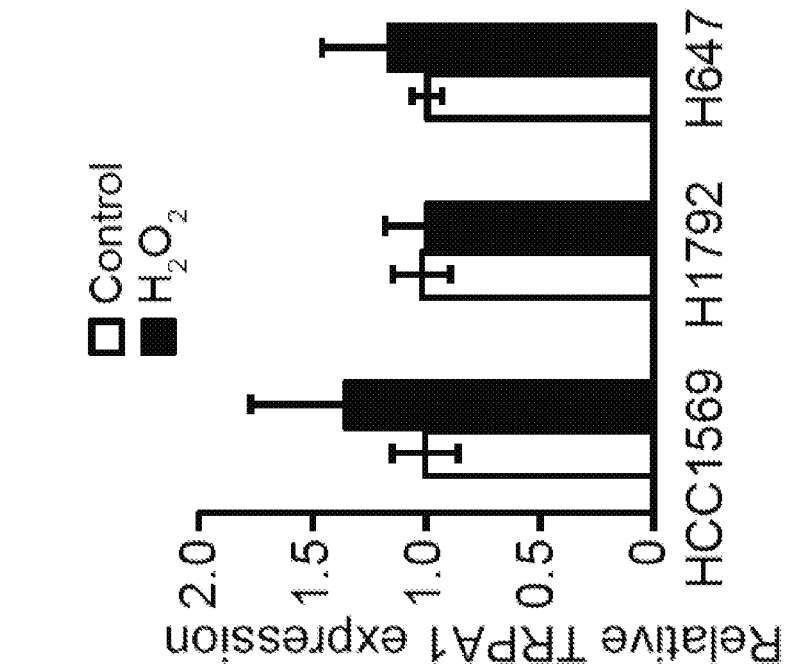
FIG. 8A is a graph of mRNA expression of TRPA1 in H358 or BT-549 cells treated with or without 10 μM H$_2$O$_2$ for 48 h in serum-starved conditions. Data were normalized to vehicle control. Data are shown as mean±SD of three independent experiments. ***P<0.001 (Student's t test).
Figure 8B:
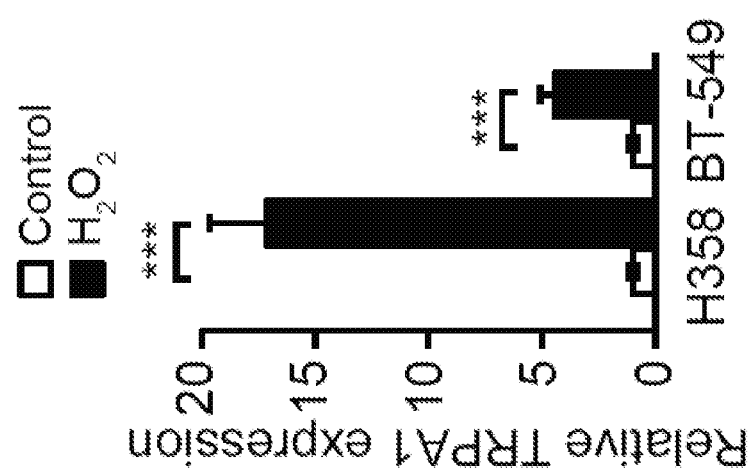
FIG. 8B is a graph of mRNA expression of TRPA1 in HCC1569, H1792, or H647 cells treated with or without 10 μM H$_2$O$_2$ for 48 h in serum-starved conditions. Data were normalized to vehicle control. Data are shown as mean±SD of three independent experiments.
Figure 8C:
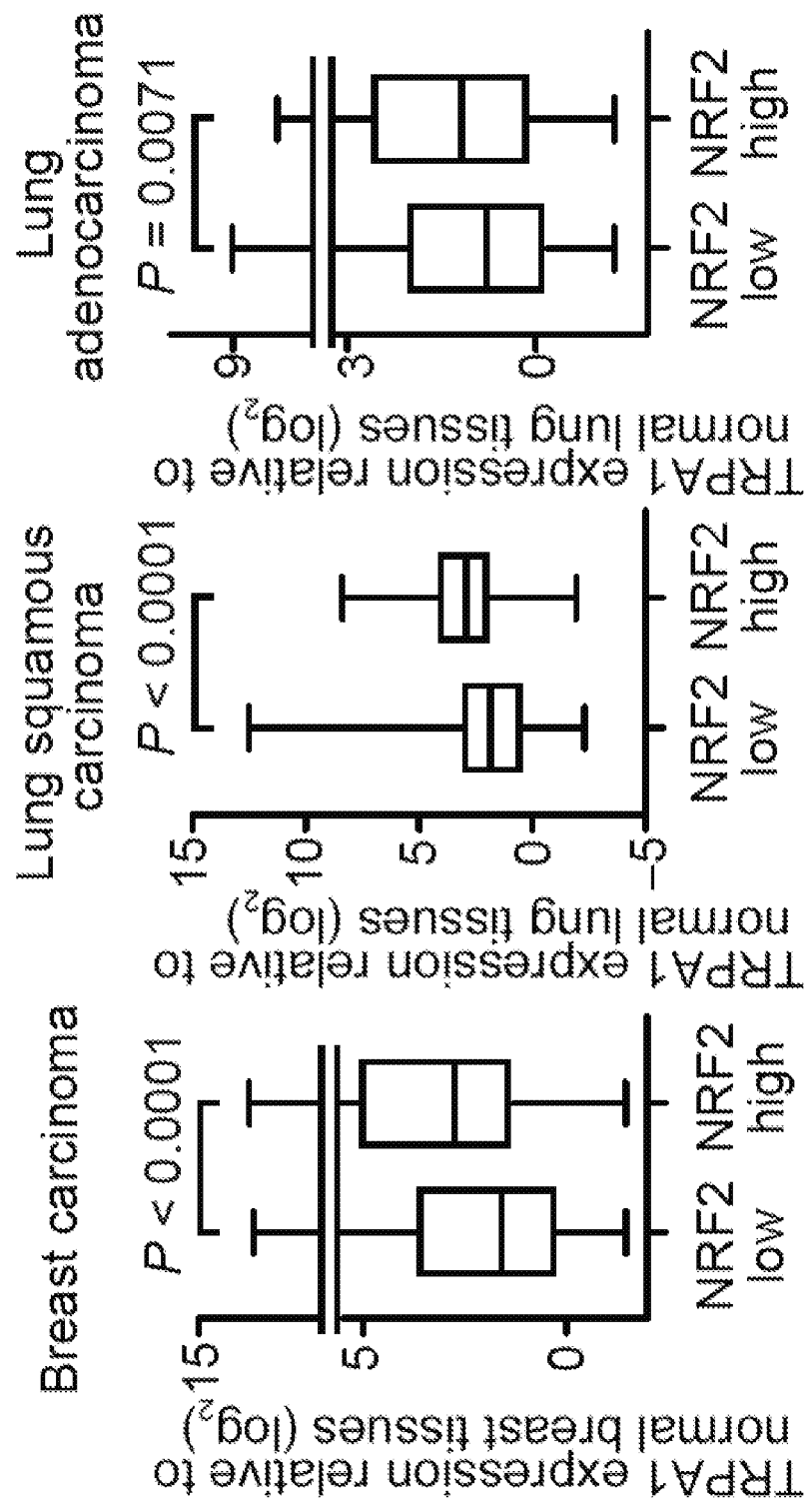
FIG. 8C is a series of box plots displaying TRPA1 mRNA levels relative to corresponding normal tissues in low or high NRF2 tumors from human breast carcinoma (n=578), lung squamous carcinoma (n=501), or lung adenocarcinoma (n=517). Low or high NRF2 tumors were determined by the expression level of classical NRF2 target genes. Statistical significance was determined by the Student's t test.
Figures 8D, 8E:
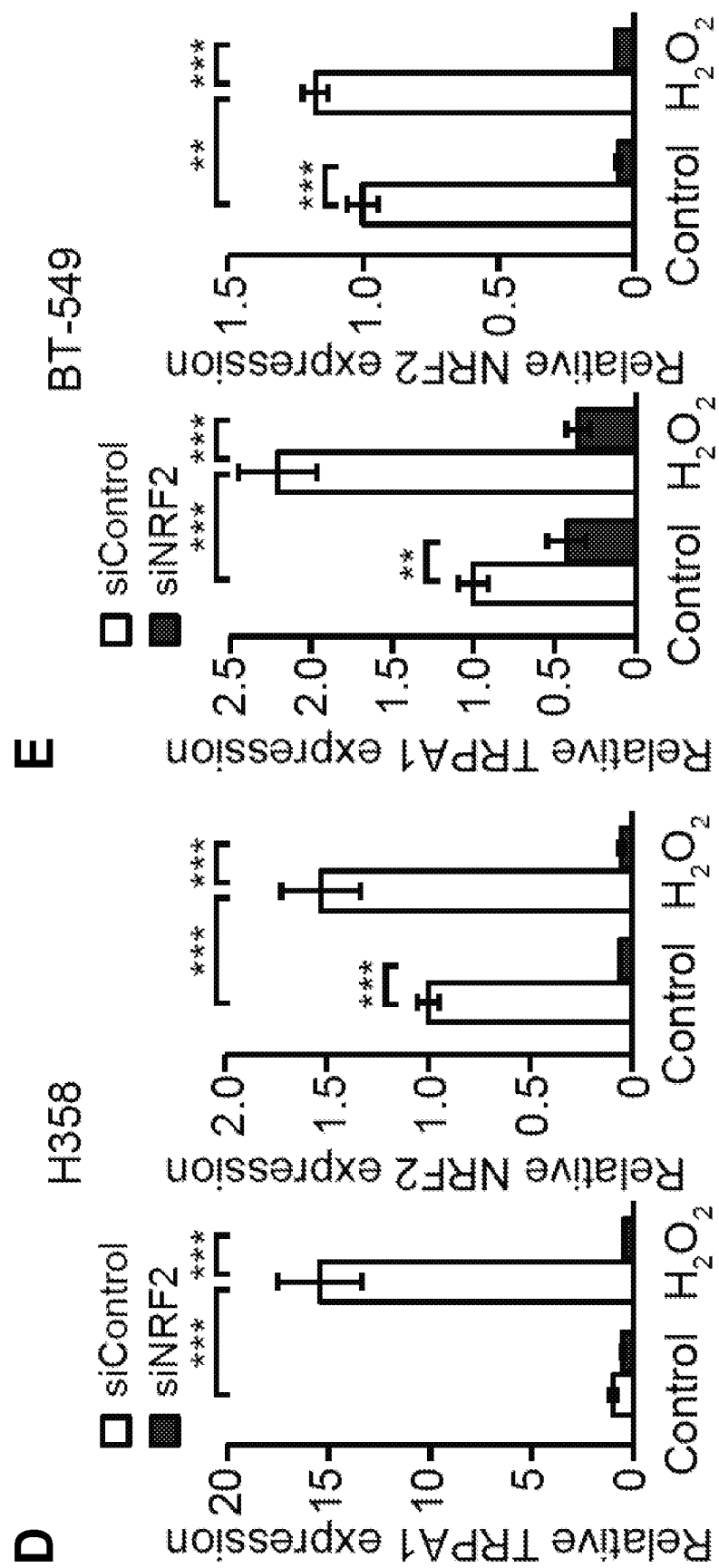
FIG. 8D is a graph of mRNA expression of TRPA1 in H358 transfected with siControl or siNRF2 upon treatment with or without 10 μM H$_2$O$_2$ for 48 h in serum-starved conditions. Data were normalized to siControl cells treated with vehicle control. Data are shown as mean±SD of three independent experiments. ***P<0.001 (one-way ANOVA).
FIG. 8E is a graph of mRNA expression of TRPA1 in BT-549 cells transfected with siControl or siNRF2 upon treatment with or without 10 μM H$_2$O$_2$ for 48 h in serum-starved conditions. Data were normalized to siControl cells treated with vehicle control. Data are shown as mean±SD of three independent experiments. P<0.01 and *P<0.001 (one-way ANOVA).

We next asked whether cancer cells upregulate TRPA1 expression in response to oxidative stress as an oxidative-stress defense program. In breast cancer BT-549 and lung cancer H358 cells, which exhibited low TRPA1 expression, H₂O₂ treatment increased TRPA1 expression substantially in serum-starved conditions (0.1% FBS) (FIG. 8A). By contrast, $H_2O_2$ did not enhance TRPA1 expression in breast cancer HCC1569 and lung cancer H1792 and H647 cells which display high basal TRPA1 expression [TRPA1 is amplified (5 copies) in HCC1569 cells, and NRF2, the ROS-activated transcription factor, is constitutively activated in H1792 and H647 cells by a mutation in KEAP1, which encodes a negative regulator of NRF2] (FIG. 8B). Interestingly, TRPA1 expression was statistically enriched in human breast and lung tumors that exhibit high activity of NRF2 (FIG. 8C), as determined by the expression level of well-characterized NRF2 target genes, not only suggesting that TRPA1-enriched tumor cells are exposed to oxidative stress, but also raising the possibility that oxidative stress induces TRPA1 expression through NRF2 activation. Indeed, $H_2O_2$-induced TRPA1 expression was abolished by NRF2 knockdown in BT-549 and H358 cells (FIGS. 8D and 8E), indicating that NRF2 is required for $H_2O_2$-induced TRPA1 expression. Thus, these results suggest that oxidative stress could at least partly contribute to enhanced TRPA1 expression in human tumor cells through ROS-induced NRF2 activation. This may, in part, explain the reason why the number of TRPA1-enriched cancer cell lines is limited in contrast to marked TRPA1 upregulation in human tumors—that is, the oxidative tumor microenvironments, which is greatly different between human tumors and cell lines in tissue culture, is an important factor for the induction of TRPA1 expression.

Figures 8F, 8G:
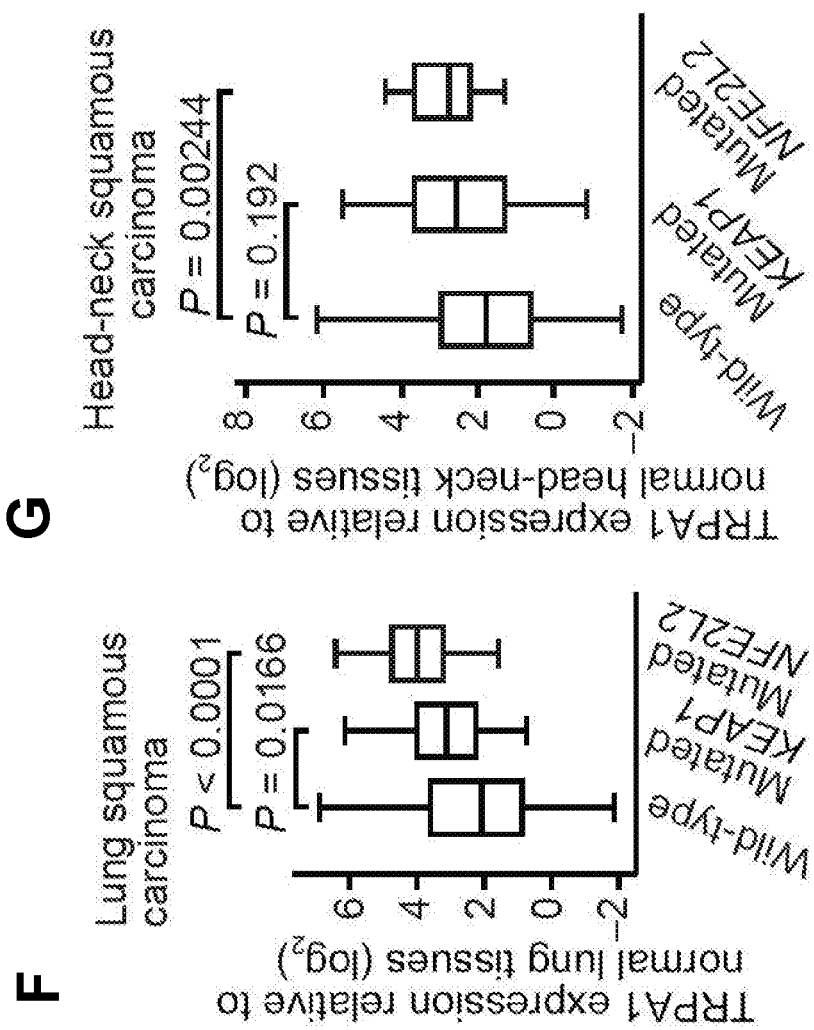
FIG. 8F is a series of box plots displaying TRPA1 mRNA levels relative to normal lung tissues in wild-type (n=114) and KEAP1- (n=22) or NFE2L2-mutated (n=26) lung squamous cell carcinoma based on TOGA dataset. Statistical significance was determined by the Student's t test.
FIG. 8G is a series of box plots displaying TRPA1 mRNA levels relative to normal head-neck tissues in wild-type (n=249) and KEAP1- (n=13) or NFE2L2-mutated (n=17) head-neck squamous cell carcinoma based on TOGA dataset. Statistical significance was determined by the Student's t test.

Mutations or deletions in NFE2L2 (encoding NRF2), KEAP1 (encoding a negative regulator of NRF2), or CUL3 (encoding another negative regulator of NRF2), which lead to a constitutive activation of NRF2, are frequently observed in lung squamous carcinoma (32.8%) and adenocarcinoma (22.6%) and head-neck squamous carcinoma (14.3%), but rarely occur in breast carcinoma (1.8%). Notably, in lung and head-neck squamous carcinoma, TRPA1 expression was highly upregulated in tumors harboring NFE2L2 or KEAP1 mutations (FIGS. 8F and 8G). Moreover, based on data from the COSMIC—Cell Lines Project (cancer.sanger.ac.uk/cell_lines), all TRPA1-enriched lung cancer cell lines, including H1792, H647, and A549 cells, except for HLF-a cells, whose genetic information is not available in the database, harbor KEAP1 mutations. This evidence, together with the fact that these lung cancer cell lines exhibit constitutive activation of NRF2, raises the possibility that constitutive activation of NRF2 leads to the induction of TRPA1 expression in lung cancer cells.

Figure 8H:
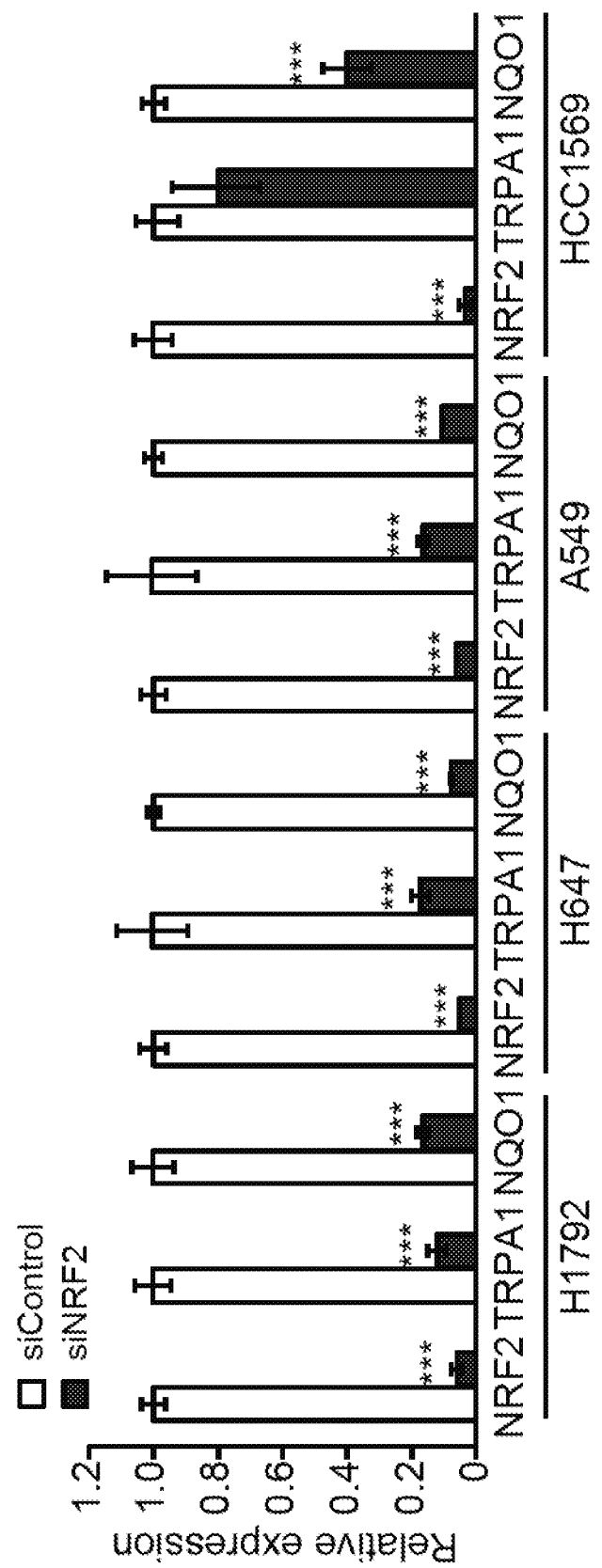
FIG. 8H is a graph of mRNA expression of NRF2, TRPA1, and NOO1 in the indicated cancer cells transfected with siControl or siNRF2. Data were normalized to siControl. Data are shown as mean±SD of three independent experiments. *** P<0.001 compared to siControl (Student's t test).

To address whether enhanced expression of TRPA1 in lung cancer cell lines is due to constitutive activation of NRF2, we examined the effect of NRF2 knockdown on TRPA1 expression. NRF2 knockdown strongly suppressed expression of TRPA1 as well as NQO1, a known NRF2 target gene, in lung cancer H1792, H647 and A549 cells, but not in breast cancer HCC1569 cells (FIG. 8H), indicating that constitutive NRF2 activation supports TRPA1 expression in these TRPA1-enriched lung cancer cell lines (in HCC1569 cells, high TRPA1 expression may be due to TRPA1 amplification). These results indicate that in addition to oxidative stress, genetic alterations of NFE2L2, KEAP1, and CUL3 also trigger TRPA1 expression through constitutive activation of NRF2 in lung tumors.

Figure 8I:
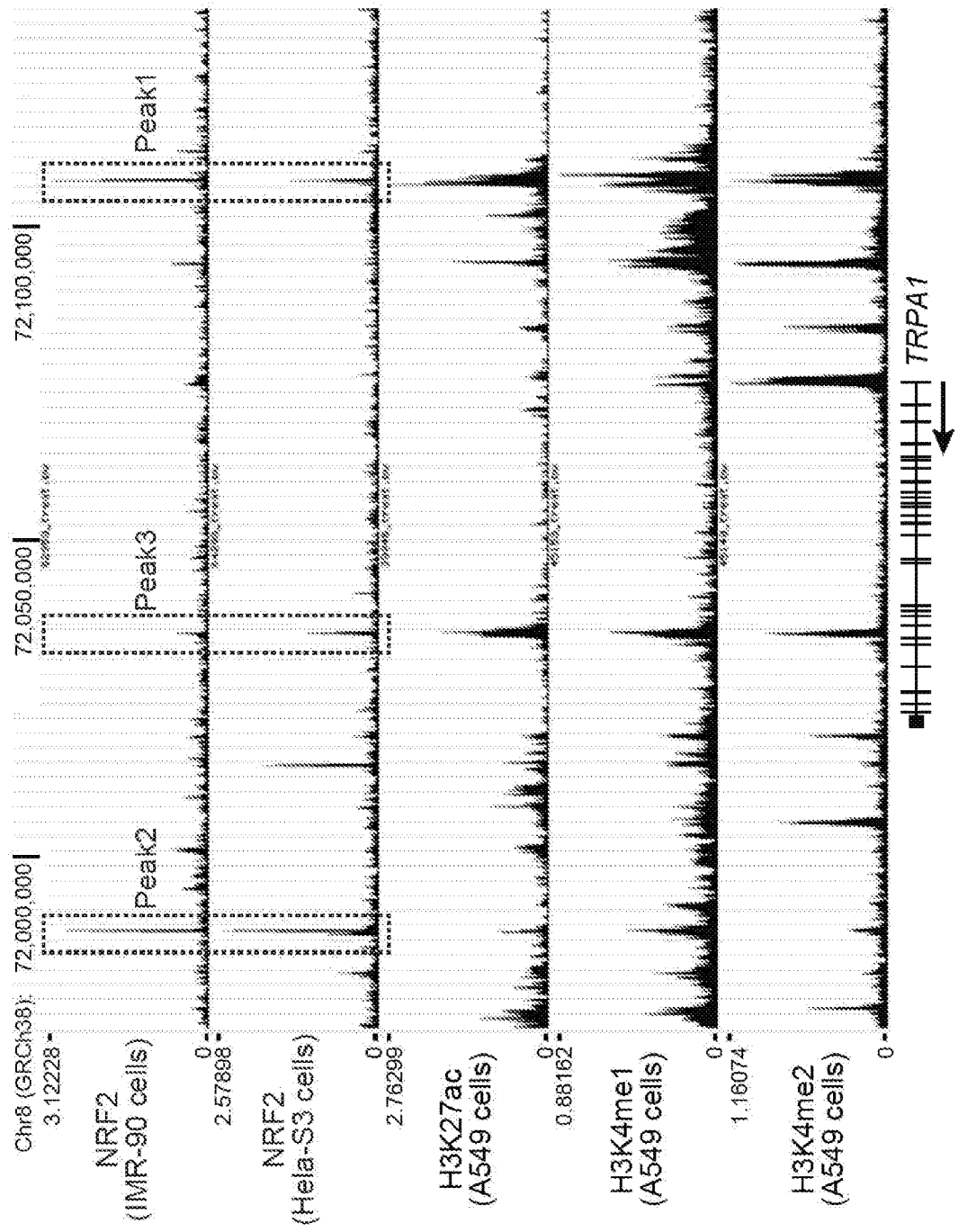
FIG. 8I is a graph of Cistrome ChIP-seq data (cistrome.org). The distribution of NRF2, histone H3K27ac, H3K4me1, and H3K36me2 are plotted around the TRPA1 locus.
Figure 8J:
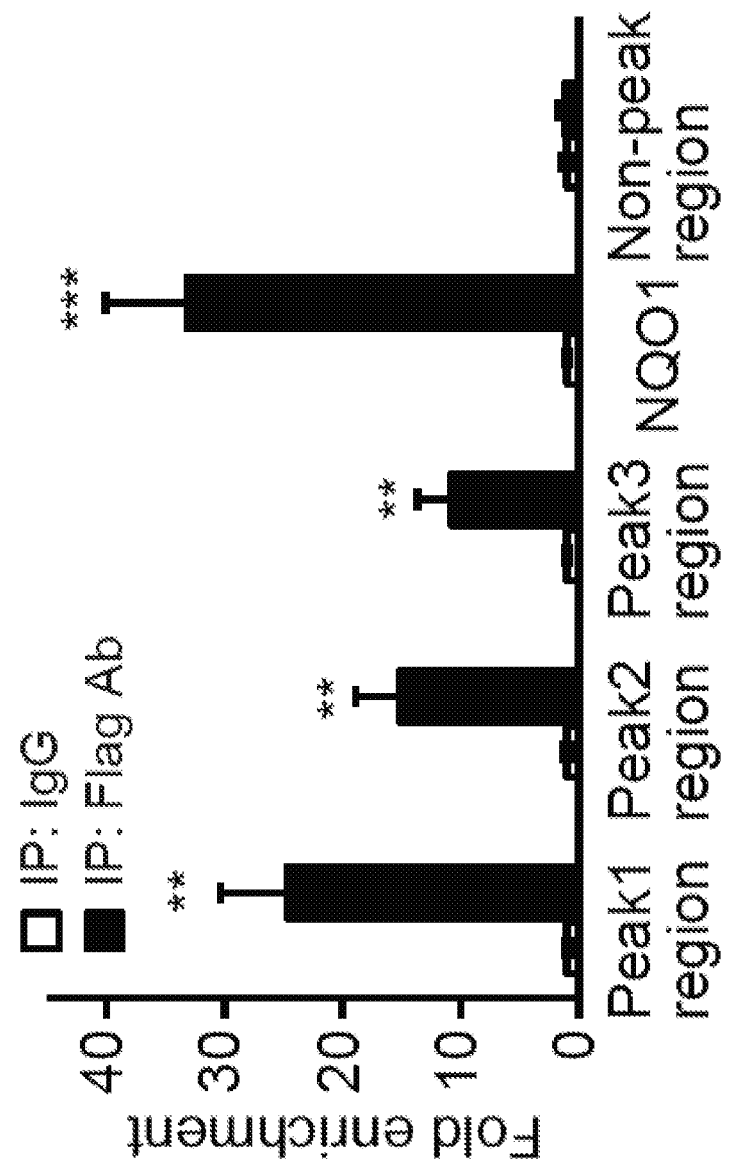
FIG. 8J is a graph of chromatin immunoprecipitation with Flag antibody of the fragmented chromatin containing the Peak1 [Chr8: 72107522-72107682 (GRCh38)], Peak2 [Chr8: 71987814-71987948 (GRCh38)], Peak3 [Chr8: 72035191-72035330 (GRCh38)], or non-Peak region [Chr8: 72086158-72086422 (GRCh38)] or the NOO1 promoter [Chr16: 69727000-69727111 (GRCh38)] in Flag-NRF2-overexpressing H1792 cells. Binding was normalized to that in immunoprecipitation with IgG control. Data are shown as mean±SD of three independent experiments. P<0.01 and *P<0.001 compared to IgG (Student's t test).
Figure 8K:
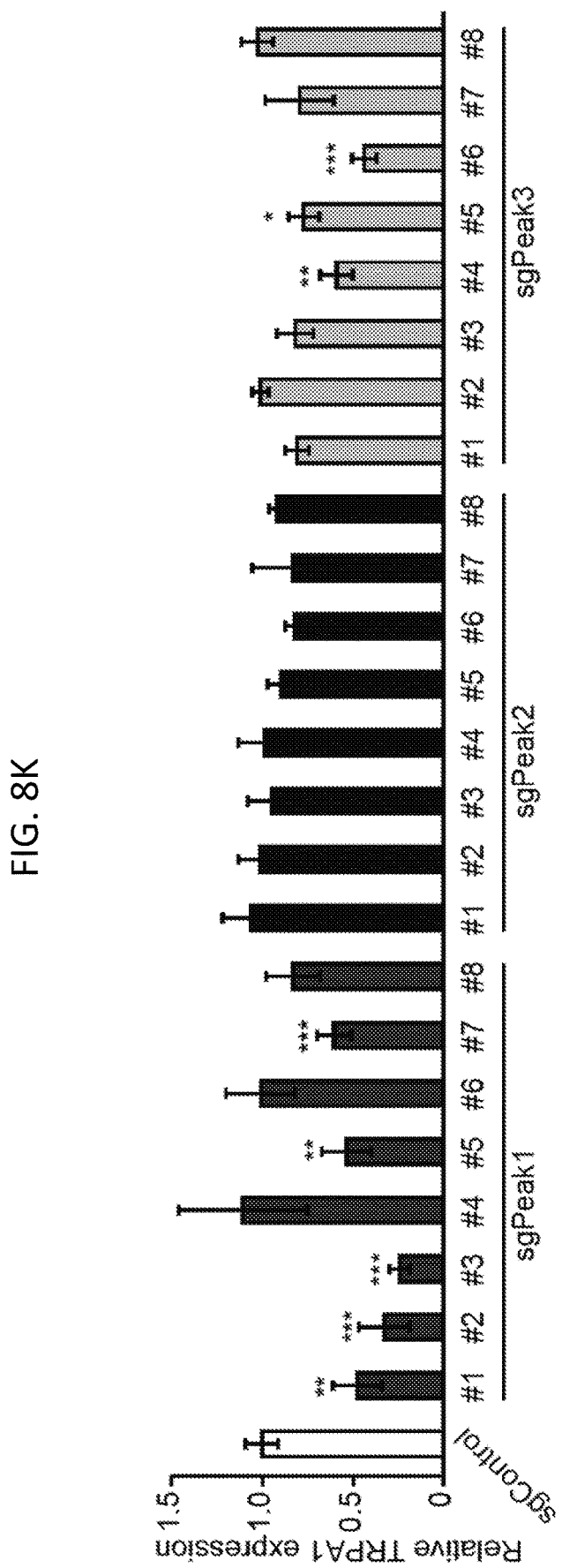
FIG. 8K is a graph of mRNA expression of TRPA1 in H1792 cells transduced with Cas9 plus sgControl, sgPeak1, sgPeak2, or sgPeak3. Data were normalized to sgControl. Data are shown as mean±SD of three independent experiments. *P<0.05, P<0.01, and *P<0.001 compared to sgControl (Student's t test).
Figure 8L:
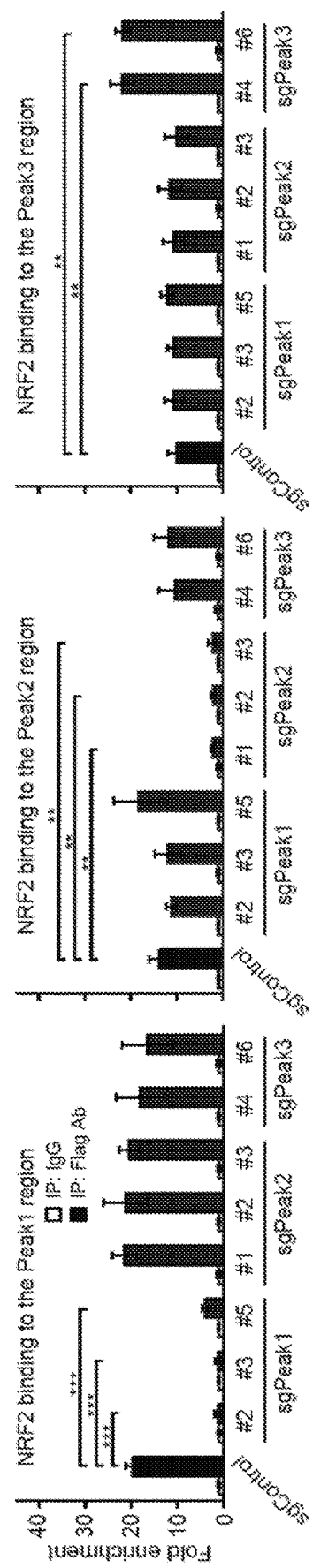
FIG. 8L is a series of graphs of chromatin immunoprecipitation with Flag antibody of the fragmented chromatin containing the Peak1, Peak2, or Peak3 region in Flag-NRF2-overexpressing H1792 cells transduced with Cas9 plus sgControl, sgPeak1, sgPeak2, or sgPeak3. Binding was normalized to that in immunoprecipitation with IgG control. Data are shown as mean±SD of three independent experiments. P<0.01 and *P<0.001 (Student's t test).
Figures 8M, 8N:
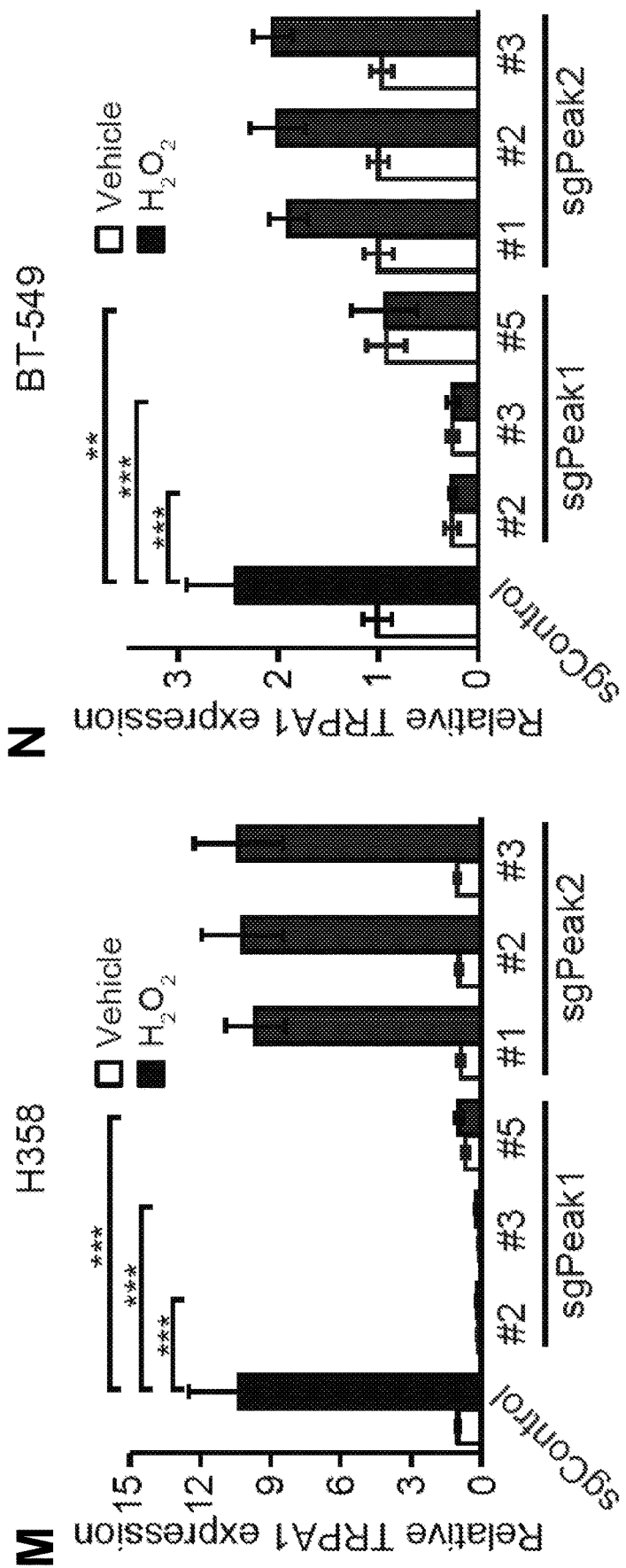
FIG. 8M is a graph of mRNA expression of TRPA1 in H358 cells transduced with Cas9 plus sgControl, sgPeak1, or sgPeak2 upon treatment with or without 10 μM $H_2O_2$ for 48 h in serum-starved conditions. Data were normalized to sgControl cells treated with vehicle control. Data are shown as mean±SD of three independent experiments. ***P<0.001 (Student's t test).
FIG. 8N is a graph of mRNA expression of TRPA1 in BT-549 cells transduced with Cas9 plus sgControl, sgPeak1, or sgPeak2 upon treatment with or without 10 μM $H_2O_2$ for 48 h in serum-starved conditions. Data were normalized to sgControl cells treated with vehicle control. Data are shown as mean±SD of three independent experiments. P<0.01 and *P<0.001 (Student's t test).

Based on chromatin immunoprecipitation-coupled deep sequencing (ChIP-Seq) dataset provided by Cistrome (cistrome.org), there are three putative NRF2 binding sites (Peak1, Peak2, and Peak3), which overlap with H3K27Ac, H3K4me1, and H3K4me2 signals (markers of promoter and enhancer regions), around the TRPA1 locus (FIG. 8I). Indeed, chromatin immunoprecipitation (ChIP) of NRF2-associated DNA sequences showed NRF2 binding to these peak regions as well as the promoter region of NQO1 in H1792 cells (FIG. 8J). We therefore disrupted these regions by CRISPR-Cas9 technology (sgPeak1, sgPeak2, or sgPeak3) and assessed TRPA1 expression. TRPA1 expression was suppressed substantially by sgPeak1-targeted constructs and marginally by sgPeak3-targeted constructs, but not by sgPeak2-targeted constructs, in H1792 cells (FIG. 8K). Interestingly, NRF2 binding to the Peak1 and Peak2 was abolished by sgPeak1- and sgPeak2-targeted constructs, respectively; however, sgPeak3-targeted constructs did not reduce NRF2 binding to the Peak3 region (FIG. 8L). Given that the Peak3 is located in intron 21 of TRPA1 (FIG. 8I), the marginal suppression of TRPA1 expression by sgPeak3 targeting could be at least in part due to defects in splicing or other intron-mediated enhancement mechanisms, independent of NRF2 binding. Furthermore, $H_2O_2$-induced TRPA1 expression was abolished by sgPeak1-targeted constructs in BT-549 and H358 cells (FIGS. 8M and 8N). Collectively, these results suggest that NRF2 can directly induce TRPA1 expression through its binding to the Peak1 region.

Figure 8O:
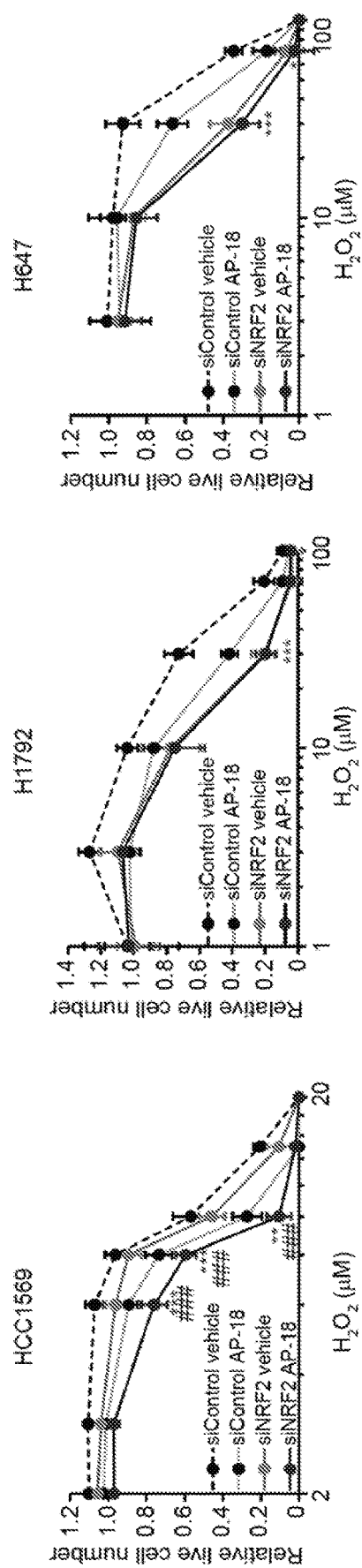
FIG. 8O is a series of graphs of live cell numbers relative to $H_2O_2$-untreated cells in the indicated cancer cells transfected with siControl or siNRF2 upon treatment with $H_2O_2$ for 72 h in the presence or absence of 10 μM AP-18. Data are shown as mean±SD from the sum of three independent experiments performed in duplicate. *P<0.05, P<0.01, and *P<0.001 compared to siControl cells treated with AP-18 (Student's t test). ####P<0.001 compared to siNRF2 cells treated with vehicle.
Figure 8P:
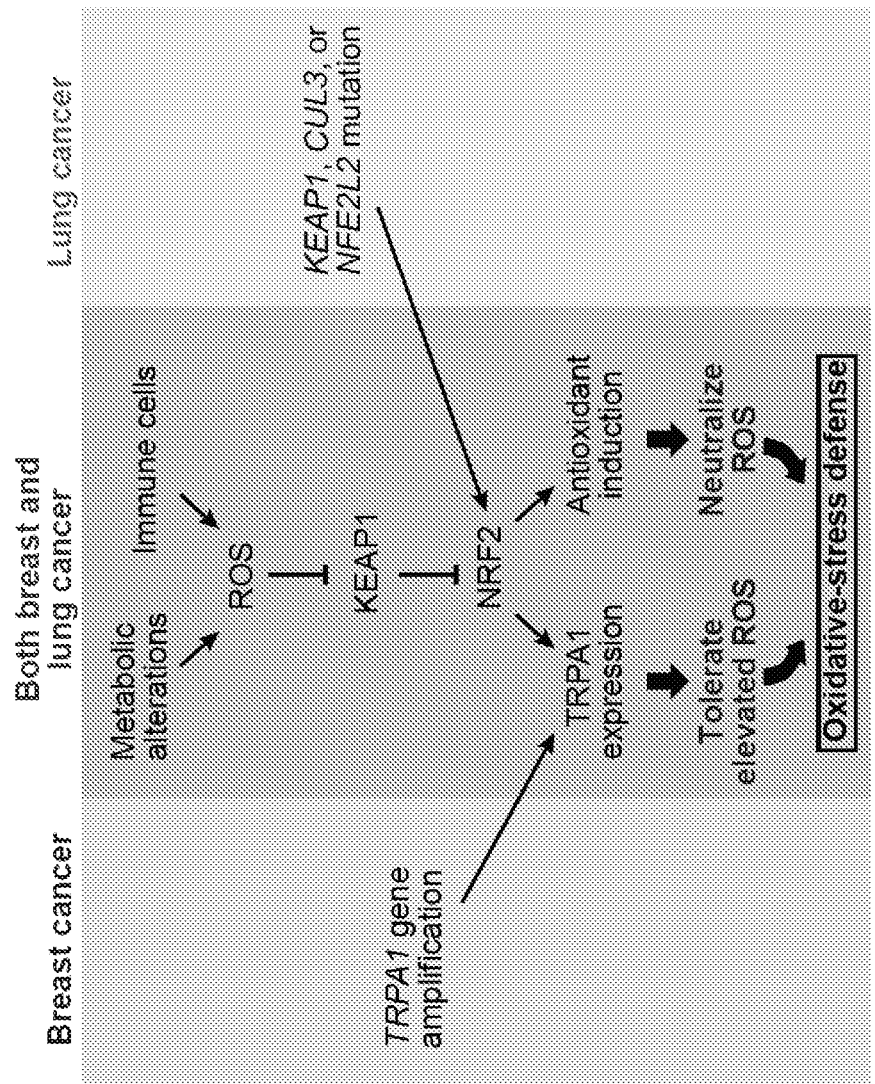
FIG. 8P is a model of the induction of TRPA1 in breast and lung cancer. Oxidative stress can induce TRPA1 expression through activation of NRF2 in both breast and lung cancer cells. TRPA1 amplification (observed in breast cancer) and NFE2L2/KEAP1/CUL3 mutations (observed in lung cancer) also contribute to TRPA1 expression. To adapt to harsh oxidative environments, cancer cells may drive two key defense programs against oxidative stress—that is, TRPA1-induced oxidative-stress tolerance and antioxidant-mediated ROS-neutralizing programs.

Finally, to explore how much of the ability to adapt to oxidative stress is contributed by TRPA1-dependent and TRPA1-independent programs, we investigated the effect of inhibition of TRPA1, NRF2, or both on cell survival in breast cancer HCC1569 and lung cancer H1792 and H647 cells, where TRPA1 expression was not affected by $H_2O_2$ (FIG. 8B), upon $H_2O_2$ treatment. Given that only a handful of early-stage NRF2 inhibitors have been developed to date and that the selectivity of these drugs for NRF2 has not been evaluated, we performed NRF2 knockdown for the inhibition. In TRPA1-amplified breast cancer HCC1569 cells, inhibition of either TRPA1 or NRF2 suppressed cell survival, and as expected based on the unaffected TRPA1 expression by NRF2 knockdown in this cell line, dual inhibition of TRPA1 and NRF2 reduced cell survival more than single inhibition of each one (FIG. 8O), suggesting that TRPA1-dependent and TRPA1-independent NRF2-mediated programs separately contribute to oxidative-stress defense in this cell line. By contrast, in KEAP1-mutated lung cancer H1792 and H647 cells, NRF2 inhibition suppressed cell survival more than TRPA1 inhibition as expected based on the strong reduction of TRPA1 expression by NRF2 knockdown in these cell lines, and TRPA1 inhibition failed to affect cell survival in NRF2-knockdown cells (FIG. 8O), suggesting that NRF2 induces both TRPA1-dependent and TRPA1-independent programs in these cell lines. Collectively, these results, together with the known importance of NRF2 in ROS-neutralizing gene expression in response to oxidative stress in cancer cells, suggest that cancer cells utilize two key defense programs against oxidative stress, namely a TRPA1-mediated anti-apoptotic program that allows tumor cells to tolerate oxidative stress and ROS-neutralizing programs that reduce cellular ROS, in order to survive harsh oxidative challenges (FIG. 8P).

Other Embodiments

Although the foregoing invention has been described in some detail by way of illustration and example for purposes of clarity of understanding, the descriptions and examples should not be construed as limiting the scope of the invention. The disclosures of all patents, patent applications, scientific references, and GenBank Accession Nos. cited herein are expressly incorporated by reference in their entirety for all purposes as if each patent, patent application, scientific reference, and GenBank Accession No. were specifically and individually incorporated by reference.

The invention claimed is:

1. A method for the treatment of cancer in a subject, the method comprising:
   (a) determining the expression level of a gene in a cancer sample from a subject diagnosed with cancer, wherein the gene encodes a transient receptor potential cation channel, subfamily A, member 1 (TRPA1) channel; and
   (b) administering an anti-cancer agent and an antagonist of the TRPA1 channel to the subject if the expression level of the gene encoding the TRPA1 channel is increased relative to a control biological sample, wherein the anti-cancer agent and the antagonist of the TRPA1 channel are administered in amounts and for durations sufficient to treat cancer in the subject.

2. A method for the treatment of cancer in a subject whose cancer has higher expression levels of a gene encoding a TRPA1 channel relative to a control biological sample, the method comprising administering an anti-cancer agent and an antagonist of the TRPA1 channel to the subject wherein the anti-cancer agent and the antagonist of the TRPA1 channel are administered in amounts and for durations sufficient to treat cancer in the subject.

3. A method for the treatment of cancer in a subject, the method comprising:
   (a) administering an anti-cancer agent to a subject diagnosed with cancer;
   (b) determining whether the anti-cancer agent increases the expression level of a gene in a cancer sample from a subject, wherein the gene encodes a TRPA1 channel; and
   (c) administering the anti-cancer agent and an antagonist of the TRPA1 channel to the subject if the expression level of the gene encoding the TRPA1 channel is higher relative to a control biological sample, wherein the anti-cancer agent and the antagonist of the TRPA1 channel are administered in amounts and for durations sufficient to treat cancer in the subject.

4. The method of claim 1, wherein the cancer is sarcoma, adenocarcinoma, carcinoma, colon cancer, rectal cancer, renal-cell carcinoma, liver cancer, non-small cell carcinoma of the lung (NCSLC), cancer of the small intestine and cancer of the esophagus, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, acute myeloid leukemia (AML), chronic myeloid leukemia, acute lymphoblastic leukemia (ALL), chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, spinal axis tumor, brain stem glioma, pituitary adenoma, Kaposi's sarcoma, epidermoid cancer, squamous cell cancer, T-cell lymphoma, an environmentally induced cancer, cancer caused by asbestos, or a combination thereof.

5. The method of claim 1, wherein the antagonist of the TRPA1 channel targets a gene, gene product, or regulatory RNAs of the TRPA1 channel.

6. The method of claim 1, wherein the anti-cancer agent is a chemotherapeutic agent, a cytotoxic agent, a growth inhibitory agent, radiation therapy, surgery, or a combination thereof.

7. The method of claim 6, wherein the anti-cancer agent further comprises doxorubicin, gemcitabine, platinum-based drugs, radiotherapy, tamoxifen, methotrexate, arsenic trioxide, or an aromatase inhibitor.

8. The method of claim 6, wherein the anti-cancer agent is carboplatin.

9. The method of claim 1, wherein the expression level of a gene is determined by determining mRNA expression level, cDNA expression level, or protein expression level.

10. The method of claim 1, wherein the biological sample comprises mRNA, cDNA, or protein from the subject.

11. The method of claim 1, wherein:
    (a) the TRPA1 channel antagonist and doxorubicin are used in combination for the treatment of ALL, AML, breast cancer, gastric cancer, Hodgkin lymphoma, neuroblastoma, non-Hodgkin lymphoma, ovarian cancer, small cell lung cancer, soft tissue and bone sarcomas, thyroid cancer, transitional cell bladder cancer, or Wilms tumor;
    (b) the TRPA1 channel antagonist and gemcitabine are used in combination for the treatment of breast cancer, NSCLC, ovarian cancer, or pancreatic cancer; or
    (c) the TRPA1 channel antagonist, gemcitabine, and paclitaxel are used in combination for the treatment of breast cancer or pancreatic cancer.

12. The method of claim 1, wherein:
    (a) the TRPA1 channel antagonist, gemcitabine, and cisplatin are used in combination for the treatment of NSCLC;
    (b) the TRPA1 channel antagonist, gemcitabine, and carboplatin are used in combination for the treatment of ovarian cancer; or
    (c) the TRPA1 channel antagonist and tamoxifen are used in combination for the treatment of breast cancer.

13. The method of claim 1, wherein:
    (a) the TRPA1 channel antagonist and methotrexate are used in combination for the treatment of ALL, breast cancer, gestational trophoblastic disease, head and neck cancer, lung cancer, mycosis fungoides, non-Hodgkin lymphoma, or osteosarcoma;
    (b) the TRPA1 channel antagonist and arsenic trioxide are used in combination for the treatment of acute promyelocytic leukemia; or
    (c) the TRPA1 channel antagonist and anastrozole are used in combination for the treatment of breast cancer.

14. The method of claim 1, wherein:
    (a) the TRPA1 channel antagonist and exemestane are used in combination for the treatment of breast cancer; or
    (b) the TRPA1 channel antagonist and letrozole are used in combination for the treatment of breast cancer.

15. The method of claim 1, wherein:
    (a) the TRPA1 channel antagonist and formestane are used in combination for the treatment of breast cancer; or
    (b) the TRPA1 channel antagonist and fadrozole are used in combination for the treatment of breast cancer.

16. The method of claim 1, wherein:
(a) the TRPA1 channel antagonist and cisplatin are used in combination for the treatment of bladder cancer, ovarian cancer, or testicular cancer;
(b) the TRPA1 channel antagonist and carboplatin are used in combination for the treatment of ovarian cancer; or
(c) the TRPA1 channel antagonist and oxaliplatin are used in combination for the treatment of colorectal cancer or colon cancer.

17. The method of claim 1, wherein:
(a) the TRPA1 channel antagonist and nedaplatin are used in combination for the treatment of squamous cell lung cancer, NSCLC, esophageal cancer, uterine cervical cancer, head and neck cancer, or urothelial cancer; or
(b) the TRPA1 channel antagonist and triplatin tetranitrate are used in combination for the treatment of ovarian cancer, small cell lung cancer, or gastric cancer.

18. The method of claim 1, wherein:
(a) the TRPA1 channel antagonist and phenanthriplatin are used in combination for the treatment of leukemias, NSCLC, colon cancer, CNS cancers, melanoma, ovarian cancer, renal cancer, prostate cancer, or breast cancer;
(b) the TRPA1 channel antagonist and picoplatin are used in combination for the treatment of lung cancer, ovarian cancer, colorectal cancer, or hormone-refractory prostate cancer; or
(c) the TRPA1 channel antagonist and satraplatin are used in combination for the treatment of prostate cancer, lung cancer, or ovarian cancer.

\* \* \* \* \*